US012694947B2

(12) United States Patent
McGovern et al.

(10) Patent No.: US 12,694,947 B2
(45) Date of Patent: Jul. 28, 2026

(54) METHODS AND SYSTEMS FOR ASSESSING INFLAMMATORY DISEASE WITH DEEP LEARNING

(71) Applicant: Cedars-Sinai Medical Center, Los Angeles, CA (US)

(72) Inventors: Dermot P. McGovern, Los Angeles, CA (US); Dalin Li, Walnut, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 1074 days.

(21) Appl. No.: 16/855,963

(22) Filed: Apr. 22, 2020

(65) Prior Publication Data

US 2020/0342958 A1    Oct. 29, 2020

Related U.S. Application Data

(60) Provisional application No. 62/849,688, filed on May 17, 2019, provisional application No. 62/837,617, filed on Apr. 23, 2019.

(51) Int. Cl.
*G16B 20/20* (2019.01)
*G16H 50/20* (2018.01)

(52) U.S. Cl.
CPC ............. *G16B 20/20* (2019.02); *G16H 50/20* (2018.01)

(58) Field of Classification Search
None
See application file for complete search history.

(56) References Cited

U.S. PATENT DOCUMENTS

| | | | |
|---|---|---|---|
| 2008/0131439 A1 * | 6/2008 | Lois et al. | |
| 2011/0218956 A1 | 9/2011 | Lois et al. | |
| 2012/0171672 A1 * | 7/2012 | Barken et al. | |
| 2015/0072879 A1 | 3/2015 | Princen et al. | |
| 2018/0218789 A1 | 8/2018 | Anderson et al. | |
| 2019/0108902 A1 | 4/2019 | Parthan et al. | |
| 2019/0108912 A1 | 4/2019 | Spurlock, III et al. | |
| 2019/0114544 A1 | 4/2019 | Sundaram et al. | |
| 2020/0102610 A1 | 4/2020 | Bahado-Singh | |
| 2023/0230655 A1 | 7/2023 | McGovern et al. | |

FOREIGN PATENT DOCUMENTS

| | | |
|---|---|---|
| WO | WO-2019005847 A1 | 1/2019 |
| WO | WO-2019200410 A1 | 10/2019 |
| WO | WO-2020219549 A1 | 10/2020 |
| WO | WO-2021222618 A1 | 11/2021 |

OTHER PUBLICATIONS

Kelley, D. R., Reshef, Y. A., Bileschi, M., Belanger, D., McLean, C. Y., & Snoek, J. (2018). Sequential regulatory activity prediction across chromosomes with convolutional neural networks. Genome research, 28(5), 739-750. https://doi.org/10.1101/gr.227819.117 (Year: 2018).*

Wingfield, B., Coleman, S., McGinnity, T. M., & Bjourson, A. J. (2018). Robust Microbial Markers for Non-Invasive Inflammatory Bowel Disease Identification. IEEE/ACM transactions on computational biology and bioinformatics, 16(6), 2078-2088. (Year: 2018).*

Christodoulou, K., Wiskin, A. E., Gibson, J., Tapper, W., Willis, C., Afzal, N. A., Upstill-Goddard, R., Holloway, J. W., Simpson, M. A., Beattie, (2013). Next generation exome sequencing of paediatric inflammatory bowel disease patients identifies rare and novel variants in candida (Year: 2013).*

Morilla, I., Uzzan, M., Laharie, D., Cazals-Hatem, D., Denost, Q., (2019). Colonic MicroRNA Profiles, Identified by a Deep Learning Algorithm, That Predict Responses to Therapy of Patients With Acute Severe Ulcerative Colitis (Year: 2019).*

Poirion, O. B., Chaudhary, K., & Garmire, L. X. (2018). Deep Learning data integration for better risk stratification models of bladder cancer. AMIA Joint Summits on Translational Science proceedings. AMIA Joint Summits on Translational Science, 2017, 197-206. (Year: 2017).*

Tcymbarevich IV, Eloranta JJ, Swiss IBD Cohort Study Group. The impact of the rs8005161 polymorphism on G protein-coupled receptor GPR65 (TDAG8) pH-associated activation in intestinal inflammation. BMC Gastroenterol. Jan. 7, 2019;19(1):2 (Year: 2019).*

Plevy et al. "Combined Serological, Genetic, and Inflammatory Markers Differentiate Non-IBD, Crohn's Disease, and Ulcerative Colitis Patients." Inflammatory bowel diseases n. pag. Web.(2013) (Year: 2013).*

Kevans, David et al. "IBD Genetic Risk Profile in Healthy First-Degree Relatives of Crohn's Disease Patients." Journal of Crohn's and colitis 10.2 (2016): 209-215. Web. (Year: 2016).*

Yazdanyar, S, and B. G Nordestgaard. "NOD2/CARD15 Genotype and Common Gastrointestinal Diseases in 43 600 Individuals." Journal of internal medicine 267.2 (2010): 228-236. Web. (Year: 2010).*

Misra, Maneesh Kumar et al. "Co-Stimulatory CD28 and Transcription Factor NFKB1 Gene Variants Affect Idiopathic Recurrent Miscarriages." Journal of human genetics 61.12 (2016): 1035-1041. Web. (Year: 2016).*

Peyrin-Biroulet et al. "Defining Disease Severity in Inflammatory Bowel Diseases: Current and Future Directions." Clinical gastroenterology and hepatology (2016): n. pag. Web. (Year: 2016).*

Doggett "The Polymerase chain reaction and Sequence-tagged site" Los Alamos Science, Mapping the Genome/The Polymerase Chain Reaction (1992): 128-134 (Year: 1992).*

(Continued)

*Primary Examiner* — Anna Skibinsky
*Assistant Examiner* — Joseph Pulliam
(74) *Attorney, Agent, or Firm* — JONES DAY

(57)        ABSTRACT

The present disclosure provides methods and systems of identifying an inflammatory disease or condition, e.g., an inflammatory bowel disease in a subject using a DeepLearning model. The DeepLearning model may be used to predict, treat, monitor, and/or prevent the inflammatory disease or condition in the subject, as well as to characterize a subtype of the inflammatory disease or condition.

19 Claims, 22 Drawing Sheets

(56) References Cited

OTHER PUBLICATIONS

Boyd, Mette et al. "Characterization of the Enhancer and Promoter Landscape of Inflammatory Bowel Disease from Human Colon Biopsies." Nature communications 9.1 (2018): 1661-19. Web. (Year: 2018).*

Yan, Jingwen et al. "Network Approaches to Systems Biology Analysis of Complex Disease: Integrative Methods for Multi-Omics Data." Briefings in bioinformatics 19.6 (2017): 1370-1381. Web. (Year: 2017).*

Tun, Gloria SZ, Sarah Cripps, and Alan J Lobo. "Crohn's Disease: Management in Adults, Children and Young People—Concise Guidance." Clinical medicine (London, England) 18.3 (2018): 231-236. Web. (Year: 2018).*

Khera et al.: Genome-wide polygenic scores for common diseases identify individuals with risk equivalent to monogenic mutations. Nature Genetics 50:1219-1224 (2018).

PCT/US2021/029962 International Preliminary Report on Patentability dated Nov. 10, 2022.

PCT/US2021/029962 International Search Report and Written Opinion dated Aug. 31, 2021.

Behravan et al.: Machine learning identifies interacting genetic variants contributing to breast cancer risk: a case study in Finnish cases and controls. Sci Rep. 8:13149 (2018).

De Lange et al.: Genome-wide association study implicates immune activation of multiple integrin genes in inflammatory bowel disease. Nat Genet.: 49(2):256-261 (2017).

Ellinghaus et al.: Analysis of five chronic inflammatory diseases identifies 27 new associations and highlights disease-specific patterns at shared loci. Nat. Genet. 48(5):510-518 (2016).

Jostins et al.: Host-microbe interactions have shaped the genetic architecture of inflammatory bowel disease; Nature 491, 119-124 (2012).

Jurman et al.: Convolutional neural networks for structured omics: OmicsCNN and the OmicsConv layer. Quantitative Methods. pp. 1-7 (2017).

Li et al.: Late-Onset Crohn's Disease is a Subgroup Distinct in Genetic and Behavioral Risk Factors with UC-Like Characteristics. Inflamm Bowel Dis. 12;24(11):2413-2422(2018).

Li et al.: Using Deeplearning and Genetic Bigdata to Predict Crohn's Disease . Aga Abstracts. 156(6):SUPPLEMENT 1, S-35 (2019).

PCT/US2020/029327 International Search Report and Written Opinion dated Jul. 22, 2020.

Terada et al.: LAMPLINK: detection of statistically significant SNP combinations from GWAS data. Bioinformatics. 32(22):3513-3515 (2016).

Wei et al. Large Sample Size, Wide Variant Spectrum, and Advanced Machine-Learning Technique Boost Risk Prediction for Inflammatory Bowel Disease. AJHG 92(6):1008-1012 (Jun. 6, 2013). DOI: https://doi.org/10.1016/j.ajhg.2013.05.002.

Anekboon et al.: Extracting predictive SNPs in Crohn's disease using a vacillating genetic algorithm and a neural classifier in case-control association studies. Computers in Biology and Medicine. 44:57-65 (2014).

European Patent Application No. EP20794865.4 European Search Report dated Dec. 16, 2022.

Prometheus Biosciences, Inc. Form S-1 Registration Statement as filed with the Securities and Exchange Commission on Feb. 19, 2021 (246 pages).

Liu et al.: Association analyses identify 38 susceptibility loci for inflammatory bowel disease and highlight shared genetic risk across populations; Nature Genetics; 47, 979-986 (2015).

Bahado-Singh et al.: Artificial intelligence analysis of newborn leucocyte epigenomic markers for the prediction of autism. Brain Research. Elsevier. 1724:146457 (2019).

Mamoshina et al.: Applications of Deep Learning in Biomedicine. Molecular Pharmaceutics. 13(5):1445-1454 (2016).

Zeybel et al.: Differential DNA methylation of genes involved in fibrosis progression in non-alcoholic fatty liver disease and alcoholic liver disease. Clinical Epigenetics. Biomed Central Ltd. 7(1):25 (2015).

Zhang et al.: Dust induces lung fibrosis through dysregulated DNA methylation. Environmental Toxicology. 34(6):728-741 (2019).

* cited by examiner

Crohn's disease vs ulcerative colitis

FIG. 8

| High GPS definition | Reference group | Odds ratio | 95% CI | P value |
|---|---|---|---|---|
| Inflammatory bowel disease | | | | |
| Top 20% of distribution | Remaining 80% | 2.19 | 2.03~2.36 | $7.7 \times 10^{-95}$ |
| Top 10% of distribution | Remaining 90% | 2.43 | 2.22~2.65 | $8.8 \times 10^{-88}$ |
| Top 5% of distribution | Remaining 95% | 2.66 | 2.38~2.96 | $3.0 \times 10^{-68}$ |
| Top 1% of distribution | Remaining 99% | 3.87 | 3.18~4.66 | $1.4 \times 10^{-43}$ |
| Top 0.5% of distribution | Remaining 99.5% | 4.81 | 3.74~6.08 | $9.0 \times 10^{-37}$ |

FIG. 11
Sigmoid
$\sigma(x) = \frac{1}{1+e^{-x}}$
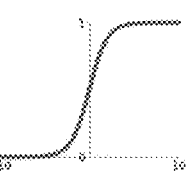
Leaky ReLU
$\max(0.1x, x)$
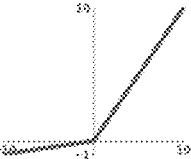
tanh
$\tanh(x)$
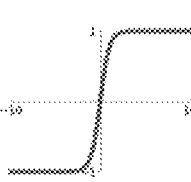
Maxout
$\max(w_1^T x + b_1, w_2^T x + b_2)$
ReLU
$\max(0, x)$
ELU
$\begin{cases} x & x \geq 0 \\ \alpha(e^x - 1) & x < 0 \end{cases}$
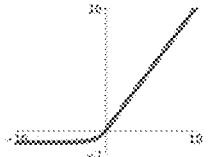

*Forward Propagation of Layer 1 Neurons*

Activation = g(BiasWeight1 + Weight1 * Input1 + Weight2 * Input2)

Forward Propagation of Layer 2 Neurons

FIG. 13

|  | Methods | N | OR | CI | p |
|---|---|---|---|---|---|
| ANCA (+/-) | DL-comb | 2354 | 0.47 | 0.30-0.72 | 6.63E-04 |
|  | DL-known | 2354 | 0.62 | 0.42-0.90 | 0.012 |
|  | DL-others | 2354 | 0.74 | 0.55-1.00 | 0.050 |
|  | LDpred | 2354 | 0.62 | 0.37-1.03 | 0.066 |
| CBir1 (+/-) | DL-comb | 2408 | 3.30 | 2.23-4.90 | 2.73E-09 |
|  | DL-known | 2408 | 2.53 | 1.82-3.52 | 3.75E-08 |
|  | DL-others | 2408 | 1.56 | 1.20-2.03 | 8.25E-04 |
|  | LDpred | 2408 | 2.24 | 1.43-3.51 | 4.42E-04 |
| I2 (+/-) | DL-comb | 1882 | 1.29 | 0.82-2.02 | 0.270 |
|  | DL-known | 1882 | 1.09 | 0.75-1.58 | 0.654 |
|  | DL-others | 1882 | 1.35 | 1.00-1.83 | 0.051 |
|  | LDpred | 1882 | 1.52 | 0.9-2.56 | 0.118 |
| IgA-ASCA (+/-) | DL-comb | 2328 | 4.13 | 2.66-6.41 | 2.77E-10 |
|  | DL-known | 2328 | 2.73 | 1.91-3.91 | 3.91E-08 |
|  | DL-others | 2328 | 2.08 | 1.56-2.79 | 7.42E-07 |
|  | LDpred | 2328 | 2.63 | 1.61-4.32 | 1.22E-04 |
| IgG-ASCA (+/-) | DL-comb | 2328 | 5.54 | 3.58-8.58 | 1.55E-14 |
|  | DL-known | 2328 | 3.63 | 2.55-5.18 | 9.31E-13 |
|  | DL-others | 2328 | 2.08 | 1.56-2.76 | 4.70E-07 |
|  | LDpred | 2328 | 3.33 | 2.05-5.42 | 1.25E-06 |
| OmpC (+/-) | DL-comb | 2375 | 1.20 | 0.76-1.87 | 0.435 |
|  | DL-known | 2375 | 1.18 | 0.82-1.72 | 0.375 |
|  | DL-others | 2375 | 1.20 | 0.88-1.62 | 0.244 |
|  | LDpred | 2375 | 1.44 | 0.86-2.41 | 0.166 |

FIG. 15

| # of Alleles | In Cedars | | In IIBDGC | |
|---|---|---|---|---|
| | CD+ | CD- | CD+ | CD- |
| 0 | 2307 | 4377 | 13116 | 22771 |
| 1 | 307 | 186 | 1888 | 1149 |
| 2 | 229 | 5 | 271 | 17 | rs5743293

In Cedars
1 vs 0: OR=2.90, p=1.39E-23
2 vs 0: OR=76.68, p=2.67E-21

In IIBDGC
1 vs 0: OR=3.00, p=7.80E-169
2 vs 0: OR=30.76, p=2.55E-24

Key of the superior
performance of DL_known: The
off-diagonal hump in top-left

Almost all 3-variant carriers are in the top-left of the diagonal

FIG. 19A

| Variable | Relative importance | Scaled importance | Percentage | Rank | P Cedars | OR Cedars | P ibdgc | OR ibdgc | Beta delLange | P delLange | Beta Meta fixed B | P Meta fixed all | chr | pos_b g19 | Locus | Gene |
|---|---|---|---|---|---|---|---|---|---|---|---|---|---|---|---|---|
| rs11121129 | 0.472848982 | 0.472584898 | 1.39E-05 | 308 | 0.519716 | 0.981047 | 5.64E-06 | 0.938248 | -0.0632 | 0.0803 68 | -0.0512 2 | 1.53 E-08 | 1 | 8268095 | | ERRFI1 SLC45A1 |
| rs2769267 | 0.469662249 | 0.46966 225 | 1.38E-05 | 334 | 0.20861 53 | 0.96696 95 | 0.0002 01 | 0.9574 18 | -0.081 | 2.10E-05 | -0.0525 2 | 3.48 E-08 | 1 | 1.51E+08 | ? | RFX5 SELENBP1 |
| imm_1_2050216 64 | 0.502389 312 | 0.50238 931 | 1.48E-05 | 125 | 0.03238 71 | 1.08111 99 | 1.51E-13 | 1.08887 | 0.174 8 | 1.24E-14 | 0.1186 82 | 1.05 E-23 | 1 | 2.07E+08 | | IL10|IL19 |
| rs83165738 | 0.588133 633 | 0.58813 363 | 1.73E-05 | 32 | 0.42239 53 | 1.02236 8 | 7.80E-11 | 1.0767 98 | 0.094 3 | 1.84E-07 | 0.0742 39 | 4.94 E-16 | 2 | 24692 899 | | ITSN2 NCOA1 |
| rs7349418 | 0.541257 203 | 0.54125 72 | 1.60E-05 | 57 | 2.73E-05 | 1.1163 69 | 1.93E-13 | 1.0775 7 | 0.076 9 | 1.98E-06 | 0.0787 03 | 6.38 E-22 | 2 | 28843 080 | | BRE |
| imm_2_23308396 31 | 0.467102 259 | 0.46710 226 | 1.38E-05 | 376 | 0.1180 69 | 1.0483 46 | 1.04E-07 | 1.0646 | 0.126 9 | 4.02E-12 | 0.0780 95 | 1.02 E-22 | 2 | 2.31E+08 | ? | SP140 |
| rs11952467 | 0.599222 865 | 0.59922 287 | 1.50E-05 | 112 | 0.0664 62 | 0.8445 38 | 1.23E-05 | 0.9507 21 | -0.082 6 | 6.05E-12 | -0.0594 4 | 1.81 E-16 | 5 | 39912 624 | | LOC28563 4; LOC100132 944 |
| rs1842077 | 0.539467 996 | 0.53946 71 | 1.59E-05 | 59 | 0.0001 7 | 0.8954 35 | 2.65E-14 | 0.9174 04 | -0.126 3 | 1.11E-12 | -0.0990 5 | 9.36 E-28 | 5 | 40236 648 | | LOC28563 4; LOC100132 944 |
| rs1501908 | 0.463875 353 | 0.46387 535 | 1.37E-05 | 429 | 0.7809 6 | 1.00775 65 | 1.66E-05 | 1.0461 39 | 0.072 4 | 1.21E-05 | 0.0485 02 | 8.40 E-09 | 5 | 1.56E+08 | | TIM4D4 HAVCR1 |
| imm_5_1587466 94 | 0.485266 954 | 0.48526 695 | 1.43E-05 | 204 | 0.0185 84 | 1.0681 58 | 1.37E-22 | 1.1130 41 | 0.153 4 | 1.89E-19 | 0.1146 56 | 9.38 E-40 | 5 | 1.59E+08 | IL12B | IL12B ADRA1B |
| rs17034 | 0.459551 901 | 0.45955 19 | 1.35E-05 | 500 | 0.0572 39 | 1.0583 84 | 2.93E-06 | 1.0549 44 | 0.118 6 | 4.96E-11 | 0.0707 62 | 1.35 E-14 | 6 | 32796 521 | | TAP2 |
| imm_6_1065457 65 | 0.502486 408 | 0.50248 641 | 1.48E-05 | 124 | 8.41E-05 | 1.1190 08 | 1.83E-15 | 1.0921 6 | 0.125 4 | 2.89E-12 | 0.0997 78 | 8.78 E-29 | 6 | 1.06E+08 | ? | PREP1 PRDM1 |
| rs12718244 | 0.539295 52 | 0.53929 52 | 1.59E-05 | 60 | 0.6362 84 | 1.0123 75 | 1.27E-06 | 1.0514 47 | 0.049 9 | 0.0020 24 | 0.0465 75 | 2.04 E-08 | 7 | 50175 654 | | LOC10013 0988 |
| ccc8012660938 20CC0T | 0.505987 406 | 0.50598 741 | 1.49E-05 | 119 | 0.0004 88 | 0.9874 71 | 1.47E-06 | 0.9210 75 | -0.137 8 | 3.55E-14 | -0.0954 2 | 1.21 E-28 | 8 | 1.27E+08 | ? | TRIB1 LOC10013 0331 |
| imm_9_4978048 | 0.465799 063 | 0.46579 986 | 1.37E-05 | 393 | 0.0070 54 | 0.9263 11 | 8.89E-08 | 0.9442 23 | -0.135 3 | 4.37E-14 | -0.0778 6 | 6.04 E-19 | 9 | 49880 48 | JAK2 | LOC10013 8701; JAK2 |
| imm_9_5139657 | 0.460775 197 | 0.46077 52 | 1.36E-05 | 479 | 0.0286 46 | 1.0660 57 | 3.10E-13 | 1.0853 41 | 0.136 9 | 1.25E-14 | 0.0943 53 | 1.57 E-25 | 9 | 51496 57 | JAK2 | JAK2 INSL6 |
| rs10736978 | 0.571059 585 | 0.57105 958 | 1.68E-05 | 40 | 0.26662 49 | 0.9684 96 | 1.40E-05 | 0.9535 17 | 0.058 | 0.0006 27 | 0.0490 | 2.45 E-08 | 10 | 37782 50 | | PTFRM11 KLF6 |

FIG. 19B

| Variable | Relative importance | Scaled importance | Percentage | Rank | P Cedars | OR Cedars | P Ubdge | OR Ubdge | Beta deLange | P deLange | Beta Meta fixed n | P Meta fixed all | chr | pos_b g19 | Locus | Gene |
|---|---|---|---|---|---|---|---|---|---|---|---|---|---|---|---|---|
| imm_10_807124 81 | 0.478697 373 | 0.478269 737 | 1.39E-05 | 323 | 4.46E-05 | 0.88427 | 7.57E-15 | 0.91691 | -0.182 2 | 1.92E-17 | . | 3.55 E-32 | 10 | 81042 475 | ? | ZMIZ1 |
| imm_10_101266 715 | 0.510864 244 | 0.510886 434 | 1.30E-05 | 107 | 0.0085 7 | 0.92230 11 | 7.09E-17 | 0.91011 21 | 0.131 | 2.78E-13 | 0.1066 2 | 3.17 E-29 | 10 | 1.01E+08 | ? | GOT1 NKX2-3 |
| imm_11_759486 53 | 0.514449 077 | 0.514344 008 | 1.52E-05 | 98 | 0.1382 38 | 1.0411 55 | 1.34E-24 | 1.1141 | 0.167 1 | 2.82E-24 | 0.1072 17 | 7.60 E-44 | 11 | 76271 065 | C11orf0 | C11orf30 LRRC32 |
| X1kg_13_98847 881 | 0.478496 625 | 0.478049 662 | 1.39E-05 | 326 | 0.0804 57 | 0.9447 16 | 7.65E-08 | 0.9345 99 | 0.088 | 1.31E-05 | 0.0717 2 | 1.60 E-12 | 13 | 1E+08 | ? | UBAC2 TM9SF2 |
| imm_15_360938 78 | 0.466348 261 | 0.466634 826 | 1.37E-05 | 384 | 0.6165 28 | 1.0164 88 | 2.86E-08 | 1.0790 16 | 0.093 4 | 2.07E-06 | 0.0749 16 | 1.99 E-13 | 15 | 38908 586 | RASGR P1 | RASGRP1 LC15orf53 |
| imm_15_652334 | 0.539127 469 | 0.539912 787 | 1.59E-05 | 61 | 0.0240 92 | 1.0710 26 | 1.31E-12 | 1.0878 47 | 0.167 6 | 3.90E-19 | 0.1044 47 | 5.95 E-38 | 15 | 67448 363 | ? | SMAD3 |
| rs116411 04 | 0.601687 312 | 0.601658 787 | 1.77E-05 | 28 | 0.1008 52 | 1.0444 39 | 3.32E-12 | 1.0529 02 | 0.078 4 | 4.29E-19 | 0.0571 02 | 5.09 E-28 | 16 | 11704 651 | ? | LITAF SNN |
| rs1872691 | 0.491111 934 | 0.491111 193 | 1.35E-05 | 168 | 4.43E-05 | 0.8640 35 | 8.50E-10 | 0.9219 15 | -0.125 8 | 2.97E-09 | 0.0985 02 | 4.81 E-20 | 16 | 50350 210 | ? | ADCY7 |
| imm_16_493853 10 | 0.590577 96 | 0.590577 796 | 1.74E-05 | 39 | 3.45E-14 | 1.0690 04 | 1.22E-51 | 1.3850 52 | 0.651 4 | 1.06E-41 | 0.1892 87 | 3.25 E-35 | 16 | 50827 899 | NOD2 | CYLD |
| imm_16_845723 82 | 0.621049 047 | 0.621084 905 | 1.83E-05 | 20 | 0.0919 74 | 0.9598 52 | 4.38E-15 | 0.9398 | -0.105 4 | 2.19E-06 | 0.1000 6 | 2.25 E-20 | 16 | 86014 881 | ? | IRF8 LOC10013 1952 |
| rs1696781 4 | 0.468204 767 | 0.468230 477 | 1.38E-05 | 359 | 0.0185 73 | 1.0736 98 | 3.07E-05 | 1.0499 86 | 0.059 5 | 0.00899 38 | 0.0337 9 | 8.29 E-09 | 18 | 20070 591 | ? | CTAGE1 RBBP8 |
| X1kg_19_1057X 43 | 0.523841 573 | 0.523384 157 | 1.54E-05 | 82 | 1.10E-06 | 1.1558 32 | 1.27E-17 | 1.1049 | 0.168 8 | 3.73E-19 | 0.1234 9 | 4.96 E-38 | 19 | 11068 45 | ? | GPX4 SBNO2 |
| imm_19_103861 81 | 0.351278 71 | 0.351127 671 | 1.82E-05 | 53 | 1.39E-06 | 0.8633 96 | 5.36E-12 | 0.9934 99 | -0.147 | 4.98E-13 | 0.1090 1 | 3.98 E-26 | 19 | 10523 181 | TYK2 | CDC37 PDE4A |
| imm_20_616901 23 | 0.462340 295 | 0.462340 03 | 1.36E-05 | 450 | 0.8027 33 | 1.0081 14 | 4.74E-05 | 0.9478 95 | 0.092 4 | 2.41E-06 | 0.0580 3 | 2.03 E-08 | 20 | 62219 679 | TNFRS F6B | GMEB2 |
| imm_21_393907 08 | 0.516564 012 | 0.516566 401 | 1.52E-05 | 94 | 0.2730 72 | 0.9676 03 | 2.01E-06 | 0.9468 6 | 0.086 4 | 2.96E-06 | 0.0690 6 | 7.89 E-13 | 21 | 40468 838 | ? | FLJ45139 LOC39128 2 |

1

METHODS AND SYSTEMS FOR ASSESSING INFLAMMATORY DISEASE WITH DEEP LEARNING

CROSS-REFERENCE

This application claims the benefit of U.S. Provisional Patent Application No. 62/837,617, filed Apr. 23, 2019, and U.S. Provisional Patent Application No. 62/849,688, filed May 17, 2019, each of which is incorporated by reference herein in its entirety.

STATEMENT AS TO FEDERALLY SPONSORED RESEARCH

This invention was made with government support under Grant No. DK108140, DK046763, DK062413, DK046763, HS021747, and A1067068 awarded by the National Institutes of Health. The government has certain rights in the invention.

SUMMARY

Provided herein are methods and systems for assessing inflammatory disease or condition in subjects using Deep-Learning (DL) prediction models. The DL prediction models are applied to an inflammatory disease profile of a biological sample of a subject to identify a presence of the inflammatory disease or condition in the subject, or a likelihood that the subject will develop the inflammatory disease or condition. The inflammatory disease profile may comprise quantitative measures of a plurality of genomic loci containing, for example, genetic variants that are associated with the inflammatory disease.

Aspects disclosed herein provide methods for identifying an inflammatory disease or condition, such as an inflammatory bowel disease (IBD) in a subject, comprising: (a) assaying a biological sample of the subject to generate a dataset comprising genetic data; (b) processing the dataset at a plurality of genomic loci to determine quantitative measures of each genomic locus of the plurality of genomic loci, wherein the plurality of genomic loci comprises inflammatory disease-associated genes, thereby producing an inflammatory disease profile of the biological sample of the subject; and (c) applying a deep learning prediction model to the inflammatory disease profile to identify a presence of the inflammatory disease or condition in the subject, or a likelihood that the subject will develop the inflammatory disease or condition.

In some embodiments, the inflammatory disease or condition comprises an immune-mediated disease or condition. In some embodiments, the immune-mediated disease or condition comprises an inflammatory bowel disease (IBD). In some embodiments, the IBD is Crohn's disease (CD) or ulcerative colitis (UC). In some embodiments, the biological sample is selected from the group consisting of: a whole blood sample, a deoxyribonucleic acid (DNA) sample, a ribonucleic acid (RNA) sample, a cell-free sample, a tissue sample, a cell sample, and a derivative or fraction thereof. In some embodiments, assaying the biological sample comprises sequencing the biological sample to generate the dataset.

In some embodiments, the method further comprises identifying the presence of the inflammatory disease or condition in the subject, or the likelihood that the subject will develop the inflammatory disease or condition, at a sensitivity of at least about 70%. In some embodiments, the method further comprises identifying the presence of the inflammatory disease or condition in the subject, or the likelihood that the subject will develop the inflammatory disease or condition, at a sensitivity of at least about 80%. In some embodiments, the method further comprises identifying the presence of the inflammatory disease or condition in the subject, or the likelihood that the subject will develop the inflammatory disease or condition, at a sensitivity of at least about 90%. In some embodiments, the method further comprises identifying the presence of the inflammatory disease or condition in the subject, or the likelihood that the subject will develop the inflammatory disease or condition, at a sensitivity of at least about 95%. In some embodiments, the method further comprises identifying the presence of the inflammatory disease or condition in the subject, or the likelihood that the subject will develop the inflammatory disease or condition, at a sensitivity of at least about 99%. In some embodiments, the method further comprises identifying the presence of the inflammatory disease or condition in the subject, or the likelihood that the subject will develop the inflammatory disease or condition, at a specificity of at least about 70%. In some embodiments, the method further comprises identifying the presence of the inflammatory disease or condition in the subject, or the likelihood that the subject will develop the inflammatory disease or condition, at a specificity of at least about 80%. In some embodiments, the method further comprises identifying the presence of the inflammatory disease or condition in the subject, or the likelihood that the subject will develop the inflammatory disease or condition, at a specificity of at least about 90%. In some embodiments, the method further comprises identifying the presence of the inflammatory disease or condition in the subject, or the likelihood that the subject will develop the inflammatory disease or condition, at a specificity of at least about 95%. In some embodiments, the method further comprises identifying the presence of the inflammatory disease or condition in the subject, or the likelihood that the subject will develop the inflammatory disease or condition, at a specificity of at least about 99%.

In some embodiments, the method further comprises identifying the presence of the inflammatory disease or condition in the subject, or the likelihood that the subject will develop the inflammatory disease or condition, at a positive predictive value (PPV) of at least about 70%. In some embodiments, the method further comprises identifying the presence of the inflammatory disease or condition in the subject, or the likelihood that the subject will develop the inflammatory disease or condition, at a PPV of at least about 80%. In some embodiments, the method further comprises identifying the presence of the inflammatory disease or condition in the subject, or the likelihood that the subject will develop the inflammatory disease or condition, at a PPV of at least about 90%. In some embodiments, the method further comprises identifying the presence of the inflammatory disease or condition in the subject, or the likelihood that the subject will develop the inflammatory disease or condition, at a PPV of at least about 95%. In some embodiments, the method further comprises identifying the presence of the inflammatory disease or condition in the subject, or the likelihood that the subject will develop the inflammatory disease or condition, at a positive PPV of at least about 99%. In some embodiments, the method further comprises identifying the presence of the inflammatory disease or condition in the subject, or the likelihood that the subject will develop the inflammatory disease or condition, at a negative predictive value (NPV) of at least about 70%. In some embodiments, the method further comprises identifying the presence of the inflammatory disease or condition in the subject, or the likelihood that the subject will develop the inflammatory disease or condition, at a NPV of at least about 80%. In some embodiments, the method further comprises identifying the presence of the inflammatory disease or condition in the subject, or the likelihood that the subject will develop the inflammatory disease or condition, at a NPV of at least about 90%. In some embodiments, the method further comprises identifying the presence of the inflammatory disease or condition in the subject, or the likelihood that the subject will develop the inflammatory disease or condition, at a NPV of at least about 95%. In some embodiments, the method further comprises identifying the presence of the inflammatory disease or condition in the subject, or the likelihood that the subject will develop the inflammatory disease or condition, at a NPV of at least about 99%.

In some embodiments, the method further comprises identifying the presence of the inflammatory disease or condition in the subject, or the likelihood that the subject will develop the inflammatory disease or condition, with an Area Under Curve (AUC) of at least about 0.70. In some embodiments, the method further comprises identifying the presence of the inflammatory disease or condition in the subject, or the likelihood that the subject will develop the inflammatory disease or condition, with an AUC of at least about 0.80. In some embodiments, the method further comprises identifying the presence of the inflammatory disease or condition in the subject, or the likelihood that the subject will develop the inflammatory disease or condition, with an AUC of at least about 0.90. In some embodiments, the method further comprises identifying the presence of the inflammatory disease or condition in the subject, or the likelihood that the subject will develop the inflammatory disease or condition, with an AUC of at least about 0.95. In some embodiments, the method further comprises identifying the presence of the inflammatory disease or condition in the subject, or the likelihood that the subject will develop the inflammatory disease or condition, with an AUC of at least about 0.99.

In some embodiments, the subject is asymptomatic for one or more inflammatory disease or conditions, such as an IBD selected from the group consisting of: CD and UC. In some embodiments, the deep learning prediction model is trained using a first set of independent training samples associated with a presence of the inflammatory disease or condition and a second set of independent training samples associated with an absence of the inflammatory disease or condition. In some embodiments, the method further comprises applying the deep learning prediction model (e.g., a deep learning classifier) to a set of clinical health data of the subject. In some embodiments, the set of clinical health data comprises one or more of familial history of an inflammatory disease or disorder, age, hypertension or pre-hypertension, diabetes or pre-diabetes, overweight or obesity, environmental exposure, lifestyle risk factors (e.g., smoking, alcohol consumption, or drug use), or presence of other risk factors. In some embodiments, the deep learning prediction model comprises a deep learning algorithm, a neural network, a Random Forest, an XGBoost, a Gradient Boost, or a combination thereof. In some embodiments, the deep learning prediction model comprises a deep learning algorithm. In some embodiments, the deep learning algorithm comprises a deep neural network. In some embodiments, the deep neural network comprises a convolutional neural network (CNN). In some embodiments, the method further comprises optimizing a set of hyperparameters of the CNN. In some embodiments, optimizing the set of hyperparameters comprises performing an intensive grid search. In some embodiments, the set of hyperparameters comprises a number of layers and/or a number of neurons of the CNN. In some embodiments, the CNN comprises a combination of a plurality of CNNs. In some embodiments, the plurality of CNNs comprises two CNNs.

In some embodiments, (a) comprises (i) subjecting the biological sample to conditions that are sufficient to isolate, enrich, or extract a plurality of DNA molecules; and (ii) analyzing the plurality of DNA molecules to generate the dataset. In some embodiments, the plurality of genomic loci comprises at least about 1,000 distinct genomic loci. In some embodiments, the plurality of genomic loci comprises at least about 10,000 distinct genomic loci. In some embodiments, the plurality of genomic loci comprises at least about 100,000 distinct genomic loci.

In some embodiments, the method further comprises identifying the likelihood that the subject will develop the inflammatory disease or condition. In some embodiments, the method further comprises providing a therapeutic intervention for the inflammatory disease or condition of the subject, provided the presence of the inflammatory disease or condition is identified in the subject. In some embodiments, the method further comprises monitoring the inflammatory disease or condition of the subject by assessing the inflammatory disease or condition in the subject at a plurality of time points, wherein the assessing is based at least partially on identifying the presence of the inflammatory disease or condition in (c) at one or more time points of the plurality of time points. In some embodiments, a difference between two or more assessments of the inflammatory disease or condition in the subject at two or more time points of the plurality of time points is indicative of one or more of: (i) a diagnosis of the inflammatory disease or condition of the subject, (ii) a prognosis of the inflammatory disease or condition of the subject, or (iii) an efficacy or non-efficacy of a course of treatment for treating the inflammatory disease or condition of the subject.

Aspects disclosed herein provide computer systems for identifying an inflammatory disease such as an inflammatory bowel disease (IBD) condition in a subject, comprising: (a) a database that is configured to store a dataset comprising genetic data, wherein the genetic data is obtained by assaying a biological sample of the subject; and (b) one or more computer processors operatively coupled to the database, wherein the one or more computer processors are individually or collectively programmed to: (i) process the dataset at a plurality of genomic loci to determine quantitative measures of each genomic locus of the plurality of genomic loci, wherein the plurality of genomic loci comprises inflammatory disease-associated genes, thereby producing an inflammatory disease profile of the biological sample of the subject; and (ii) apply a deep learning prediction model to the inflammatory disease profile to identify a presence of the inflammatory disease or condition in the subject, or a likelihood that the subject will develop the inflammatory disease or condition.

In some embodiments, the inflammatory disease or condition comprises an immune-mediated disease or condition. In some embodiments, the immune-mediated disease or condition comprises an IBD. In some embodiments, the IBD is CD or UC. In some embodiments, the biological sample is selected from the group consisting of: a whole blood sample, a DNA sample, a RNA sample, a cell-free sample, a tissue sample, a cell sample, and a derivative or fraction thereof. In some embodiments, assaying the biological sample comprises sequencing the biological sample to generate the dataset.

In some embodiments, the one or more computer processors are individually or collectively programmed to further identify the presence of the inflammatory disease or condition in the subject, or the likelihood that the subject will develop the inflammatory disease or condition, at a sensitivity of at least about 70%. In some embodiments, the one or more computer processors are individually or collectively programmed to further identify the presence of the inflammatory disease or condition in the subject, or the likelihood that the subject will develop the inflammatory disease or condition, at a sensitivity of at least about 80%. In some embodiments, the one or more computer processors are individually or collectively programmed to further identify the presence of the inflammatory disease or condition in the subject, or the likelihood that the subject will develop the inflammatory disease or condition, at a sensitivity of at least about 90%. In some embodiments, the one or more computer processors are individually or collectively programmed to further identify the presence of the inflammatory disease or condition in the subject, or the likelihood that the subject will develop the inflammatory disease or condition, at a sensitivity of at least about 95%. In some embodiments, the one or more computer processors are individually or collectively programmed to further identify the presence of the inflammatory disease or condition in the subject, or the likelihood that the subject will develop the inflammatory disease or condition, at a sensitivity of at least about 99%. In some embodiments, the one or more computer processors are individually or collectively programmed to further identify the presence of the inflammatory disease or condition in the subject, or the likelihood that the subject will develop the inflammatory disease or condition, at a specificity of at least about 70%. In some embodiments, the one or more computer processors are individually or collectively programmed to further identify the presence of the inflammatory disease or condition in the subject, or the likelihood that the subject will develop the inflammatory disease or condition, at a specificity of at least about 80%. In some embodiments, the one or more computer processors are individually or collectively programmed to further identify the presence of the inflammatory disease or condition in the subject, or the likelihood that the subject will develop the inflammatory disease or condition, at a specificity of at least about 90%. In some embodiments, the one or more computer processors are individually or collectively programmed to further identify the presence of the inflammatory disease or condition in the subject, or the likelihood that the subject will develop the inflammatory disease or condition, at a specificity of at least about 95%. In some embodiments, the one or more computer processors are individually or collectively programmed to further identify the presence of the inflammatory disease or condition in the subject, or the likelihood that the subject will develop the inflammatory disease or condition, at a specificity of at least about 99%.

In some embodiments, the one or more computer processors are individually or collectively programmed to further identify the presence of the inflammatory disease or condition in the subject, or the likelihood that the subject will develop the inflammatory disease or condition, at a PPV of at least about 70%. In some embodiments, the one or more computer processors are individually or collectively programmed to further identify the presence of the inflammatory disease or condition in the subject, or the likelihood that the subject will develop the inflammatory disease or condition, at a PPV of at least about 80%. In some embodiments, the one or more computer processors are individually or collectively programmed to further identify the presence of the inflammatory disease or condition in the subject, or the likelihood that the subject will develop the inflammatory disease or condition, at a PPV of at least about 90%. In some embodiments, the one or more computer processors are individually or collectively programmed to further identify the presence of the inflammatory disease or condition in the subject, or the likelihood that the subject will develop the inflammatory disease or condition, at a PPV of at least about 95%. In some embodiments, the one or more computer processors are individually or collectively programmed to further identify the presence of the inflammatory disease or condition in the subject, or the likelihood that the subject will develop the inflammatory disease or condition, at a PPV of at least about 99%. In some embodiments, the one or more computer processors are individually or collectively programmed to further identify the presence of the inflammatory disease or condition in the subject, or the likelihood that the subject will develop the inflammatory disease or condition, at a negative predictive value (NPV) of at least about 70%. In some embodiments, the one or more computer processors are individually or collectively programmed to further identify the presence of the inflammatory disease or condition in the subject, or the likelihood that the subject will develop the inflammatory disease or condition, at a NPV of at least about 80%. In some embodiments, the one or more computer processors are individually or collectively programmed to further identify the presence of the inflammatory disease or condition in the subject, or the likelihood that the subject will develop the inflammatory disease or condition, at a NPV of at least about 90%. In some embodiments, the one or more computer processors are individually or collectively programmed to further identify the presence of the inflammatory disease or condition in the subject, or the likelihood that the subject will develop the inflammatory disease or condition, at a NPV of at least about 95%. In some embodiments, the one or more computer processors are individually or collectively programmed to further identify the presence of the inflammatory disease or condition in the subject, or the likelihood that the subject will develop the inflammatory disease or condition, at a NPV of at least about 99%.

In some embodiments, the one or more computer processors are individually or collectively programmed to further identify the presence of the inflammatory disease or condition in the subject, or the likelihood that the subject will develop the inflammatory disease or condition, with an Area Under Curve (AUC) of at least about 0.70. In some embodiments, the one or more computer processors are individually or collectively programmed to further identify the presence of the inflammatory disease or condition in the subject, or the likelihood that the subject will develop the inflammatory disease or condition, with an AUC of at least about 0.80. In some embodiments, the one or more computer processors are individually or collectively programmed to further identify the presence of the inflammatory disease or condition in the subject, or the likelihood that the subject will develop the inflammatory disease or condition, with an AUC of at least about 0.90. In some embodiments, the one or more computer processors are individually or collectively programmed to further identify the presence of the inflammatory disease or condition in the subject, or the likelihood that the subject will develop the inflammatory disease or condition, with an AUC of at least about 0.95. In some embodiments, the one or more computer processors are individually or collectively programmed to further identify the presence of the inflammatory disease or condition in the subject, or the likelihood that the subject will develop the inflammatory disease or condition, with an AUC of at least about 0.99.

In some embodiments, the subject is asymptomatic for one or more inflammatory disease or conditions, such as an IBD comprising CD or UC. In some embodiments, the deep learning prediction model is trained using a first set of independent training samples associated with a presence of the inflammatory disease or condition and a second set of independent training samples associated with an absence of the inflammatory disease or condition. In some embodiments, the one or more computer processors are individually or collectively further programmed to apply the deep learning prediction model (e.g., a deep learning classifier) to a set of clinical health data of the subject. In some embodiments, the set of clinical health data comprises one or more of familial history of an inflammatory disease or disorder, age, hypertension or pre-hypertension, diabetes or pre-diabetes, overweight or obesity, environmental exposure, lifestyle risk factors (e.g., smoking, alcohol consumption, or drug use), or presence of other risk factors. In some embodiments, the deep learning prediction model comprises a deep learning algorithm, a neural network, a Random Forest, an XGBoost, or a Gradient Boost. In some embodiments, the deep learning prediction model comprises a deep learning algorithm. In some embodiments, the deep learning algorithm comprises a deep neural network. In some embodiments, the deep neural network comprises a convolutional neural network (CNN). In some embodiments, the one or more computer processors are individually or collectively programmed to further optimize a set of hyperparameters of the CNN. In some embodiments, optimizing the set of hyperparameters comprises performing an intensive grid search. In some embodiments, the set of hyperparameters comprises a number of layers and/or a number of neurons of the CNN. In some embodiments, the CNN comprises a combination of a plurality of CNNs. In some embodiments, the plurality of CNNs comprises two CNNs.

In some embodiments, assaying the biological sample comprises subjecting the biological sample to conditions that are sufficient to isolate, enrich, or extract a plurality of DNA molecules; and analyzing the plurality of DNA molecules to generate the dataset. In some embodiments, the plurality of genomic loci comprises at least about 1,000 distinct genomic loci. In some embodiments, the plurality of genomic loci comprises at least about 10,000 distinct genomic loci. In some embodiments, the plurality of genomic loci comprises at least about 100,000 distinct genomic loci.

In some embodiments, the one or more computer processors are individually or collectively programmed to further identify the likelihood that the subject will develop the inflammatory disease or condition. In some embodiments, the one or more computer processors are individually or collectively programmed to further provide a therapeutic intervention for the inflammatory disease or condition, provided the presence of the inflammatory disease or condition is identified in the subject. In some embodiments, the one or more computer processors are individually or collectively programmed to further monitor the inflammatory disease or condition in the subject by assessing the inflammatory disease or condition of the subject at a plurality of time points, wherein the assessing is based at least partially on identifying the presence of the inflammatory disease or condition in (ii) by the one or more computer processors at one or more time points of the plurality of time points. In some embodiments, a difference between two or more assessments of the inflammatory disease or condition in the subject at two or more time points of the plurality of time points is indicative of one or more of: (i) a diagnosis of the inflammatory disease or condition of the subject, (ii) a prognosis of the inflammatory disease or condition of the subject, and (iii) an efficacy or non-efficacy of a course of treatment for treating the inflammatory disease or condition of the subject.

In some embodiments, the system further comprises an electronic display operatively coupled to the one or more computer processors, wherein the electronic display comprises a graphical user interface that is configured to display the report.

Aspects disclosed herein provide non-transitory computer-readable media comprising machine-executable code that, upon execution by one or more computer processors, implements a method for identifying an inflammatory disease such as an IBD of a subject, the method comprising: (a) assaying a biological sample of the subject to generate a dataset comprising genetic data; (b) processing the dataset at a plurality of genomic loci to determine quantitative measures of each of the plurality of genomic loci, wherein the plurality of genomic loci comprises inflammatory disease-associated genes, thereby producing an inflammatory disease profile of the biological sample of the subject; and (c) applying a deep learning prediction model to the inflammatory disease profile to identify a presence of the inflammatory disease or condition in the subject, or a risk that the subject will develop the inflammatory disease or condition.

Aspects disclosed herein provide non-transitory computer-readable media comprising machine-executable code that, upon execution by one or more computer processors, implements any of the methods above or elsewhere herein.

Aspects disclosed herein provide systems comprising one or more computer processors and computer memory coupled thereto. The computer memory comprises machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2 shows a non-limiting example of prediction performance of different approaches to profile inflammatory bowel disease (IBD) via deep learning approaches, using the methods and systems disclosed herein. This figure includes receiver operating characteristic (ROC) curves of different polygenic risk scores obtained using the methods and systems disclosed herein. The legend is as follows—AUC: Area Under the Curve; DL_known: Deep Learning model using known susceptibility variants and variants in LD with susceptibility variants; DL_others: Deep Learning model using the other variants (e.g., excluding known susceptibility variants and variants in LD with these susceptibility variants) on ImmunoChip™; DL_comb: Deep Learning model combining DL-known and DL-others.

FIG. 8 shows a non-limiting example of PRS (e.g., constructed using LDPred) being used to identify risk comparable to monogenic mutations.

FIG. 11 shows a non-limiting example of activation functions (e.g., fixed mathematical operations) that may be used in DeepLearning algorithms, such as sigmoid, tanh, ReLU, leaky ReLU, maxout, and ELU, using the methods and systems disclosed herein.

FIG. 13 shows a non-limiting example of DL score and association with serologies (within cases), using the methods and systems disclosed herein.

FIG. 15 shows a non-limiting example of data results that indicate deviations from a linear additive model, using the methods and systems disclosed herein.

FIG. 19A-19B show 32 independent genome-wide signals were identified with a meta-analysis p-value of $5.0 \times 10^{-8}$ using the LD model described herein.

DETAILED DESCRIPTION

Figure 1:
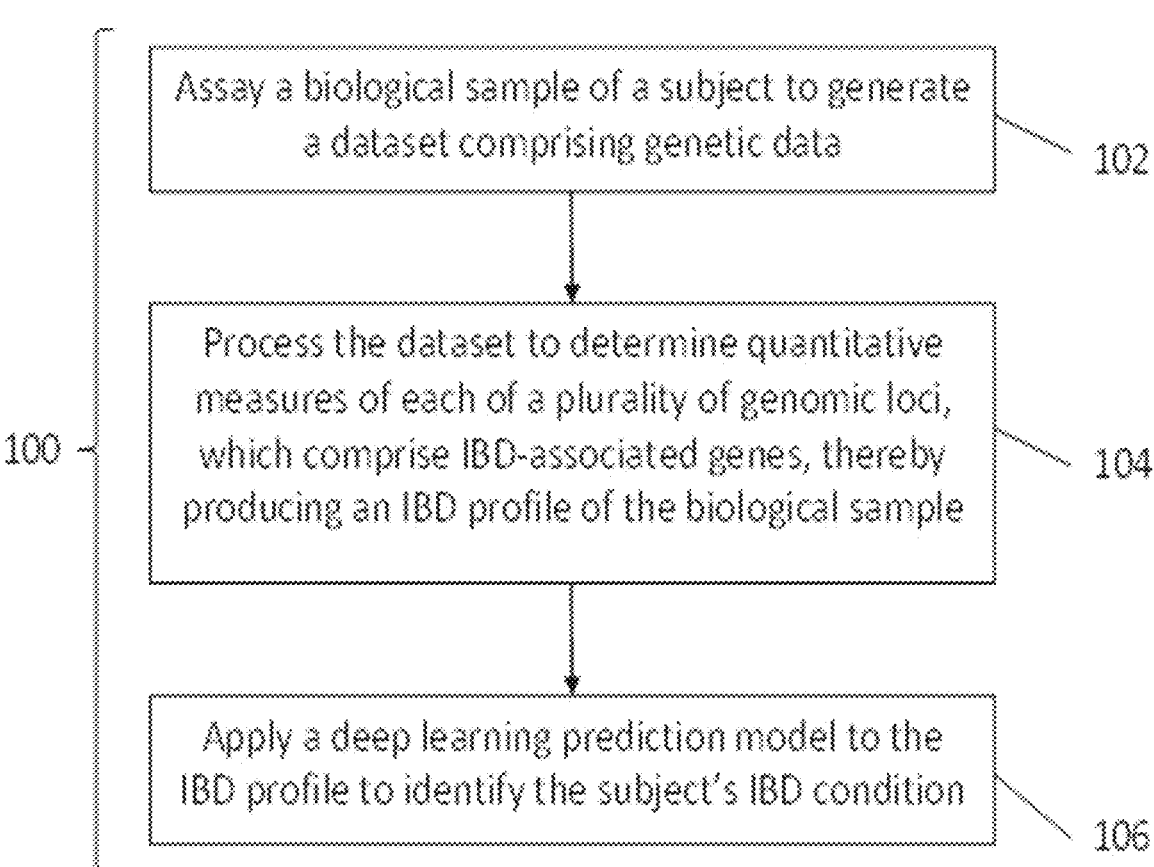
FIG. 1 shows a non-limiting example of a workflow to profile inflammatory bowel disease (IBD) conditions via deep learning approaches, using the methods and systems disclosed herein.

Inflammatory diseases, such as inflammatory bowel disease (IBD) is a gastrointestinal immune-mediated disease with a significant effect on morbidity and quality of life. Crohn disease (CD), a subtype of IBD, affects over one-half of a million people in the United States alone. The significant effect on morbidity is, in part, due to limitations of existing diagnostic and prognostic tests that fail to identify patients suffering from inflammatory diseases early enough in disease progression to prevent worsening of the disease or development of complications, such as stricturing or penetrating disease phenotypes.

Delay in disease diagnosis or prognosis is a major clinical problem. Early therapeutic intervention of inflammatory diseases in patients at high risk for developing severe forms of the disease may lead to lower risk of tissue damage in the affected area (e.g., bowel), significantly improved disease remission, fewer disease complications, and a reduced need for surgery. For many patients suffering from inflammatory disease, early therapeutic intervention is associated with a higher response to prescribed medication to treat the disease. Early therapeutic interventions include, but are not limited to, active agents that modulate the gut microbiome or targeted (e.g., biologic therapies).

There have been recent efforts to predict complex disease risk using genetic data with the LDpred approach, a Python based software package that adjusts genome-wide association study (GWAS) summary statistics for the effects of linkage disequilibrium (LD) and, in some cases, incorporates variants that have not reached a genome-wide significance threshold. However, the LDpred approach may suffer at least from the following drawbacks. The LDpred approach may not perform stringent quality control procedures to prune the input datasets, which may adversely affect the performance. The LDpred approach may not make use of convolutional neural networks, which automatically include two data pre-processing layers (Convolutional Layer and Pooling Layer) that perform much of the computational heavy lifting before the fully-connected layers. The LDpred approach may comprise a manual single nucleotide polymorphism (SNP) preselection step based on single-SNP level statistics may be performed to reduce the dimension of data, which may potentially lead to loss of information. The LDpred approach may not comprise intensive tuning of a set of hyperparameters which may have important impact on performance of the models. The LDpred approach may not use a superlearner that is constructed by combining the two separately trained models. The LDpred approach may fail to account for non-linear effects among known variants.

Provided herein are systems and methods that apply deep learning approaches to predict complex disease risk. The deep learning approaches described herein analyze genetic data of a subject to identify the subject as being at high risk of having, or developing, an inflammatory disease (e.g., CD). The deep learning approaches described herein utilize prediction tools from a broader family of machine learning methods with proven records in prediction performance. The present disclosure provides a comparison between the performance of the deep learning and LDpred approaches to show the superior clinical utility (e.g., for clinical decision-making or assessment) of the deep learning approach described herein.

Provided herein are methods and systems for predicting that a subject has, or will develop, an inflammatory disease, such as CD using a DeepLearning (DL) model. The DL model is useful for the diagnosis, prognosis, monitoring, treatment, or prevention of an inflammatory disease described herein. The DL model is useful for identifying a subject at a high risk for developing a severe form of the inflammatory disease described herein, including complications (e.g., stricturing, penetrating, or medically refractory disease phenotypes). The DL model is useful for monitoring a course of treatment of a subject to optimize or tailor a therapeutic intervention to a particular subject.

In contrast to LDpred approach, the DL model described herein perform stringent quality control procedures to prune the input datasets. The DL model described herein also utilize convolutional neural networks that do not require a preselection SNP and are capable of accounting for non-linear effects of genetic variants. All of the above, in combination with intensive tuning of the hyperparameters of the deep learning algorithms utilized in the DL model described herein, ensure a more accurate and more efficient prediction, as compared to the predictions generated using LDpred.

Using methods and systems of the present disclosure, the DL model employs deep learning algorithms to analyze genetic data of a subject. Such deep learning algorithms significantly boost prediction accuracy and associate the predicted risk for disease with disease clinical characteristics. The clinical utility of the methods and systems of the present disclosure is underscored by the ability of the DL model to analyze large-scale genomic data, such as next-generation sequencing (NGS) data, to predict a wide range of inflammatory diseases. The DL model described herein applied to large-scale genomic data may translate into clinical practice, by aiding medical practitioners in providing individualized therapeutic strategies for the treatment of complex disease, such as the inflammatory diseases described herein (e.g., CD).

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms may include quantitative, qualitative or quantitative and qualitative determinations. Assessing may be relative or absolute. "Detecting the presence of" may include determining the amount of something present in addition to determining whether it is present or absent depending on the context.

The terms "subject," or "individual," are often used interchangeably herein. A "subject" may be a biological entity containing expressed genetic materials. The biological entity may be a plant, animal, or microorganism, including, for example, bacteria, viruses, fungi, and protozoa. The subject may be tissues, cells and their progeny of a biological entity obtained in vivo or cultured in vitro. The subject may be a mammal. The mammal may be a human. The subject may be diagnosed or suspected of being at elevated or high risk for an inflammatory disease. A subject diagnosed with an inflammatory disease or condition disclosed herein may be referred to as a "patient." In some cases, the subject is not necessarily diagnosed or suspected of being at high risk for the inflammatory disease. The subject may be displaying a symptom(s) indicative of a health or physiological state or condition of the subject, such as an inflammatory disease or disorder (e.g., an IBD such as CD) of the subject. As an alternative, the subject may be asymptomatic with respect to such health or physiological state or condition. For example, the subject may be asymptomatic with respect to an inflammatory disease or condition, characterized by an absence of symptoms associated with the inflammatory disease or condition (e.g., inflammation, heat, pain, redness, swelling, and loss of function).

A "genetic variant" as used herein refers to an aberration in a nucleic acid sequence, as compared to the nucleic acid sequence in a reference population. In some cases, the aberration is a polymorphism, such as a single nucleotide polymorphism or an indel.

As used herein, the term, "single nucleotide polymorphism" or "SNP," refers to a variation in a single nucleotide within a polynucleotide sequence. The term should not be interpreted as placing a restriction on a frequency of the SNP in a given population. The variation of an SNP may have multiple different forms. A single form of an SNP is referred to as an "allele." An SNP can be mono-, bi-, tri-, or tetra-allelic.

The term, "indel," as disclosed herein, refers to an insertion, or a deletion, of a nucleobase within a polynucleotide sequence.

As used herein, the term "inflammatory disease" refers to a disease, disorder, or other abnormal condition of a subject that is characterized by inflammation. The inflammatory disease may be an immune system response (e.g., in response to an injury or infection) in a subject, which may be characterized by a combination of one or more symptoms in the subject, including heat, pain, redness, swelling, and loss of function. The inflammatory disease may be acute inflammation, chronic inflammation, and/or systemic inflammation. The inflammatory disease may be a subclinical or clinical phenotype of an inflammatory bowel disease, such as fibrosis, stricturing disease, penetrating disease, or a combination thereof. The inflammatory disease may be characterized as a severe form of the disease. The inflammatory disease may be medically refractory.

The term "inflammatory bowel disease" or "IBD" as used herein refers to diseases or disorders of the gastrointestinal tract. Non-limiting examples of IBD include, Crohn's disease (CD), ulcerative colitis (UC), indeterminate colitis (IC), microscopic colitis, diversion colitis, Behcet's disease, and other inconclusive forms of IBD. In some instances, IBD comprises fibrosis, fibrostenosis, stricturing and/or penetrating disease, obstructive disease, or a disease that is medically refractory (e.g., mrUC, refractory CD), perianal CD, or other complicated forms of IBD.

"Linkage disequilibrium," or "LD," as used herein refers to the non-random association of alleles or indels in different gene loci in a given population. LD may be defined by a D' value corresponding to the difference between an observed and expected allele or indel frequencies in the population (D=Pab−PaPb), which is scaled by the theoretical maximum value of D. LD may be defined by an r2 value corresponding to the difference between an observed and expected unit of risk frequencies in the population (D=Pab−PaPb), which is scaled by the individual frequencies of the different loci.

As used herein, the term "medically refractory" refers to a disease, disorder, or other abnormal condition of a subject that is non-responsive to a standard therapy, such as an anti-inflammatory drug or immunomodulator. The immunomodulator may be anti-tumor necrosis factor alpha (TNFα) therapy. Non-limiting examples of standard therapy include glucocorticosteriods, anti-TNF therapy, anti-a4-b7 therapy (vedolizumab), anti-IL12p40 therapy (ustekinumab), Thalidomide, and Cytoxin.

The term "serological marker," as used herein refers to a type of biomarker representing an antigenic response in a subject that may be detected in the serum of the subject. Non-limiting examples of a serological marker comprise anti-*Saccharomyces cerevisiae* antibody (ASCA), an anti-neutrophil cytoplasmic antibody (ANCA), *E. coli* outer membrane porin protein C (OmpC), anit-I2 antibody, and anti-Cbir1 flagellin antibody.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit may be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of an inflammatory disease or condition, delaying or eliminating the onset of symptoms of an inflammatory disease or condition, slowing, halting, or reversing the progression of an inflammatory disease or condition, or any combination thereof. For prophylactic benefit, a subject at risk of developing a particular inflammatory disease, or to a subject reporting one or more of the physiological symptoms of an inflammatory disease may undergo treatment, even though a diagnosis of this inflammatory disease may not have been made.

As used herein the term "diagnose" or "diagnosis" of a status or outcome includes predicting or diagnosing the status or outcome, determining predisposition to a status or outcome, monitoring treatment of patient, diagnosing a therapeutic response of a patient, and prognosis of status or outcome, progression, and response to particular treatment.

As used herein, the term "biological sample," generally refers to a biological sample obtained from or derived from one or more subjects from which nucleic acids may be obtained. Non-limiting examples of a "biological sample" include whole blood, peripheral blood, plasma, serum, saliva, mucus, urine, semen, lymph, fecal extract, cheek swab, cells or other bodily fluid or tissue, including but not limited to tissue obtained through surgical biopsy or surgical resection. The sample may comprise tissue from the large and/or small intestine. The large intestine sample may comprise the cecum, colon (the ascending colon, the transverse colon, the descending colon, and the sigmoid colon), rectum and/or the anal canal. The small intestine sample may comprise the duodenum, jejunum, and/or the ileum. Alternatively, a biological sample can be obtained through primary patient derived cell lines, or archived patient samples in the form of preserved samples, or fresh frozen samples. The biological sample may be a deoxyribonucleic acid (DNA) sample or a ribonucleic acid (RNA) sample, which refers to any biological sample above containing DNA and/or RNA that has been at least partially purified and/or isolated.

The term "derived from" used herein refers to an origin or source, and may include naturally occurring, recombinant, unpurified, or purified molecules.

To obtain a blood sample, various techniques may be used, e.g., a syringe or other vacuum suction device. A blood sample may be optionally pre-treated or processed prior to use. A sample, such as a blood sample, may be analyzed under any of the methods and systems herein within 4 weeks, 2 weeks, 1 week, 6 days, 5 days, 4 days, 3 days, 2 days, 1 day, 12 hr, 6 hr, 3 hr, 2 hr, or 1 hr from the time the sample is obtained, or longer if frozen. When obtaining a sample from a subject (e.g., blood sample), the amount may vary depending upon subject size and the condition being screened. In some embodiments, at least 10 mL, 5 mL, 1 mL, 0.5 mL, 250, 200, 150, 100, 50, 40, 30, 20, 10, 9, 8, 7, 6, 5, 4, 3, 2, or 1 μL of a sample is obtained. In some embodiments, 1-50, 2-40, 3-30, or 4-20 μL of sample is obtained. In some embodiments, more than 5, 10, 15, 20, 25, 30, 35, 40, 45, 50, 55, 60, 65, 70, 75, 80, 85, 90, 95 or 100 μL of a sample is obtained.

The sample may be taken before and/or after treatment of a subject with an inflammatory disease or disorder. Samples may be obtained from a subject during a treatment or a treatment regime. Multiple samples may be obtained from a subject to monitor the effects of the treatment over time. The sample may be taken from a subject known or suspected of having an inflammatory disease or disorder for which a definitive positive or negative diagnosis is not available via clinical tests. The sample may be taken from a subject suspected of having an inflammatory disease or disorder. The sample may be taken from a subject experiencing unexplained symptoms, such as fatigue, nausea, weight loss, aches and pains, weakness, or bleeding. The sample may be taken from a subject having explained symptoms. The sample may be taken from a subject at risk of developing an inflammatory disease or disorder due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

In some embodiments, a sample may be taken at a first time point and assayed, and then another sample may be taken at a subsequent time point and assayed. Such methods may be used, for example, for longitudinal monitoring purposes to track the development or progression of an inflammatory disease. In some embodiments, the progression of an inflammatory disease may be tracked before treatment, after treatment, or during the course of treatment, to determine the treatment's effectiveness. For example, a method as described herein may be performed on a subject prior to, and after, treatment of a subject with an inflammatory disease therapy to measure the subject's disease progression or regression in response to the inflammatory disease therapy.

After obtaining a sample from the subject, the sample may be processed to generate datasets indicative of an inflammatory disease or disorder of the subject. For example, a presence, absence, or quantitative assessment of nucleic acid molecules of the sample at a panel of inflammatory disease-associated genomic loci may be indicative of an inflammatory disease of the subject. For example, the inflammatory disease-associated genomic loci may have been shown to be correlated with presence or risk of an inflammatory disease (e.g., as shown through GWAS statistics). The nucleic acid molecules may comprise ribonucleic acid (RNA) or deoxyribonucleic acid (DNA). Processing the sample obtained from the subject may comprise (i) subjecting the sample to conditions that are sufficient to isolate, enrich, or extract a plurality of nucleic acid molecules (e.g., DNA or RNA), and (ii) assaying the plurality of nucleic acid molecules (e.g., DNA or RNA) to generate the dataset (e.g., microarray data, nucleic acid sequences, or quantitative polymerase chain reaction (qPCR) data). Methods of assaying may include any assay known in the art or described in the literature, for example, a microarray assay, a sequencing assay (e.g., DNA sequencing, RNA sequencing, or RNA-Seq), or a quantitative polymerase chain reaction (qPCR) assay.

As used herein, the term "nucleic acid" generally refers to a polymeric form of nucleotides of any length, either deoxy-ribonucleotides (dNTPs) or ribonucleotides (rNTPs), or analogs thereof. Nucleic acids may have any three-dimensional structure, and may perform any function, known or unknown. Non-limiting examples of nucleic acids include deoxyribonucleic (DNA), ribonucleic acid (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a reporter agent.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogs thereof. As used herein, a "target ribonucleic acid (RNA)" generally refers to a target nucleic acid that is RNA. As used herein, a "target deoxyribonucleic acid (DNA)" generally refers to a target nucleic acid that is DNA.

As used herein, the terms "amplifying" and "amplification" generally refer to increasing the size or quantity of a nucleic acid molecule. The nucleic acid molecule may be single-stranded or double-stranded. Amplification may include generating one or more copies or "amplified product" of the nucleic acid molecule. Amplification may be performed, for example, by extension (e.g., primer extension) or ligation. Amplification may include performing a primer extension reaction to generate a strand complementary to a single-stranded nucleic acid molecule, and in some cases generate one or more copies of the strand and/or the single-stranded nucleic acid molecule. The term "DNA amplification" generally refers to generating one or more copies of a DNA molecule or "amplified DNA product." The term "reverse transcription amplification" generally refers to the generation of deoxyribonucleic acid (DNA) from a ribonucleic acid (RNA) template via the action of a reverse transcriptase.

The term "cell-free nucleic acid (cfNA)", as used herein, generally refers to nucleic acids (such as cell-free RNA ("cfRNA") or cell-free DNA ("cfDNA")) in a biological sample that are not contained in a cell. cfDNA may circulate freely in in a bodily fluid, such as in the bloodstream.

The term "cell-free sample", as used herein, generally refers to a biological sample that is substantially devoid of intact cells. This may be derived from a biological sample that is itself substantially devoid of cells or may be derived from a sample from which cells have been removed. Examples of cell-free samples include those derived from blood, such as serum or plasma; urine; or samples derived from other sources, such as semen, sputum, feces, ductal exudate, lymph, or recovered lavage.

The term "genomic region" or "genomic locus", as used interchangeably herein, generally refers to identified regions of nucleic acid that are identified by their location in the chromosome. In some examples, the genomic regions are referred to by a gene name and encompass coding and non-coding regions associated with that physical region of nucleic acid. As used herein, a gene comprises coding regions (exons), non-coding regions (introns), transcriptional control or other regulatory regions, and promoters. In another example, the genomic region may incorporate an intron or exon or an intron/exon boundary within a named gene.

The term "confidence interval" or "CI", as used interchangeably herein, generally refers to a range of values which contains an unknown parameter (e.g., mean) of a set of observations with a given level of confidence or certainty. For example, a 95% CI may refer to a range of values which contains the true mean of a set of observations with a 95% confidence.

The section headings used herein are for organizational purposes only and are not to be construed as limiting the subject matter described.

II. METHODS

FIG. 1 shows a non-limiting example of a workflow to profile inflammatory disease (e.g., IBD) conditions via deep learning approaches, using the methods and systems disclosed herein. In an aspect, the present disclosure provides a method 100 for identifying an inflammatory disease (e.g., IBD) condition of a subject, comprising: assaying a biological sample of the subject to generate a dataset comprising genetic data (as in step 102); processing the dataset at a plurality of genomic loci to determine quantitative measures of each of the genomic loci, wherein the plurality of genomic loci comprises inflammatory disease-associated genes, thereby producing an inflammatory disease profile of the biological sample of the subject (as in step 104); and applying a deep learning prediction model to the inflammatory disease profile to identify the inflammatory disease or condition of the subject (as in step 106). For example, the inflammatory disease profile may comprise a plurality of quantitative measures of each of a plurality of inflammatory disease-associated genomic loci and/or a set of clinical health data of the subject. In some embodiments, the set of clinical health data comprises one or more of familial history of an inflammatory disease or disorder, age, hypertension or pre-hypertension, diabetes or pre-diabetes, overweight or obesity, environmental exposure, lifestyle risk factors (e.g., smoking, alcohol consumption, or drug use), or presence of other risk factors.

The biological samples may be obtained or derived from a human subject (e.g., a subject having or suspected of having an inflammatory disease or disorder). The biological samples may be stored in a variety of storage conditions before processing, such as different temperatures (e.g., at room temperature, under refrigeration or freezer conditions, at 25° C., at 4° C., at −18° C., −20° C., or at −80° C.) or different suspensions (e.g., EDTA collection tubes, RNA collection tubes, or DNA collection tubes).

The biological sample may be obtained from a subject with an inflammatory disease, disorder, or condition, from a subject that is suspected of having an inflammatory disease, disorder, or condition, or from a subject that does not have or is not suspected of having the inflammatory disease, disorder, or condition.

The inflammatory disease may include, but is not limited to, one or more of: allergy, ankylosing spondylitis, asthma, atopic dermatitis, autoimmune diseases or disorders, cancer, celiac disease, chronic obstructive pulmonary disease (COPD), chronic peptic ulcer, cystic fibrosis, diabetes (e.g., type 1 diabetes and type 2 diabetes), glomerulonephritis, gout, hepatitis (e.g., active hepatitis), an immune-mediated disease or disorder, inflammatory bowel disease (IBD) such as Crohn's disease and ulcerative colitis, myositis, osteoarthritis, pelvic inflammatory disease (PID), multiple sclerosis, neurodegenerative diseases of aging, periodontal disease (e.g., periodontitis), preperfusion injury transplant rejection, psoriasis, pulmonary fibrosis, rheumatic disease, scleroderma, sinusitis, tuberculosis.

The autoimmune disease or disorder may include, but is not limited to, one or more of: Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Vogt-Koyanagi-Harada Disease.

The cancer may include, but is not limited to, one or more of: Adenoid Cystic Carcinoma, Adrenal Gland Cancer, Amyloidosis, Anal Cancer, Ataxia-Telangiectasia, Atypical Mole Syndrome, Basal Cell Carcinoma, Bile Duct Cancer, Birt Hogg Dube Syndrome, Bladder Cancer, Bone Cancer, Brain Tumor, Breast Cancer, Breast Cancer in Men, Carcinoid Tumor, Cervical Cancer, Colorectal Cancer, Ductal Carcinoma, Endometrial Cancer, Esophageal Cancer, Gastric Cancer, Gastrointestinal Stromal Tumor (GIST), HER2-Positive Breast Cancer, Islet Cell Tumor, Juvenile Polyposis Syndrome, Kidney Cancer, Laryngeal Cancer, Leukemia—Acute Lymphoblastic Leukemia, Leukemia—Acute Lymphocytic (ALL), Leukemia—Acute Myeloid AML, Leukemia—Adult, Leukemia—Childhood, Leukemia—Chronic Lymphocytic (CLL), Leukemia—Chronic Myeloid (CML), Liver Cancer, Lobular Carcinoma, Lung Cancer, Lung Cancer—Small Cell (SCLC), Lung Cancer—Non-small Cell (NSCLC), Lymphoma—Hodgkin's, Lymphoma—Non-Hodgkin's, Malignant Glioma, Melanoma, Meningioma, Multiple Myeloma, Myelodysplastic Syndrome (MDS), Nasopharyngeal Cancer, Neuroendocrine Tumor, Oral Cancer, Osteosarcoma, Ovarian Cancer, Pancreatic Cancer, Pancreatic Neuroendocrine Tumors, Parathyroid Cancer, Penile Cancer, Peritoneal Cancer, Peutz-Jeghers Syndrome, Pituitary Gland Tumor, Polycythemia Vera, Prostate Cancer, Renal Cell Carcinoma, Retinoblastoma, Salivary Gland Cancer, Sarcoma, Sarcoma-Kaposi, Skin Cancer, Small Intestine Cancer, Stomach Cancer, Testicular Cancer, Thymoma, Thyroid Cancer, Uterine (Endometrial) Cancer, Vaginal Cancer, and Wilms' Tumor.

The inflammatory disease may be treated with a variety of treatments (e.g., anti-inflammatory treatments), such as non-steroidal anti-inflammatory drugs (NSAIDs), analgesics (e.g., acetaminophen), corticosteroids, herbal supplements, and other anti-inflammatory drugs or supplements.

In some embodiments, the inflammatory disease or condition may comprise a likelihood, risk, or susceptibility of having an inflammatory disease in the future (e.g., within about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1.5 days, about 2 days, about 2.5 days, about 3 days, about 3.5 days, about 4 days, about 4.5 days, about 5 days, about 5.5 days, about 6 days, about 6.5 days, about 7 days, about 8 days, about 9 days, about 10 days, about 12 days, about 14 days, about 3 weeks, about 4 weeks, about 5 weeks, about 6 weeks, about 7 weeks, about 8 weeks, about 9 weeks, about 10 weeks, about 11 weeks, about 12 weeks, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years, about 7 years, about 8 years, about 9 years, about 10 years, or more than about 10 years).

The biological sample may be taken before and/or after treatment of a subject with the inflammatory disease or condition. Biological samples may be obtained from a subject during a treatment or a treatment regime. Multiple biological samples may be obtained from a subject to monitor the effects of the treatment over time. The biological sample may be taken from a subject known or suspected of having an inflammatory disease or condition for which a definitive positive or negative diagnosis is not available via clinical tests. The sample may be taken from a subject suspected of having an inflammatory disease or condition. The biological sample may be taken from a subject experiencing unexplained symptoms, such as fatigue, nausea, weight loss, aches and pains, weakness, or bleeding. The biological sample may be taken from a subject having explained symptoms. The biological sample may be taken from a subject at risk of developing an inflammatory disease or condition due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

The biological sample may contain one or more analytes capable of being assayed, such as deoxyribonucleic acid (DNA) molecules suitable for assaying to generate genomic data, ribonucleic acid (RNA) molecules suitable for assaying to generate transcriptomic data, proteins suitable for assaying to generate proteomic data, metabolites suitable for assaying to generate metabolomic data, or a mixture or combination thereof. One or more such analytes (e.g., DNA molecules, RNA molecules, proteins, and/or metabolites) may be isolated or extracted from one or more biological samples of a subject for downstream assaying using one or more suitable assays.

After obtaining a biological sample from the subject, the biological sample may be processed to generate datasets indicative of an inflammatory disease or condition of the subject. For example, a presence, absence, or quantitative assessment of nucleic acid molecules of the biological sample at a panel of inflammatory disease-associated genomic loci (e.g., quantitative measures of DNA or RNA at the inflammatory disease-associated genomic loci), proteomic data comprising quantitative measures of proteins of the dataset at a panel of inflammatory disease-associated proteins, and/or metabolome data comprising quantitative measures of a panel of inflammatory disease-associated metabolites may be indicative of an inflammatory disease-associated. Processing the biological sample obtained from the subject may comprise (i) subjecting the biological sample to conditions that are sufficient to isolate, enrich, or extract a plurality of nucleic acid molecules, proteins, and/or metabolites, and (ii) assaying the plurality of nucleic acid molecules, proteins, and/or metabolites to generate the dataset.

In some embodiments, a plurality of nucleic acid molecules is extracted from the biological sample and subjected to sequencing to generate a plurality of sequencing reads. The nucleic acid molecules may comprise deoxyribonucleic acid (DNA) or ribonucleic acid (RNA). The nucleic acid molecules (e.g., DNA or RNA) may be extracted from the biological sample by a variety of methods, such as a FastDNA Kit protocol from MP Biomedicals, a QIAamp DNA cell-free biological mini kit from Qiagen, or a cell-free biological DNA isolation kit protocol from Norgen Biotek. The extraction method may extract all DNA or RNA molecules from a sample. Alternatively, the extract method may selectively extract a portion of DNA or RNA molecules from a sample. Extracted RNA molecules from a sample may be converted to cDNA molecules by reverse transcription (RT).

The sequencing may be performed by any suitable sequencing methods, such as massively parallel sequencing (MPS), paired-end sequencing, high-throughput sequencing, next-generation sequencing (NGS), shotgun sequencing, single-molecule sequencing, nanopore sequencing, semiconductor sequencing, pyrosequencing, sequencing-by-synthesis (SBS), sequencing by binding, sequencing-by-ligation, sequencing-by-hybridization, and RNA-Seq (Illumina). The sequencing may comprise unbiased sequencing, such as whole genome sequencing (WGS). The sequencing may comprise targeted sequencing, with higher sequencing depth or targeted enrichment of a plurality of inflammatory disease-associated genomic loci.

The sequencing may comprise nucleic acid amplification (e.g., of DNA or RNA molecules). In some embodiments, the nucleic acid amplification is polymerase chain reaction (PCR). A suitable number of rounds of PCR (e.g., PCR, qPCR, reverse-transcriptase PCR, digital PCR, etc.) may be performed to sufficiently amplify an initial amount of nucleic acid (e.g., RNA or DNA) to a desired input quantity for subsequent sequencing. In some cases, the PCR may be used for global amplification of target nucleic acids. This may comprise using adapter sequences that may be first ligated to different molecules followed by PCR amplification using universal primers. PCR may be performed using any of a number of commercial kits, e.g., provided by Life Technologies, Affymetrix, Promega, Qiagen, etc. In other cases, only certain target nucleic acids within a population of nucleic acids may be amplified. Specific primers, possibly in conjunction with adapter ligation, may be used to selectively amplify certain targets for downstream sequencing. The PCR may comprise targeted amplification of one or more genomic loci, such as genomic loci associated with pregnancy-related states. The sequencing may comprise use of simultaneous reverse transcription (RT) and polymerase chain reaction (PCR), such as a OneStep RT-PCR kit protocol by Qiagen, NEB, Thermo Fisher Scientific, or Bio-Rad.

DNA or RNA molecules isolated or extracted from a biological sample may be tagged, e.g., with identifiable tags, to allow for multiplexing of a plurality of samples. Any number of DNA or RNA samples may be multiplexed. For example a multiplexed reaction may contain DNA or RNA from at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 initial biological samples. For example, a plurality of biological samples may be tagged with sample barcodes such that each DNA molecule may be traced back to the sample (and the subject) from which the DNA molecule originated. Such tags may be attached to DNA or RNA molecules by ligation or by PCR amplification with primers.

After subjecting the nucleic acid molecules to sequencing, suitable bioinformatics processes may be performed on the sequence reads to generate the data indicative of the presence, absence, or relative assessment of the inflammatory disease-associated genomic loci. For example, the sequence reads may be aligned to one or more reference genomes (e.g., a genome of one or more species such as a human genome). The aligned sequence reads may be quantified at one or more genomic loci to generate the datasets indicative of the inflammatory disease. For example, quantification of sequences corresponding to a plurality of genomic loci associated with inflammatory disease may generate the datasets indicative of the inflammatory disease.

The biological sample may be processed without any nucleic acid extraction. For example, the inflammatory disease may be identified or monitored in the subject by using probes configured to selectively enrich nucleic acid (e.g., DNA or RNA) molecules corresponding to the plurality of inflammatory disease-associated genomic loci. The probes may be nucleic acid primers. The probes may have sequence complementarity with nucleic acid sequences from one or more of the plurality of inflammatory disease-associated genomic loci or genomic regions. The plurality of inflammatory disease-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more distinct inflammatory disease-associated genomic loci or genomic regions.

The probes may be nucleic acid molecules (e.g., DNA or RNA) having sequence complementarity with nucleic acid sequences (e.g., DNA or RNA) of the one or more genomic loci (e.g., inflammatory disease-associated genomic loci). These nucleic acid molecules may be primers or enrichment sequences. The assaying of the biological sample using probes that are selective for the one or more genomic loci (e.g., inflammatory disease-associated genomic loci) may comprise use of array hybridization (e.g., microarray-based), polymerase chain reaction (PCR), or nucleic acid sequencing (e.g., RNA sequencing or DNA sequencing). In some embodiments, DNA or RNA may be assayed by one or more of: isothermal DNA/RNA amplification methods (e.g., loop-mediated isothermal amplification (LAMP), helicase dependent amplification (HDA), rolling circle amplification (RCA), recombinase polymerase amplification (RPA)), immunoassays, electrochemical assays, surface-enhanced Raman spectroscopy (SERS), quantum dot (QD)-based assays, molecular inversion probes, droplet digital PCR (ddPCR), CRISPR/Cas-based detection (e.g., CRISPR-typing PCR (ctPCR), specific high-sensitivity enzymatic reporter un-locking (SHERLOCK), DNA endonuclease targeted CRISPR trans reporter (DETECTR), and CRISPR-mediated analog multi-event recording apparatus (CAMERA)), and laser transmission spectroscopy (LTS).

The assay readouts may be quantified at one or more genomic loci (e.g., inflammatory disease-associated genomic loci) to generate the data indicative of the inflammatory disease. For example, quantification of array hybridization or polymerase chain reaction (PCR) corresponding to a plurality of genomic loci (e.g., inflammatory disease-associated genomic loci) may generate data indicative of the inflammatory disease. Assay readouts may comprise quantitative PCR (qPCR) values, digital PCR (dPCR) values, digital droplet PCR (ddPCR) values, fluorescence values, etc., or normalized values thereof. The assay may be a home use test configured to be performed in a home setting.

The biological samples may be processed using a methylation-specific assay. For example, a methylation-specific assay may be used to identify a quantitative measure (e.g., indicative of a presence, absence, or relative amount) of methylation each of a plurality of inflammatory disease-associated genomic loci in a biological sample of the subject. The methylation-specific assay may be configured to process biological samples such as a blood sample or a urine sample (or derivatives thereof) of the subject. A quantitative measure (e.g., indicative of a presence, absence, or relative amount) of methylation of inflammatory disease-associated genomic loci in the biological sample may be indicative of one or more inflammatory diseases. The methylation-specific assay may be used to generate datasets indicative of the quantitative measure (e.g., indicative of a presence, absence, or relative amount) of methylation of each of a plurality of inflammatory disease-associated genomic loci in the biological sample of the subject.

The methylation-specific assay may comprise, for example, one or more of: a methylation-aware sequencing (e.g., using bisulfite treatment), pyrosequencing, methylation-sensitive single-strand conformation analysis (MS-SSCA), high-resolution melting analysis (HRM), methylation-sensitive single-nucleotide primer extension (MS-SnuPE), base-specific cleavage/MALDI-TOF, microarray-based methylation assay, methylation-specific PCR, targeted bisulfite sequencing, oxidative bisulfite sequencing, mass spectroscopy-based bisulfite sequencing, or reduced representation bisulfite sequence (RRBS).

Subject recruitment in the International Inflammatory Bowel Disease Genetics Consortium (IIBDGC) cohort may be performed as follows. Briefly, 13,523 patients with Crohn's disease (CD) and 33,902 non-IBD control subjects of European ancestry are recruited from 15 countries in Europe, North America, and Oceania. Diagnosis of IBD are performed based on accepted radiological, endoscopic, and histopathological evaluation. All included cases fulfill clinical criteria for IBD. Written informed consent is obtained from all study participants. The whole IIBDGC cohort, after excluding any overlap with a Cedars cohort, is used as a training set in the current investigation.

Details of recruitment of CD patients at Cedars-Sinai Medical Center may be performed as follows. Briefly, 2,843 CD cases with genotype data (after QC) are included as cases in the Cedars cohort (test set). The diagnosis of each patient is performed based on standard endoscopic, histologic, and radiographic features. Blood samples are collected at the time of enrollment. The study protocol and data collection, including DNA preparation and genotyping, are approved by the Cedars-Sinai Medical Center Institutional Review Board. Written informed consent is obtained from all study participants.

Genotyping and genotype quality control (QC) may be performed as follows. Genotyping of the Cedars cohort is performed at Cedars Sinai Medical Center using an Illumina ImmunoChip array. Individual and genotype missingness, allele frequencies, and deviations from Hardy-Weinberg Equilibrium are calculated using the PLINK software package (pngu.mgh.harvard.edu/~purcell/plink). Individual-level QC thresholds may include a high genotyping call rate (e.g., greater than 95%) and a low inbreeding coefficient (e.g., less than 0.05). Ethnicity outliers may be identified using Admixture software and may be removed. Single nucleotide polymorphisms (SNPs) with a low call rate (e.g., less than 0.95), with a low minor allele frequency (MAF) (e.g., less than 0.01), and that strongly deviated from Hardy-Weinberg equilibrium (e.g., $p<1\times10^{-7}$) may also be removed.

Genotyping and QC in the IIBDGC cohort may be performed as follows. In brief, the IIBDGC Immunochip samples are genotyped in 36 batches, and genotype calling is performed separately for each batch. Similar QC may be performed, which removes SNPs with a call rate lower than 98% across all genotyping batches or 90% in one of the genotyping batches, not in 1000 Genomes Project Phase I, failing Hardy-Weinberg Equilibrium (FDR$<1\times10^{-5}$ across all samples or within each genotyping batch), or monomorphic SNPs. Individuals may be assigned to different populations based on principal components and those not in the European Ancestry cluster, with a low call rate (e.g., less than 98%), outlying heterozygosity rate (e.g., FDR less than 0.01) or cryptic relatedness (e.g., identity by decent greater than 0.4) may be removed.

A set of 115,519 SNPs that passed the QC in both IIBDGC and Cedars cohort may be included in current analysis. Of those SNPs, 1,403 are known CD variants or in LD with known CD variants with r2>0.2 in the "1000 Genomes Project" phase3 data (available at www.internationalgenome.org/category/phase-3/, which is incorporated herein by reference in its entirety). These 1,403 variants that are either known or in LD (r2>0.2) with known CD variants may constitute the "DL-known" set of SNPs, and the other 114,116 variants not in LD with known variants may constitute the "DL-others" set of SNPs.

Deep learning prediction model building may be performed as follows. A multi-layer feedforward artificial neural network, also known as a convolutional neural network (CNN), may be applied to the genetic datasets. The CNN may be a deep learning algorithm that is trained with a stochastic gradient descent using back-propagation. The network may contain a large number of hidden layers consisting of neurons with activation functions (e.g., tanh, rectifier, or maxout activation functions). Advanced features such as adaptive learning rate, rate annealing, momentum training, dropout, $L_1$ or $L_2$ regularization, checkpointing, and grid search may be used to enable high predictive accuracy. Further, the prediction model may be further developed by integration with other machine learning approaches, such as XGBoost, Gradient Boost, and Random Forest, to further improve the prediction performance. In addition, the incorporation of other "-omics" data (e.g., transcriptome and microbiome) may enable more informative predictions. Further, the methods and systems disclosed herein may be applied to develop prediction models for a variety of complex diseases, including inflammatory diseases, ulcerative colitis (UC), cardiovascular disease (CVD), and type-2 diabetes (T2D).

In some embodiments, a CNN may be a tuple N=(L, T, Φ), where each of its elements is defined as follows: L=$L_{1-k}$ is a set of layers such that $L_1$ is the input layer, $L_K$ is the output layer, and the layers other than the input layer and the output layer are called hidden layers. Each layer $L_k$ may comprise $s_k$ nodes, which are also called neurons. The l-th neuron of layer k may be denoted by $n_k$. T⊆L×L may be a set of connections between layers such that, except for the input and output layers, each layer has an incoming connection and an outgoing connection. Φ=$\varphi_{1-k}$ may be a set of activation functions $\varphi_k$: one for each non-input layer. The value of $n_{k,l}$ may be denoted by $v_{k,l}$. Except for the input nodes, every node may be connected to nodes in the preceding layer by pre-defined weights for all k and l with 2≤k≤K and 1≤l≤$s_k$. Finally, for any input, the neural network may assign a label, that is, the index of the node of output layer with the largest value: label=argmax$_{1\le l\le sK}$.

The deep learning algorithm may be applied separately to the 1,403 variants that are either known or in LD (r2>0.2) with known CD variants (DL-known), and the other 114,116 variants not in LD with known variants (DL-others). A 5-fold cross-validation may be applied to control for model overfitting, and an ensemble model (DL-all) based on Support Vector Machine (SVM) may be built to combine DL-known and DL-others, again with 5-fold cross-validation. After building up different deep learning models in the training dataset, those models may be fitted in the test dataset to obtain the predictions. Deep learning analysis may be performed in the software H2O, and grid search may be performed to determine the best parameter settings for DL-known and DL-others. LDpred prediction may be performed as follows. LDpred analysis may be performed using the default parameters, based on the public available summary statistics from IIBDGC. The calculated prediction score may be transformed into a probability using a logit transformation. The LDpred package in Python may be used for this analysis.

Evaluation of prediction performance may be performed as follows. Receiver Operating Characteristic (ROC) curves may be generated for different prediction models in the test dataset, and Area Under Curve (AUC) values may be calculated from the ROC curves and compared, such as by using the R package pROC. Also, the performance of difference approaches may be evaluated in enrichment of CD cases in the extreme of CD risk prediction. All these comparisons may be performed in the R software package.

High-order combination analysis may be performed as follows. As a preliminary step to explore the effects of non-linear effects in known variants, the combination effects of variants used in DL-known analysis may be examined using LAMPlink software (as described by, for example, Terada et al., "LAMPLINK: detection of statistically significant SNP combinations from GWAS data", *Bioinformatics*, 32(22), 2016, 3513-3515, which is incorporated herein by reference in its entirety). Combinations of both dominant and recessive models may be performed, and LD filtering with an r2 cutoff of 0.2 may be performed to exclude potential contamination from SNPs in strong LD with each other.

Association of predicted risk with clinical phenotypes may be performed as follows. Association of prediction score from different algorithms with clinical characteristics may be evaluated in the generalized linear model framework, with Principal Components from population stratification analysis included as covariates.

Classifiers

In some embodiments, the present disclosure provides a system, method, or kit having data analysis realized in software application, computing hardware, or both. In various embodiments, the analysis application or system includes at least a data receiving module, a data pre-processing module, a data analysis module, a data interpretation module, or a data visualization module. In one embodiment, the data receiving module may comprise computer systems that connect laboratory hardware or instrumentation with computer systems that process laboratory data. In one embodiment, the data pre-processing module may comprise hardware systems or computer software that performs operations on the data in preparation for analysis. Examples of operations that may be applied to the data in the pre-processing module include affine transformations, denoising operations, data cleaning, reformatting, or sub-sampling. A data analysis module, which may be specialized for analyzing genomic data from one or more genomic materials, can, for example, take assembled genomic sequences and perform probabilistic and statistical analysis to identify abnormal patterns related to an inflammatory disease, pathology, state, risk, condition, or phenotype. A data interpretation module may use analysis methods, for example, drawn from statistics, mathematics, or biology, to support understanding of the relation between the identified abnormal patterns and health conditions, functional states, prognoses, or risks. A data visualization module may use methods of mathematical modeling, computer graphics, or rendering to create visual representations of data that may facilitate the understanding or interpretation of results.

Feature sets may be generated from datasets obtained using one or more assays of a biological sample, and a DeepLearning algorithm may be used to process one or more of the feature sets to identify or assess the inflammatory disease or condition. For example, the DeepLearning algorithm may be used to apply a machine learning classifier to a plurality of inflammatory disease-associated genomic loci that are associated with two or more classes of individuals inputted into a machine learning model, in order to classify a subject into one of the two or more classes of individuals. For example, the DeepLearning algorithm may be used to apply a machine learning classifier to a plurality of inflammatory disease-associated genomic loci that are associated with individuals with known conditions (e.g., an inflammatory disease or disorder, such as an IBD) and individuals not having the condition (e.g., healthy individuals, or individuals who do not have an inflammatory disease or disorder, such as an IBD), in order to classify a subject as having the condition (e.g., positive test outcome) or not having the condition (e.g., negative test outcome).

The DeepLearning algorithm may be configured to identify the presence (e.g., positive test result) or absence (e.g., negative test result) of one or more inflammatory disease or conditions with an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99%. This accuracy may be achieved for a set of at least about 25, at least about 50, at least about 100, at least about 150, at least about 200, at least about 250, at least about 300, at least about 350, at least about 400, at least about 450, at least about 500, at least about 1,000, or more than about 1,000 independent samples.

The DeepLearning algorithm may comprise a machine learning algorithm, such as a supervised machine learning algorithm. The supervised machine learning algorithm may comprise, for example, a Random Forest, a support vector machine (SVM), a neural network, or a deep learning algorithm. The DeepLearning algorithm may comprise a classification and regression tree (CART) algorithm. The DeepLearning algorithm may comprise an unsupervised machine learning algorithm.

The DeepLearning algorithm may comprise a classifier configured to accept as input a plurality of input variables or features (e.g., inflammatory disease-associated genomic loci) and to produce or output one or more output values based on the plurality of input variables or features (e.g., inflammatory disease-associated genomic loci). The plurality of input variables or features may comprise one or more datasets indicative of the presence (e.g., positive test result) or absence (e.g., negative test result) of one or more inflammatory disease or conditions. For example, an input variable or feature may comprise a number of sequences corresponding to or aligning to each of the plurality of inflammatory disease-associated genomic loci.

The plurality of input variables or features may also include clinical information of a subject, such as health data. For example, the health data of a subject may comprise one or more of: a diagnosis of one or more inflammatory disease or conditions, a prognosis of one or more inflammatory disease or conditions, a risk of having one or more inflammatory disease or conditions, screening or testing results of one of more inflammatory disease or conditions, a treatment history of one or more inflammatory disease or conditions, a history of previous treatment for one or more inflammatory disease or conditions, a history of prescribed or other medications, a history of prescribed medical devices, personal characteristics (e.g., age, race, ethnicity, height, weight, sex, geographic location, diet, exercise, smoking status, family history of IBD), and one or more symptoms of the subject.

For example, the inflammatory disease or condition may comprise an IBD, which may comprise one or more of: Crohn's disease and ulcerative colitis. As another example, the symptoms may include one or more of: diarrhea, abdominal pain, abdominal cramping, fever, fatigue, presence of blood in stool, blood clots, reduced appetite, weight loss, bowel obstruction, inflammation, swelling, dehydration, or a combination thereof. As another example, the screening or testing results may include one or more of: a blood test, fetal occult blood test (FOBT), colonoscopy, sigmoidoscopy, endoscopy, enteroscopy, X-ray scan, computerized tomography (CT) scan, positron emission tomography (PET) scan, PET-CT scan, magnetic resonance imaging (MRI), ultrasound scan, or a combination thereof. As another example, the prescribed or other medications or drugs may include one or more of: anti-inflammatory drugs, immunosuppressant drugs, antibiotics, anti-diarrheal medications, pain relievers, iron supplements, calcium supplements, vitamin D supplements, or a combination thereof. As another example, the previous treatment for inflammatory disease or conditions may include surgery (e.g., colectomy).

The DeepLearning algorithm may comprise a classifier, such that each of the one or more output values comprises one of a fixed number of possible values (e.g., a linear classifier, a logistic regression classifier, etc.) indicating a classification of the sample by the classifier. The DeepLearning algorithm may comprise a binary classifier, such that each of the one or more output values comprises one of two values (e.g., $\{0, 1\}$, $\{$positive, negative$\}$, or $\{$high-risk, low-risk$\}$) indicating a classification of the sample by the classifier. The DeepLearning algorithm may be another type of classifier, such that each of the one or more output values comprises one of more than two values (e.g., $\{0, 1, 2\}$, $\{$positive, negative, or indeterminate$\}$, or $\{$high-risk, intermediate-risk, or low-risk$\}$) indicating a classification of the sample by the classifier.

The classifier may be configured to classify samples by assigning output values, which may comprise descriptive labels, numerical values, or a combination thereof. Some of the output values may comprise descriptive labels. Such descriptive labels may provide an identification or indication of the presence (e.g., positive test result) or absence (e.g., negative test result) of one or more inflammatory disease or conditions of the subject, and may comprise, for example, positive, negative, high-risk, intermediate-risk, low-risk, or indeterminate. Such descriptive labels may provide an identification of a treatment for the one or more inflammatory disease or conditions of the subject, and may comprise, for example, a therapeutic intervention, a duration of the therapeutic intervention, and/or a dosage of the therapeutic intervention suitable to treat the one or more conditions of the subject. Such descriptive labels may provide an identification of secondary clinical tests that may be appropriate to perform on the subject, and may comprise, for example, blood test, fetal occult blood test (FOBT), colonoscopy, sigmoidoscopy, endoscopy, enteroscopy, X-ray scan, computerized tomography (CT) scan, positron emission tomography (PET) scan, PET-CT scan, magnetic resonance imaging (MRI), ultrasound scan, or a combination thereof. For example, such descriptive labels may provide a prognosis of the one or more conditions of the subject. As another example, such descriptive labels may provide a relative assessment of the one or more conditions of the subject. Some descriptive labels may be mapped to numerical values, for example, by mapping "positive" to 1 and "negative" to 0.

The classifier may be configured to classify samples by assigning output values that comprise numerical values, such as binary, integer, or continuous values. Such binary output values may comprise, for example, $\{0, 1\}$, $\{$positive, negative$\}$, or $\{$high-risk, low-risk$\}$. Such integer output values may comprise, for example, $\{0, 1, 2\}$. Such continuous output values may comprise, for example, a probability value of at least 0 and no more than 1. Such continuous output values may comprise, for example, an un-normalized probability value of at least 0. Such continuous output values may indicate a prognosis of the one or more inflammatory disease or conditions of the subject. Some numerical values may be mapped to descriptive labels, for example, by mapping 1 to "positive" and 0 to "negative."

The classifier may be configured to classify samples by assigning output values based on one or more cutoff values. For example, a binary classification of samples may assign an output value of "positive" or 1 if the sample indicates that the subject has at least a 50% probability of having one or more inflammatory disease or conditions, thereby assigning the subject to a class of individuals receiving a positive test result. As another example, a binary classification of samples may assign an output value of "negative" or 0 if the sample indicates that the subject has less than a 50% probability of having one or more inflammatory disease or conditions, thereby assigning the subject to a class of individuals receiving a negative test result. In this case, a single cutoff value of 50% is used to classify samples into one of the two possible binary output values or classes of individuals (e.g., those receiving a positive test result and those receiving a negative test result). Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, the classifier may be configured to classify samples by assigning an output value of "positive" or 1 if the sample indicates that the subject has a probability of having one or more inflammatory disease or conditions of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of samples may assign an output value of "positive" or 1 if the sample indicates that the subject has a probability of having one or more inflammatory disease or conditions of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classifier may be configured to classify samples by assigning an output value of "negative" or 0 if the sample indicates that the subject has a probability of having one or more inflammatory disease or conditions of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of samples may assign an output value of "negative" or 0 if the sample indicates that the subject has a probability of having one or more inflammatory disease or conditions of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classifier may be configured to classify samples by assigning an output value of "indeterminate" or 2 if the sample is not classified as "positive", "negative", 1, or 0. In this case, a set of two cutoff values is used to classify samples into one of the three possible output values or classes of individuals (e.g., corresponding to outcome groups of individuals having "low risk," "intermediate risk," and "high risk" of having one or more inflammatory disease or conditions, such as an inflammatory disease or disorder). Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify samples into one of n+1 possible output values or classes of individuals, where n is any positive integer.

The DeepLearning algorithm may be trained with a plurality of independent training samples. Each of the independent training samples may comprise a sample from a subject, associated datasets obtained by assaying the sample (as described elsewhere herein), and one or more known output values or classes of individuals corresponding to the sample (e.g., a clinical diagnosis, prognosis, absence, or treatment efficacy of an inflammatory disease or condition of the subject). Independent training samples may comprise samples and associated datasets and outputs obtained or derived from a plurality of different subjects. Independent training samples may comprise samples and associated datasets and outputs obtained at a plurality of different time points from the same subject (e.g., on a regular basis such as weekly, biweekly, or monthly), as part of a longitudinal monitoring of a subject before, during, and after a course of treatment for one or more inflammatory disease or conditions of the subject. Independent training samples may be associated with presence of the inflammatory disease or condition (e.g., training samples comprising samples and associated datasets and outputs obtained or derived from a plurality of subjects known to have the inflammatory disease or condition). Independent training samples may be associated with absence of the inflammatory disease or condition (e.g., training samples comprising samples and associated datasets and outputs obtained or derived from a plurality of subjects who are known to not have a previous diagnosis of the inflammatory disease or condition or who have received a negative test result for the inflammatory disease or condition).

The DeepLearning algorithm may be trained with at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The independent training samples may comprise samples associated with presence of the condition and/or samples associated with absence of the inflammatory disease or condition. The DeepLearning algorithm may be trained with no more than about 500, no more than about 450, no more than about 400, no more than about 350, no more than about 300, no more than about 250, no more than about 200, no more than about 150, no more than about 100, or no more than about 50 independent training samples associated with presence of the inflammatory disease or condition. The DeepLearning algorithm may be trained with no more than about 500, no more than about 450, no more than about 400, no more than about 350, no more than about 300, no more than about 250, no more than about 200, no more than about 150, no more than about 100, or no more than about 50 independent training samples associated with absence of the inflammatory disease or condition. In some embodiments, the sample is independent of samples used to train the DeepLearning algorithm.

The DeepLearning algorithm may be trained with a first number of independent training samples associated with a presence of the inflammatory disease or condition and a second number of independent training samples associated with an absence of the inflammatory disease or condition. The first number of independent training samples associated with presence of the inflammatory disease or condition may be no more than the second number of independent training samples associated with absence of the inflammatory disease or condition. The first number of independent training samples associated with a presence of the inflammatory disease or condition may be equal to the second number of independent training samples associated with an absence of the inflammatory disease or condition. The first number of independent training samples associated with a presence of the inflammatory disease or condition may be greater than the second number of independent training samples associated with an absence of the inflammatory disease or condition.

The DeepLearning algorithm may comprise a classifier configured to identify the presence (e.g., positive test result) or absence (e.g., negative test result) of one or more inflammatory disease or conditions at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The accuracy of identifying the presence (e.g., positive test result) or absence (e.g., negative test result) of the one or more conditions by the DeepLearning algorithm may be calculated as the percentage of independent test samples (e.g., subjects known to have the inflammatory disease or condition or subjects with negative clinical test results for the inflammatory disease or condition) that are correctly identified or classified as having or not having the inflammatory disease or condition.

The DeepLearning algorithm may comprise a classifier configured to identify one or more inflammatory diseases or conditions with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the inflammatory disease or condition using the DeepLearning algorithm may be calculated as the percentage of samples identified or classified as having the inflammatory disease or condition that correspond to subjects that truly have the inflammatory disease or condition.

The DeepLearning algorithm may comprise a classifier configured to identify one or more inflammatory disease or conditions with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the inflammatory disease or condition using the DeepLearning algorithm may be calculated as the percentage of samples identified or classified as not having the inflammatory disease or condition that correspond to subjects that truly do not have the inflammatory disease or condition.

The DeepLearning algorithm may comprise a classifier configured to identify one or more inflammatory disease or conditions with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the inflammatory disease or condition using the DeepLearning algorithm may be calculated as the percentage of independent test samples associated with presence of the inflammatory disease or condition (e.g., subjects known to have the inflammatory disease or condition) that are correctly identified or classified as having the inflammatory disease or condition.

The DeepLearning algorithm may comprise a classifier configured to identify one or more inflammatory disease or conditions with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the inflammatory disease or condition using the DeepLearning algorithm may be calculated as the percentage of independent test samples associated with absence of the inflammatory disease or condition (e.g., subjects with negative clinical test results for the inflammatory disease or condition) that are correctly identified or classified as not having the inflammatory disease or condition.

The DeepLearning algorithm may comprise a classifier configured to identify the presence (e.g., positive test result) or absence (e.g., negative test result) of one or more inflammatory disease or conditions with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operator Characteristic (ROC) curve (e.g., the area under the ROC curve) associated with the DeepLearning algorithm in classifying samples as having or not having the inflammatory disease or condition. The AUC may range from a value of 0 to 1, where an AUC of 0.5 is indicative of a completely random classifier (e.g., a coin flip) and an AUC of 1 is indicative of a perfectly accurate classifier (with sensitivity of 100% and specificity of 100%).

Classifiers of the DeepLearning algorithm may be adjusted or tuned to improve or optimize one or more performance metrics, such as accuracy, PPV, NPV, clinical sensitivity, clinical specificity, AUC, or a combination thereof (e.g., a performance index incorporating a plurality of such performance metrics, such as by calculating a weight sum therefrom), of identifying the presence (e.g., positive test result) or absence (e.g., negative test result) of the inflammatory disease or condition. The classifiers may be adjusted or tuned by adjusting parameters of the classifiers (e.g., a set of cutoff values used to classify a sample as described elsewhere herein, or weights of a neural network) to improve or optimize the performance metrics. The one or more classifiers may be adjusted or tuned so as to reduce an overall classification error (e.g., an "out-of-bag" or oob error rate for a Random Forest classifier). The one or more classifiers may be adjusted or tuned continuously during the training process (e.g., as sample datasets are added to the training set) or after the training process has completed.

The DeepLearning algorithm may comprise a plurality of classifiers (e.g., an ensemble) such that the plurality of classifications or outcome values of the plurality of classifiers may be combined to produce a single classification or outcome value for the sample (e.g., to generate an ensemble output). For example, a sum or a weighted sum of the plurality of classifications or outcome values of the plurality of classifiers may be calculated to produce a single classification or outcome value for the sample. As another example, a majority vote of the plurality of classifications or outcome values of the plurality of classifiers may be identified to produce a single classification or outcome value for the sample. In this manner, a single classification or outcome value may be produced for the sample having greater confidence or statistical significance than the individual classifications or outcome values produced by each of the plurality of classifiers.

After the DeepLearning algorithm is initially trained, a subset of the inputs may be identified as most influential or most important to be included for making high-quality classifications (e.g., having highest permutation feature importance). For example, a subset of the panel of inflammatory disease-associated genomic loci may be identified as most influential or most important to be included for making high-quality classifications or identifications of inflammatory disease or conditions (or sub-types of inflammatory disease or conditions). The panel of inflammatory disease-associated genomic loci, or a subset thereof, may be ranked based on classification metrics indicative of each influence or importance of each individual inflammatory disease-associated genomic locus toward making high-quality classifications or identifications of inflammatory disease or conditions (or sub-types of inflammatory disease or conditions). Such metrics may be used to reduce, in some cases significantly, the number of input variables (e.g., predictor variables) that may be used to train the one or more classifiers of the DeepLearning algorithm to a desired performance level (e.g., based on a desired minimum accuracy, PPV, NPV, clinical sensitivity, clinical specificity, AUC, or a combination thereof).

For example, if training a classifier of the DeepLearning algorithm with a plurality comprising several dozen or hundreds of input variables to the classifier results in an accuracy of classification of more than 99%, then training the classifier of the DeepLearning algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality may yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%).

As another example, if training a classifier of the Deep-Learning algorithm with a plurality comprising several dozen or hundreds of input variables to the classifier results in a sensitivity or specificity of classification of more than 99%, then training the classifier of the DeepLearning algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality may yield decreased but still acceptable sensitivity or specificity of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%).

The subset of the plurality of input variables (e.g., the panel of inflammatory disease-associated genomic loci) to the classifier of the DeepLearning algorithm may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics (e.g., permutation feature importance).

Upon identifying the subject as having one or more inflammatory disease or conditions, the subject may be optionally provided with a therapeutic intervention (e.g., prescribing an appropriate course of treatment to treat the one or more inflammatory disease or conditions of the subject). The therapeutic intervention may comprise a prescription of an effective dose of a drug, a further testing or evaluation of the condition, a further monitoring of the condition, or a combination thereof. If the subject is currently being treated for the condition with a course of treatment, the therapeutic intervention may comprise a subsequent different course of treatment (e.g., to increase treatment efficacy due to non-efficacy of the current course of treatment).

In some embodiments, a DeepLearning model may be used to predict a level of efficacy (e.g., a response or a non-response) of a given therapeutic intervention for an inflammatory disease of a subject. In some embodiments, a therapeutic intervention may be selected from one or more therapeutic interventions based on maximizing a predicted level of efficacy of the therapeutic intervention, minimizing side effects of the therapeutic intervention, minimizing a cost of the therapeutic intervention, or a combination thereof.

In some embodiments, upon identifying a subject as having elevated risk of developing an inflammatory disease with the DeepLeaning model described herein, a primary intervention may be administered to the subject to prevent or delay the onset of the inflammatory disease or condition. For example, a primary intervention may effectively delay onset of rheumatoid arthritis in a subject having elevated or high risk thereof.

The therapeutic intervention may include prescribed or other medications or drugs, which may include one or more of: anti-inflammatory drugs, immunosuppressant drugs, antibiotics, anti-diarrheal medications, pain relievers, iron supplements, calcium supplements, vitamin D supplements, or a combination thereof. The therapeutic intervention may include surgery (e.g., colectomy). The therapeutic intervention may be effective to alleviate or decrease one or more symptoms, which may include one or more of: diarrhea, abdominal pain, abdominal cramping, fever, fatigue, presence of blood in stool, blood clots, reduced appetite, weight loss, bowel obstruction, inflammation, swelling, dehydration, or a combination thereof.

The therapeutic intervention may comprise recommending the subject for a secondary clinical test to confirm a diagnosis of the inflammatory disease or condition. This secondary clinical test may comprise a blood test, fetal occult blood test (FOBT), colonoscopy, sigmoidoscopy, endoscopy, enteroscopy, X-ray scan, computerized tomography (CT) scan, positron emission tomography (PET) scan, PET-CT scan, magnetic resonance imaging (MRI), ultrasound scan, or a combination thereof.

The feature sets (e.g., comprising quantitative measures of a panel of inflammatory disease-associated genomic loci) may be analyzed and assessed (e.g., using a DeepLearning algorithm comprising one or more classifiers) over a duration of time to monitor a patient (e.g., subject who has an inflammatory disease or condition or who is being treated for an inflammatory disease or condition). In such cases, the feature sets of the patient may change during the course of treatment. For example, the quantitative measures of the feature sets of a patient with decreasing risk of the inflammatory disease or condition due to an effective treatment may shift toward the profile or distribution of a healthy subject (e.g., a subject without the inflammatory disease or condition). Conversely, for example, the quantitative measures of the feature sets of a patient with increasing risk of the inflammatory disease or condition due to an ineffective treatment may shift toward the profile or distribution of a subject with higher risk of the inflammatory disease or condition or a more advanced stage or severity of the inflammatory disease or condition.

The inflammatory disease or condition of the subject may be monitored by monitoring a course of treatment for treating the inflammatory disease or condition of the subject. The monitoring may comprise assessing the inflammatory disease or condition of the subject at two or more time points. The assessing may be based at least on the feature sets (e.g., quantitative measures of a panel of inflammatory disease-associated genomic loci) determined at each of the two or more time points. The therapeutic intervention may include prescribed or other medications or drugs, which may include one or more of: anti-inflammatory drugs, immunosuppressant drugs, antibiotics, anti-diarrheal medications, pain relievers, iron supplements, calcium supplements, vitamin D supplements, or a combination thereof. The therapeutic intervention may include surgery (e.g., colectomy). The therapeutic intervention may be effective to alleviate or decrease one or more symptoms, which may include one or more of: diarrhea, abdominal pain, abdominal cramping, fever, fatigue, presence of blood in stool, blood clots, reduced appetite, weight loss, bowel obstruction, inflammation, swelling, dehydration, or a combination thereof. The assessing may be based at least on the presence, absence, or severity of one or more symptoms, such as diarrhea, abdominal pain, abdominal cramping, fever, fatigue, presence of blood in stool, blood clots, reduced appetite, weight loss, bowel obstruction, inflammation, swelling, dehydration, or a combination thereof.

In some embodiments, a difference in the feature sets (e.g., quantitative measures of a panel of inflammatory disease-associated genomic loci) determined between the two or more time points may be indicative of one or more clinical indications, such as (i) a diagnosis of the inflammatory disease or condition of the subject, (ii) a prognosis of the inflammatory disease or condition of the subject, (iii) an increased risk of the inflammatory disease or condition of the subject, (iv) a decreased risk of the inflammatory disease or condition of the subject, (v) an efficacy of the course of treatment for treating the inflammatory disease or condition of the subject, and (vi) a non-efficacy of the course of treatment for treating the inflammatory disease or condition of the subject.

In some embodiments, a difference in the feature sets (e.g., quantitative measures of a panel of inflammatory disease-associated genomic loci) determined between the two or more time points may be indicative of a diagnosis of the inflammatory disease or condition of the subject. For example, if the inflammatory disease or condition was not detected in the subject at an earlier time point but was detected in the subject at a later time point, then the difference is indicative of a diagnosis of the inflammatory disease or condition of the subject. A clinical action or decision may be made based on this indication of diagnosis of the inflammatory disease or condition of the subject, such as, for example, prescribing a new therapeutic intervention for the subject. The clinical action or decision may comprise recommending the subject for a secondary clinical test to confirm the diagnosis of the condition. This secondary clinical test may include one or more of: a blood test, fetal occult blood test (FOBT), colonoscopy, sigmoidoscopy, endoscopy, enteroscopy, X-ray scan, computerized tomography (CT) scan, positron emission tomography (PET) scan, PET-CT scan, magnetic resonance imaging (MRI), ultrasound scan, or a combination thereof.

In some embodiments, a difference in the feature sets (e.g., quantitative measures of a panel of inflammatory disease-associated genomic loci) determined between the two or more time points may be indicative of a prognosis of the inflammatory disease or condition of the subject.

In some embodiments, a difference in the feature sets (e.g., quantitative measures of a panel of inflammatory disease-associated genomic loci) determined between the two or more time points may be indicative of the subject having an increased risk of the inflammatory disease or condition. For example, if the inflammatory disease or condition was detected in the subject both at an earlier time point and at a later time point, and if the quantitative measures of a panel of inflammatory disease-associated genomic loci increased from the earlier time point to the later time point, then the difference may be indicative of the subject having an increased risk of the inflammatory disease or condition. A clinical action or decision may be made based on this indication of the increased risk of the inflammatory disease or condition, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the condition. This secondary clinical test may include one or more of: a blood test, fetal occult blood test (FOBT), colonoscopy, sigmoidoscopy, endoscopy, enteroscopy, X-ray scan, computerized tomography (CT) scan, positron emission tomography (PET) scan, PET-CT scan, magnetic resonance imaging (MRI), ultrasound scan, or a combination thereof.

In some embodiments, a difference in the feature sets (e.g., quantitative measures of a panel of inflammatory disease-associated genomic loci) determined between the two or more time points may be indicative of the subject having a decreased risk of the inflammatory disease or condition. For example, if the inflammatory disease or condition was detected in the subject both at an earlier time point and at a later time point, and if the quantitative measures of a panel of inflammatory disease-associated genomic loci decreased from the earlier time point to the later time point, then the difference may be indicative of the subject having a decreased risk of the inflammatory disease or condition. A clinical action or decision may be made based on this indication of the decreased risk of the inflammatory disease or condition (e.g., continuing or ending a current therapeutic intervention) for the subject. The clinical action or decision may comprise recommending the subject for a secondary clinical test to confirm the decreased risk of the condition. This secondary clinical test may include one or more of: a blood test, fetal occult blood test (FOBT), colonoscopy, sigmoidoscopy, endoscopy, enteroscopy, X-ray scan, computerized tomography (CT) scan, positron emission tomography (PET) scan, PET-CT scan, magnetic resonance imaging (MRI), ultrasound scan, or a combination thereof.

In some embodiments, a difference in the feature sets (e.g., quantitative measures of a panel of inflammatory disease-associated genomic loci) determined between the two or more time points may be indicative of an efficacy of the course of treatment for treating the inflammatory disease or condition of the subject. For example, if the inflammatory disease or condition was detected in the subject at an earlier time point but was not detected in the subject at a later time point, then the difference may be indicative of an efficacy of the course of treatment for treating the inflammatory disease or condition of the subject. A clinical action or decision may be made based on this indication of the efficacy of the course of treatment for treating the inflammatory disease or condition of the subject, e.g., continuing or ending a current therapeutic intervention for the subject. The clinical action or decision may comprise recommending the subject for a secondary clinical test to confirm the efficacy of the course of treatment for treating the inflammatory disease or condition. This secondary clinical test may include one or more of: a blood test, fetal occult blood test (FOBT), colonoscopy, sigmoidoscopy, endoscopy, enteroscopy, X-ray scan, computerized tomography (CT) scan, positron emission tomography (PET) scan, PET-CT scan, magnetic resonance imaging (MRI), ultrasound scan, or a combination thereof.

In some embodiments, a difference in the feature sets (e.g., quantitative measures of a panel of inflammatory disease-associated genomic loci) determined between the two or more time points may be indicative of a non-efficacy of the course of treatment for treating the inflammatory disease or condition of the subject. For example, if the inflammatory disease or condition was detected in the subject both at an earlier time point and at a later time point, and if the quantitative measures of a panel of inflammatory disease-associated genomic loci increased or remained at a constant level from the earlier time point to the later time point, and if an efficacious treatment was indicated at an earlier time point, then the difference may be indicative of a non-efficacy of the course of treatment for treating the inflammatory disease or condition of the subject. A clinical action or decision may be made based on this indication of the non-efficacy of the course of treatment for treating the inflammatory disease or condition of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the inflammatory disease or condition. This secondary clinical test may include one or more of: a blood test, fetal occult blood test (FOBT), colonoscopy, sigmoidoscopy, endoscopy, enteroscopy, X-ray scan, computerized tomography (CT) scan, positron emission tomography (PET) scan, PET-CT scan, magnetic resonance imaging (MRI), ultrasound scan, or a combination thereof.

In various embodiments, machine learning methods are applied to distinguish samples in a population of samples. In one embodiment, machine learning methods are applied to distinguish samples between healthy and inflammatory disease samples.

Kits

The present disclosure provides kits for identifying or monitoring an inflammatory disease or condition of a subject. A kit may comprise probes for identifying a quantitative measure (e.g., indicative of a presence, absence, or relative amount) of sequences at each of a panel of inflammatory disease-associated genomic loci in a sample of the subject. A quantitative measure (e.g., indicative of a presence, absence, or relative amount) of sequences at each of a panel of inflammatory disease-associated genomic loci in the sample may be indicative of the inflammatory disease or condition of the subject. The probes may be selective for the sequences at the panel of inflammatory disease-associated genomic loci in the sample. A kit may comprise instructions for using the probes to process the sample to generate datasets indicative of a quantitative measure (e.g., indicative of a presence, absence, or relative amount) of sequences at each of the panel of inflammatory disease-associated genomic loci in a sample of the subject.

The probes in the kit may be selective for the sequences at the panel of inflammatory disease-associated genomic loci in the sample. The probes in the kit may be configured to selectively enrich nucleic acid (e.g., RNA or DNA) molecules corresponding to the panel of inflammatory disease-associated genomic loci. For example, the inflammatory disease-associated genomic loci may be associated with one or more single nucleotide polymorphisms (SNPs), copy number variations (CNVs), insertions or deletions (indels), fusions, translocations, or other genetic variants. The probes may be nucleic acid primers. The probes may have sequence complementarity with nucleic acid sequences from one or more of the panel of inflammatory disease-associated genomic loci. The panel of inflammatory disease-associated genomic loci may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more inflammatory disease-associated genomic loci.

The instructions in the kit may comprise instructions to assay the sample using the probes that are selective for the sequences at the panel of inflammatory disease-associated genomic loci in the sample. These probes may be nucleic acid molecules (e.g., RNA or DNA) having sequence complementarity with nucleic acid sequences (e.g., RNA or DNA) from one or more of the plurality of panel of inflammatory disease-associated genomic loci. These nucleic acid molecules may be primers or enrichment sequences. The instructions to assay the sample may comprise instructions to perform array hybridization, polymerase chain reaction (PCR), or nucleic acid sequencing (e.g., DNA sequencing or RNA sequencing) to process the sample to generate datasets indicative of a quantitative measure (e.g., indicative of a presence, absence, or relative amount) of sequences at each of the panel of inflammatory disease-associated genomic loci in the sample. A quantitative measure (e.g., indicative of a presence, absence, or relative amount) of sequences at each of a panel of inflammatory disease-associated genomic loci in the sample may be indicative of an inflammatory disease or condition.

Figure 3:
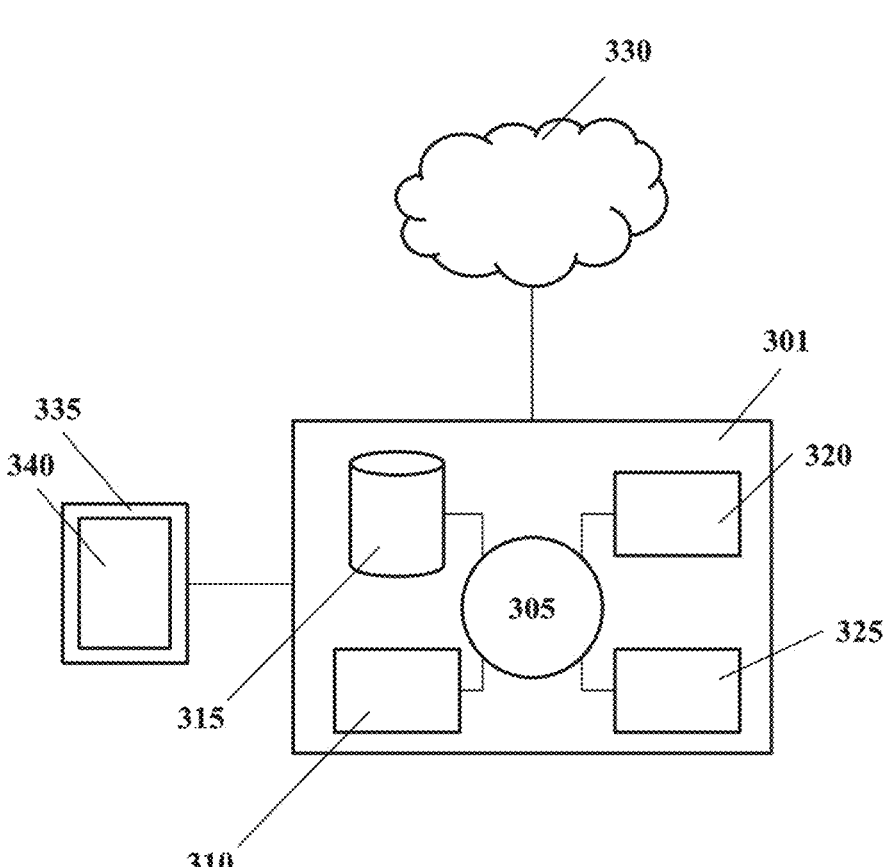
FIG. 3 shows a non-limiting example of a computer system that is programmed to implement methods of the disclosure.

The instructions in the kit may comprise instructions to measure and interpret assay readouts, which may be quantified at one or more of the panel of inflammatory disease-associated genomic loci to generate the datasets indicative of a quantitative measure (e.g., indicative of a presence, absence, or relative amount) of sequences at each of the panel of inflammatory disease-associated genomic loci in the sample. For example, quantification of array hybridization or polymerase chain reaction (PCR) corresponding to the panel of inflammatory disease-associated genomic loci may generate the datasets indicative of a quantitative measure (e.g., indicative of a presence, absence, or relative amount) of sequences at each of the panel of inflammatory disease-associated genomic loci in the sample. Assay readouts may comprise quantitative PCR (qPCR) values, digital PCR (dPCR) values, digital droplet PCR (ddPCR) values, fluorescence values, etc., or normalized values thereof Computer Systems The present disclosure provides computer systems that are programmed to implement methods of the disclosure. FIG. 3 shows a computer system 301 that is programmed or otherwise configured to, for example, (i) train and test a DeepLearning algorithm, (ii) use the DeepLearning algorithm to process data to determine an inflammatory disease or condition of a subject, (iii) determine a quantitative measure indicative of an inflammatory disease or condition of a subject, (iv) identify or monitor the inflammatory disease or condition of the subject, and (v) electronically output a report that indicative of the inflammatory disease or condition of the subject.

The computer system 301 may regulate various aspects of analysis, calculation, and generation of the present disclosure, such as, for example, (i) training and testing a Deep-Learning algorithm, (ii) using the DeepLearning algorithm to process data to determine an inflammatory disease or condition of a subject, (iii) determining a quantitative measure indicative of an inflammatory disease or condition of a subject, (iv) identifying or monitoring the inflammatory disease or condition of the subject, and (v) electronically outputting a report that indicative of the inflammatory disease or condition of the subject. The computer system 301 may be an electronic device of a user or a computer system that is remotely located with respect to the electronic device. The electronic device may be a mobile electronic device.

The computer system 301 includes a central processing unit (CPU, also "processor" and "computer processor" herein) 305, which may be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 may be a data storage unit (or data repository) for storing data. The computer system 301 may be operatively coupled to a computer network ("network") 330 with the aid of the communication interface 320. The network 330 may be the Internet, an internet and/or extranet, or an intranet and/or extranet that is in communication with the Internet.

The network 330 in some cases is a telecommunication and/or data network. The network 330 may include one or more computer servers, which may enable distributed computing, such as cloud computing. For example, one or more computer servers may enable cloud computing over the network 330 ("the cloud") to perform various aspects of the present disclosure, such as, for example, (i) training and testing a Deep-Learning algorithm, (ii) using the DeepLearning algorithm to process data to determine an inflammatory disease or condition of a subject, (iii) determining a quantitative measure indicative of an inflammatory disease or condition of a subject, (iv) identifying or monitoring the inflammatory disease or condition of the subject, and (v) electronically outputting a report that indicative of the inflammatory disease or condition of the subject. Such cloud computing may be provided by cloud computing platforms such as, for example, Amazon Web Services (AWS), Microsoft Azure, Google Cloud Platform, and IBM cloud. The network 330, in some cases with the aid of the computer system 301, may implement a peer-to-peer network, which may enable devices coupled to the computer system 301 to behave as a client or a server.

The CPU 305 may comprise one or more computer processors and/or one or more graphics processing units (GPUs). The CPU 305 may execute a sequence of machine-readable instructions, which may be embodied in a program or software. The instructions may be stored in a memory location, such as the memory 310. The instructions may be directed to the CPU 305, which may subsequently program or otherwise configure the CPU 305 to implement methods of the present disclosure. Examples of operations performed by the CPU 305 may include fetch, decode, execute, and writeback.

The CPU 305 may be part of a circuit, such as an integrated circuit. One or more other components of the system 301 may be included in the circuit. In some cases, the circuit is an application specific integrated circuit (ASIC).

The storage unit 315 may store files, such as drivers, libraries and saved programs. The storage unit 315 may store user data, e.g., user preferences and user programs. The computer system 301 in some cases may include one or more additional data storage units that are external to the computer system 301, such as located on a remote server that is in communication with the computer system 301 through an intranet or the Internet.

The computer system 301 may communicate with one or more remote computer systems through the network 330. For instance, the computer system 301 may communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user may access the computer system 301 via the network 330.

Methods as described herein may be implemented by way of machine (e.g., computer processor) executable code stored on an electronic storage location of the computer system 301, such as, for example, on the memory 310 or electronic storage unit 315. The machine-executable or machine-readable code may be provided in the form of software. During use, the code can be executed by the processor 305. In some cases, the code may be retrieved from the storage unit 315 and stored on the memory 310 for ready access by the processor 305. In some situations, the electronic storage unit 315 may be precluded, and machine-executable instructions are stored on memory 310.

The code may be pre-compiled and configured for use with a machine having a processer adapted to execute the code, or may be compiled during runtime. The code may be supplied in a programming language that may be selected to enable the code to execute in a pre-compiled or as-compiled fashion.

Aspects of the systems and methods provided herein, such as the computer system 301, may be embodied in programming. Various aspects of the technology may be thought of as "products" or "articles of manufacture" typically in the form of machine (or processor) executable code and/or associated data that is carried on or embodied in a type of machine-readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer-readable media may be involved in carrying one or more sequences of one or more instructions to a processor for execution.

The computer system 301 may include or be in communication with an electronic display 335 that comprises a user interface (UI) 340 for providing, for example, (i) a visual display indicative of training and testing of a DeepLearning algorithm, (ii) a visual display of data indicative of an inflammatory disease or condition of a subject, (iii) a quantitative measure of an inflammatory disease or condition of a subject, (iv) an identification of a subject as having an inflammatory disease or condition, or (v) an electronic report indicative of the inflammatory disease or condition of the subject. Examples of UIs include, without limitation, a graphical user interface (GUI) and web-based user interface.

Methods and systems of the present disclosure may be implemented by way of one or more algorithms. An algorithm may be implemented by way of software upon execution by the central processing unit 305. The algorithm can, for example, (i) train and test a DeepLearning algorithm, (ii) use the DeepLearning algorithm to process data to determine an inflammatory disease or condition of a subject, (iii) determine a quantitative measure indicative of an inflammatory disease or condition of a subject, (iv) identify or monitor the inflammatory disease or condition of the subject, and (v) electronically output a report that indicative of the inflammatory disease or condition of the subject.

III. EXAMPLES

The following examples are included for illustrative purposes only and are not intended to limit the scope of the invention.

Example 1: Using DeepLearning and Genetic
BigData to Construct a Disease Prediction Model
for Inflammatory Disease A Deep Learning (DL) model was built, validated and tested to predict Crohn's disease (CD) using genetic data. The performance of the DL model in this example was compared to the performance of LDpred. The DL model in this example and according to various embodiments described herein yielded more accurate predictions as compared to LDpred, underscoring the clinical utility of the DL model in clinical practice to inform decision-making (e.g., diagnosis, prognosis, selection of therapeutic intervention, disease and/or therapeutic regimen monitoring, and the like).

Methods: DL was utilized to build a disease prediction model with 13,523 Caucasian CD patients and 33,902 non-IBD controls from IIBDGC as the training dataset. This model was further validated in 2,843 CD cases recruited from a single center and 4568 non-IBD controls that were independent from the training set. Both training and validation cohorts were genotyped using ImmunoChip. 115,399 SNPs that were successfully measured in both cohorts and passed the stringent QC were included as predictors. A convolutional neural network (CNN) algorithm was used to construct a DL model, and cross-validation was performed as part of the DL model construction. Further, the association of the DL prediction score was examined with clinical phenotypes.

Performance of the DL model was compared to the LDpred algorithm (e.g., as described by Amit V. Khera et. al, Nature Genetics, 2018; which is incorporated herein by reference in its entirety). A non-trivial improvement in prediction performance of DL was observed with an Area Under the Curve (AUC) of 0.841, as compared to 0.699 using LDPred. The predicted risk from DL led to greatly enriched cases in the extreme of the DL score, with an OR of 26.32 in the top 5%. Utilising only known CD-susceptibility variants (and variants in LD with known), the DL based algorithm (DL-known) achieved an AUC of 0.826. Further analyses indicate that the improved performance of the DL-known score is likely through its ability to incorporate non-linear causal effects. Moreover, after excluding known variants, an AUC of 0.747 was observed with the DL algorithm (DL-other). Variance importance metrics of the DL-other algorithm identified 11 novel CD variants that achieved genome-wide significance in a meta-analysis incorporating 137,216 individuals. DL predicted risk score is also strongly associated with CD clinical phenotypes including disease location, severity, and need for surgery. Therefore, utilising this novel genetic algorithm, individuals with monogenic-like disease risk for CD were identified, a capability that provides progress towards early diagnosis and identifying subjects for studying preventative strategies.

Subjects were enrolled as follows. A training cohort was obtained, comprising individuals from the International IBD Genetics Consortium (IIBDGC) cohort. Subject recruitment in the IIBDGC cohort included recruiting a set of 13,523 CD patients and 33,902 non-IBD individuals of European ancestry from 18 countries in Europe, North America, and Oceania. For each of these subjects, a diagnosis of CD was made based on accepted radiological, endoscopic, and histopathological evaluation. All included cases fulfilled clinical criteria for CD and provided written consent. The entire IIBDGC cohort, after excluding any overlap with a test cohort, was used as a training dataset.

An independent cohort from Cedars-Sinai Medical Center (CSMC) was used as a test cohort to generate a test dataset. Validation was performed in this test cohort of 2,843 CD cases and 4,568 non-IBD controls. The patient recruitment for the Cedars cohort included 2,843 CD cases and 4,568 non-IBD control cases with genotype data (after QC). For each of these subjects, a diagnosis of CD was made based on standard endoscopic, histologic, and radiographic features. The study protocol and data collection, including DNA preparation and genotyping, were approved by the CSMC Institutional Review Board. Written informed consents were obtained from all study participants.

Genotyping and genotype quality control (QC) were performed as follows. Both cohorts were genotyped using Illumina ImmunoChip™ platform. Further, QC in the IIBDGC cohort was performed. In brief, the IIBDGC ImmunoChip™ samples were genotyped in 36 batches, and genotype calling was performed separately for each batch. Stringent QC was performed, removing the following: SNPs with a call rate lower than 98% across all genotyping batches or 90% in one of the genotyping batches, SNPs that did not appear in the 1000 Genomes Project Phase I, SNPs that failed Hardy-Weinberg Equilibrium ($P<10^{-5}$ across all samples or within each genotyping batch), and monomorphic SNPs. Individuals were assigned to different populations based on principal components and those not in the European Ancestry cluster, and those with low call rate (less than 98%), outlying heterozygosity rate ($P<0.01$) or cryptic relatedness (identity by decent $>0.4$) were removed.

Genotyping of the Cedars cohort was performed at CSMC using an Illumina ImmunoChip™ array. Individual and genotype missingness, allele frequencies, and deviations from Hardy-Weinberg Equilibrium were calculated using the PLINK software package (pngu.mgh.harvard.edu/~purcell/plink). Individual-level QC thresholds were used, including a genotyping call rate of greater than 95% and an inbreeding coefficient of less than 0.05. Ethnicity outliers identified using Admixture software were also removed. SNPs with a call rate of less than 0.95, minor allele frequency (MAF) of less than 0.01, and strong deviation from Hardy-Weinberg equilibrium ($P<10^{-7}$) were also removed.

A set of 115,519 SNPs available post-QC in both the IIBDGC and the RISK cohorts (as described in Example 2) were selected for further analyses. Of these, 1,403 are known CD variants or in LD with known CD variants with $r2>0.2$ in 1000 Genome Project Phase3 data. Of those variants, 102,139 variants (1,219 are known or in LD with known) are available in the RISK cohort after QC.

The Deep Learning prediction models were constructed as follows. A multi-layer feedforward artificial neural network, also known as convolutional neural network (CNN), was utilized to build the prediction model. The CNN model was constructed separately with a) the 1,403 variants that are either known or in LD ($r2>0.2$) with known CD variants (DL-known), and b) the remaining 114,116 variants not in LD with known variants (DL-others). The CNN model was optimized in the software H2O using stochastic gradient descent with both $L_1$ and $L_2$ regularization. A grid search was performed to determine the best parameter settings separately for DL-known and DL-others, including numbers of hidden layers, number of neurons in each layer, activation functions of the layers, dropout ratio, and parameters for $L_1$ and $L_2$ regularization. In the trained models, the variable relative importance was calculated using Gedeon's approach, based on the weights connecting the input features to the first two hidden layers. A 5-fold cross-validation was applied to the control for model overfitting. Further, an ensemble model (DL-comb) based on Support Vector Machine (SVM) was built to combine DL-known and DL-others with 5-fold cross-validation. After building up different Deep Learning models in the training dataset, models were fitted using the test datasets. The final prediction model was provided as a free online CD risk prediction tool (CDRP).

Prediction performance of the deep learning algorithm was compared to the LDPred approach as follows.

LDpred analysis was performed using the default parameters, based on the public available summary statistics from IIBDGC. The LDPred23 Python package was used for these analyses. LDPred analysis was performed across different p-value thresholds (1.0E-6, 3.0E-6, 1.0E-5, 3.0E-5, 1.0E-4, 3.0E-4, 0.001, 0.003, 0.01, 0.05, 0.10, and 0.25), and the p-value threshold with best AUC was selected.

Prediction performance was evaluated as follows. Receiver Operating Characteristic (ROC) curves were generated for different prediction models in the test dataset. Further, Area Under Curve (AUC) was calculated for each of the ROC curves, and compared using the R package pROC31. Further, the performance of difference approaches was evaluated in enrichment of CD cases in the extreme of CD risk prediction. All comparisons were performed in the R software package.

High-order combination analysis was performed as follows. To investigate the effects of non-linear effects in known variants (and variants associated with known), the combined effects of variants used in DL-known analysis were examined using LAMPlink software. Combinations of both dominant and recessive models were performed, and LD filtering was performed with r2 cutoff of 0.2 to exclude potential contamination from SNPs in strong LD.

Association of single variants with CD and meta-analysis was performed as follows. Association of SNPs within the top 500 of variable importance with CD was examined in the IIBDGC and CSMC cohorts separately, using logistic regression with adjustment for principal components from population stratification analysis. A meta-analysis was performed to combine the summary statistics in both cohorts as well as the summary statistics described by de Lange et al. (de Lange, K. M. et al., "Genome-wide association study implicates immune activation of multiple integrin genes in inflammatory bowel disease," *Nat Genet* 49, 256-261 (2017), which is incorporated herein by reference in its entirety), after excluding overlapping samples.

Association of predicted risk with clinical phenotypes was performed as follows. Association of prediction score from different algorithms with clinical characteristics was evaluated in the generalized linear model framework, with Principal Components from population stratification analysis included as covariates.

Results

After performing an intensive grid search to tune or optimize the hyperparameters, a CNN model with three hidden layers (154 neurons in each layer, with $L_1$ penalty of 5.0E-5 and $L_3$ penalty of 1.0E-4) was constructed for DL-known. For DL-others, a model with two hidden layers (326 neurons in each layer) with $L_1$ penalty of 6.0E-5 and $L_2$ penalty of 1.6E-4 was constructed. A SVM model combining DL-known and DL-others was then trained in the training cohort combining the DL-known and DL-others models.

Figure 2:
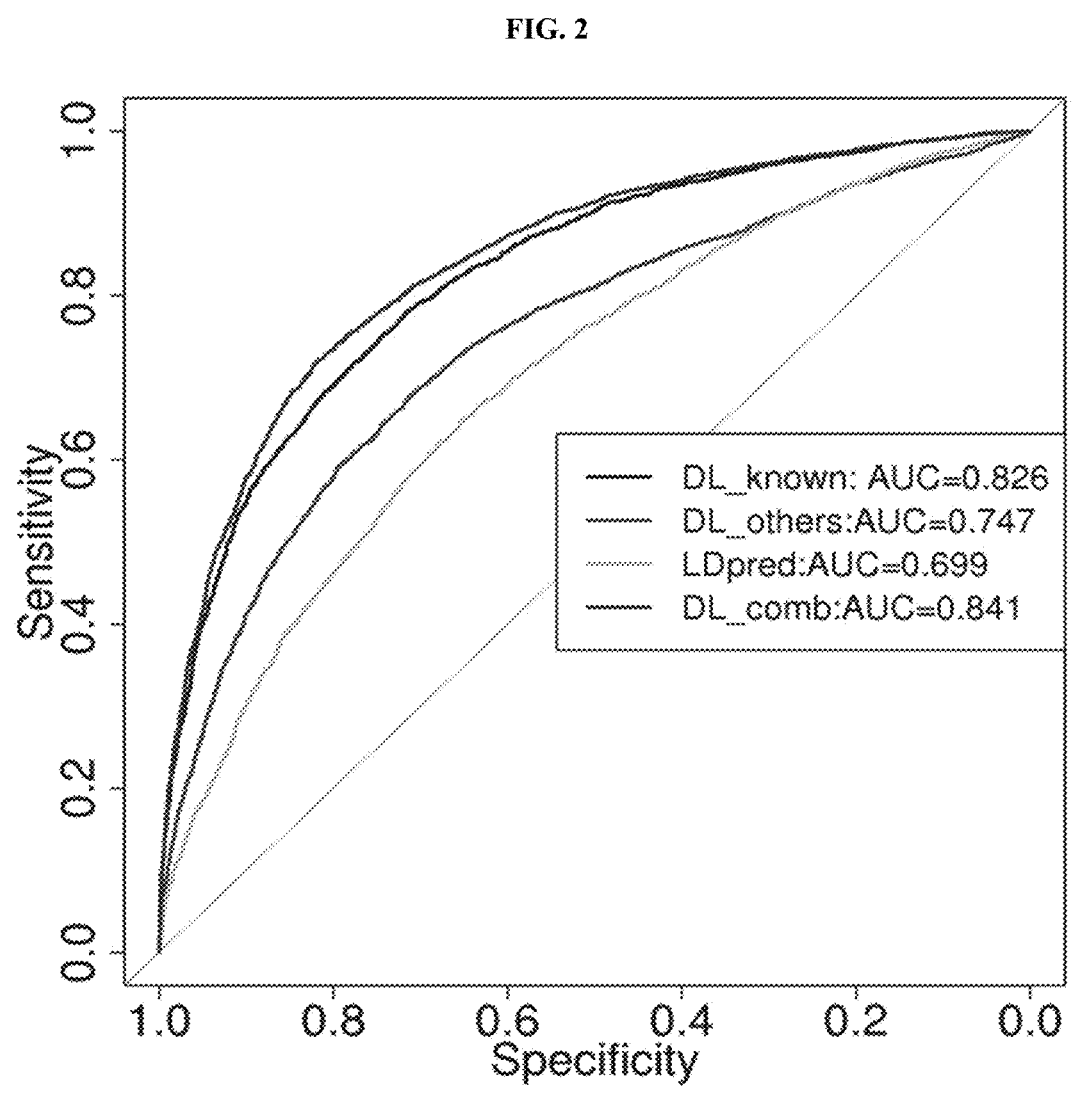

As shown in FIG. 2, a significant improvement in prediction performance was observed using the deep learning algorithm compared to LDpred. FIG. 2 shows an example of receiver operating characteristic (ROC) curves of different polygenic risk scores. The legend is as follows—AUC: Area Under the Curve; DL known: Deep Learning model using known susceptibility variants and variants in LD with susceptibility variants; DL_others: Deep Learning model using the other variants (e.g., excluding known susceptibility variants and variants in LD with these susceptibility variants) on ImmunoChip™; DL_comb: Deep Learning model combining DL-known and DL-others. In the test set, the Area Under the Curve (AUC) of the LDpred approach (with p-value cutoff of 0.01) was 0.699, while deep learning constructed using the known variants and variants in LD with known (DL-known) exhibited an AUC of 0.826, which is significantly higher than that of LDpred (p=5.75×10^-83). Deep learning with other variants (DL-others), where variants included in the DL-known analysis were excluded, exhibited an AUC of 0.741, which was also higher than the LDpred prediction (p=7.11×10^-12). Combining the DL-known and DL-other variants (DL-comb) improved the overall AUC of prediction to 0.841 (p=6.07×10^-115 compared to LDpred prediction, p=1.85×10^13 compared to DL-known), which is among the best performance of risk prediction of complex human diseases using genetic data.

This improvement in prediction accuracy led to greatly enriched cases in both the extreme and even the not-so-extreme tails of the DL-comb scores (Table 1). All deep-learning based approaches, whether based on the known variants, the remaining of the immunoChip, or the combined, demonstrated better performance as compared to LDpred. For example, in the top 5% of the predicted risk, an Odds Ratio (OR) of 10.49 was observed for DL-others, an OR of 24.13 was observed for DL-known, and an OR of 26.32 was observed for DL-comb, compared to the rest of the 95% of the samples (as compared to 6.29 for LDpred). As another example, in the top 10% of the predicted risk, observed Odds Ratios (OR) were 7.82 for DL-others, 17.03 for DL-known, and 19.25 for DL-comb, compared to 4.35 for LDpred. Within the top 5% and 10% of the DL-comb score, 93.5% and 90.3% were CD patients, respectively. As a comparison, in LDPred algorithm proportion of CD patients were 78.3% and 69.9%, respectively in the top 5% and 10%. The corresponding positive likelihood ratio (LR+) was 2.64 and 2.77 for DL-comb using top 5% and 10% cutoff, top and 2.15 and 2.00 for LDpred, respectively. And the corresponding negative likelihood ratio (LR-) was 0.10 and 0.14 for DL-comb, and 0.34 and 0.47 for LDPred, respectively. These all indicate that the deep learning algorithms may greatly boost the practical potentials of genomic prediction.

TABLE 1

Performance of different algorithms in identifying CD cases in extreme of the predicted risk

| Threshold | Algorithm | N cases / N controls | | OR | p |
|---|---|---|---|---|---|
| | | In extreme | In remaining | | |
| 0.005 | DL-comb | 36/2 | 2807/4566 | 29.28 | $7.78 \times 10^{-13}$ |
| | LDpred | 32/6 | 2811/4562 | 8.66 | $5.64 \times 10^{-9}$ |
| | LD-known | 37/1 | 2806/4567 | 60.22 | $6.41 \times 10^{-14}$ |
| | LD-others | 33/5 | 2810/4563 | 10.72 | $7.20 \times 10^{-10}$ |
| 0.01 | DL-comb | 71/4 | 2772/4564 | 29.22 | $6.85 \times 10^{-24}$ |
| | LDpred | 63/12 | 2780/4556 | 8.60 | $3.10 \times 10^{-16}$ |
| | LD-known | 72/3 | 2771/4565 | 39.54 | $5.87 \times 10^{-25}$ |
| | LD-others | 66/9 | 2777/4559 | 12.04 | $6.37 \times 10^{-19}$ |
| 0.02 | DL-comb | 141/8 | 2702/4560 | 29.74 | $3.41 \times 10^{-46}$ |
| | LDpred | 126/23 | 2717/4545 | 9.16 | $1.05 \times 10^{-31}$ |
| | LD-known | 145/4 | 2698/4564 | 61.32 | $1.56 \times 10^{-50}$ |
| | LD-others | 136/13 | 2707/4555 | 17.60 | $4.73 \times 10^{-41}$ |
| 0.05 | DL-comb | 347/24 | 2496/4544 | 26.32 | $2.44 \times 10^{-111}$ |
| | LDpred | 290/81 | 2553/4487 | 6.29 | $7.30 \times 10^{-59}$ |
| | LD-known | 345/26 | 2498/4542 | 24.13 | $3.27 \times 10^{-109}$ |
| | LD-others | 317/54 | 2526/4514 | 10.49 | $1.29 \times 10^{-81}$ |
| 0.1 | DL-comb | 670/72 | 2173/4496 | 19.25 | $1.50 \times 10^{-206}$ |
| | LDpred | 519/223 | 2324/4345 | 4.35 | $1.24 \times 10^{-77}$ |
| | LD-known | 662/80 | 2181/4488 | 17.03 | $3.78 \times 10^{-198}$ |
| | LD-others | 593/149 | 2250/4419 | 7.82 | $5.47 \times 10^{-133}$ |
| 0.2 | DL-comb | 1238/245 | 1605/4323 | 13.61 | $<4.94 \times 10^{-324}$ |
| | LDpred | 952/531 | 1891/4037 | 3.83 | $8.42 \times 10^{-116}$ |
| | LD-known | 1216/267 | 1627/4301 | 12.04 | $<4.94 \times 10^{-324}$ |
| | LD-others | 1084/399 | 1759/4169 | 6.44 | $1.03 \times 10^{-207}$ |
| 0.5 | DL-comb | 2325/1381 | 518/3187 | 10.36 | $<4.94 \times 10^{-324}$ |
| | LDpred | 1933/1773 | 910/2795 | 3.35 | $8.48 \times 10^{-132}$ |
| | LD-known | 2271/1435 | 572/3133 | 8.67 | $<4.94 \times 10^{-324}$ |
| | LD-others | 2089/1617 | 754/2951 | 5.06 | $4.77 \times 10^{-223}$ |

Importantly, the DL model was trained using the IIBDGC cohort, in which most of the CD patients are adult. Further, the performance of the DL algorithm was evaluated in the RISK cohort, which is an pediatric CD cohort with ages of diagnosis of patients less than 16 years old. Similar performance of the DL algorithm was observed in the RISK study, thereby confirming the DL model's robustness in this independent and heterogenous test cohort.

Interestingly, when examining the extremes of the deep learning scores, the ORs of DL-known and DL-comb were comparable. This indicates that with smartly constructed algorithms, screening for individuals with high disease risk may potentially be flexible. It may be performed based on the overall genetic profile across the genome (and potentially with best prediction accuracy), or alternatively only using a relatively small panel of known variants for a more flexible solution with slightly reduced accuracy. Again, this makes genomic prediction more practical and may have broad clinical impacts, potentially easing the path to clinical translation.

While the DL-others algorithm, only with variants not in LD with known variants, has an AUC of 0.747, which is less than those of the DL-known and DL-comb models, this still represents an improvement over LDpred, which indicates that there are additional variants, probably with weak effects, contributing to the development of this complex disease. This is not surprising given the "missing heritability" in CD and many other complex human traits, and perhaps the study of hundreds of thousands of individuals may be performed to identify the additional individual susceptibility variants. Deep learning score approaches provide an alternative way to 'collapse' those variants to generate meaningful information with currently limited sample sizes. The DL algorithm may also indicate the contribution of each variant to the predicted disease risk score based on the variance importance metrics, which may be viewed as an indication of potential novel genetic loci.

The variance importance metrics of the DL-other model in CD prediction were examined. The variable importance metrics from the DL algorithm indicates the relative importance or contribution of each variable and/or mutation to the overall model, which may be helpful in discovery of novel signals. For the top 500 variants, a meta-analysis was performed incorporating the immunoChip data from the IIBDGC cohort, the CSMC cohort, and the summary statistics from de Lange et al. (de Lange, K. M. et al., "Genome-wide association study implicates immune activation of multiple integrin genes in inflammatory bowel disease," *Nat Genet* 49, 256-261 (2017), which is incorporated by reference herein in its entirety). Of those 500 variants, 11 novel genome-wide signals were identified with a meta-analysis p-value of $5.0 \times 10^{-8}$ (FIGS. 19A-19B).

Several interesting novel variants were identified that are functionally relevant. For example, rs7158822 in the MARK3 gene, involved in ubiquitin recognition39 that may be implicated in intestinal homeostasis and gut inflammation, has an OR of 0.94 (P=2.66E-11) with relative importance of 0.47. Another variant (rs661356) near DOCK8 gene, which may play a critical role in anti-inflammatory macrophage function and intestinal mucosal homeostasis, has an OR of 1.05 (P=4.15E-8) with relative importance of 0.39. In addition to predicting complex disease risk, these findings show that the LD model may be a useful tool in identifying new genetic variants with functional relevance to complex disease pathology. "MARK3" refers to Microtubule Affinity Regulating Kinase 3 (Entrez Gene 4140; Ensembl: ENSG00000075413). "DOCKS" refers to Dedicator Of Cytokinesis 8 (Entrez Gene 81704; Ensembl: ENSG00000107099).

Results: An AUC of 0.788 and 0.841 was observed in the training and validation cohorts respectively for the DL model, which is significantly better than the LDpred model (AUC=0.673 and 0.699, P=2.41E-243 and 5.75E-83 for AUC difference, respectively in training and validation cohorts). People at the extreme of the predicted DL score have a much higher risk of CD compared to the rest of the sample, with an OR of 26.32 in top 5% and 19.25 in top 10%. Within the top 5% and 10% of the DL score, 93.5% and 90.3% are CD patients, respectively. As a comparison, OR is 10.33 in top 5% and 4.35 in top 10% for LDpred algorithm, and the corresponding proportion of CD patients are 78.3% and 69.9%, respectively.

Within CD cases in the validation cohort, the predicted DL score is strongly related to clinical phenotypes: an OR of 3.15 (P=1.18E-8) was observed in B2(stricturing)/B3(penetrating) compared to B1 (non-stricturing, no penetrating disease); and an OR of 2.72 (P=1.12E-5) for the association of DL score with need for surgery. DL score is also strongly associated with disease serological markers including ANCA (OR=0.47, P=6.63E-4), CBir1 (OR=3.30, P=2.73E-9), as well as IgA-ASCA (OR=4.13, P=2.77E-10) and IgG-ASCA (OR=5.54, P=1.55E-14).

Figure 20:
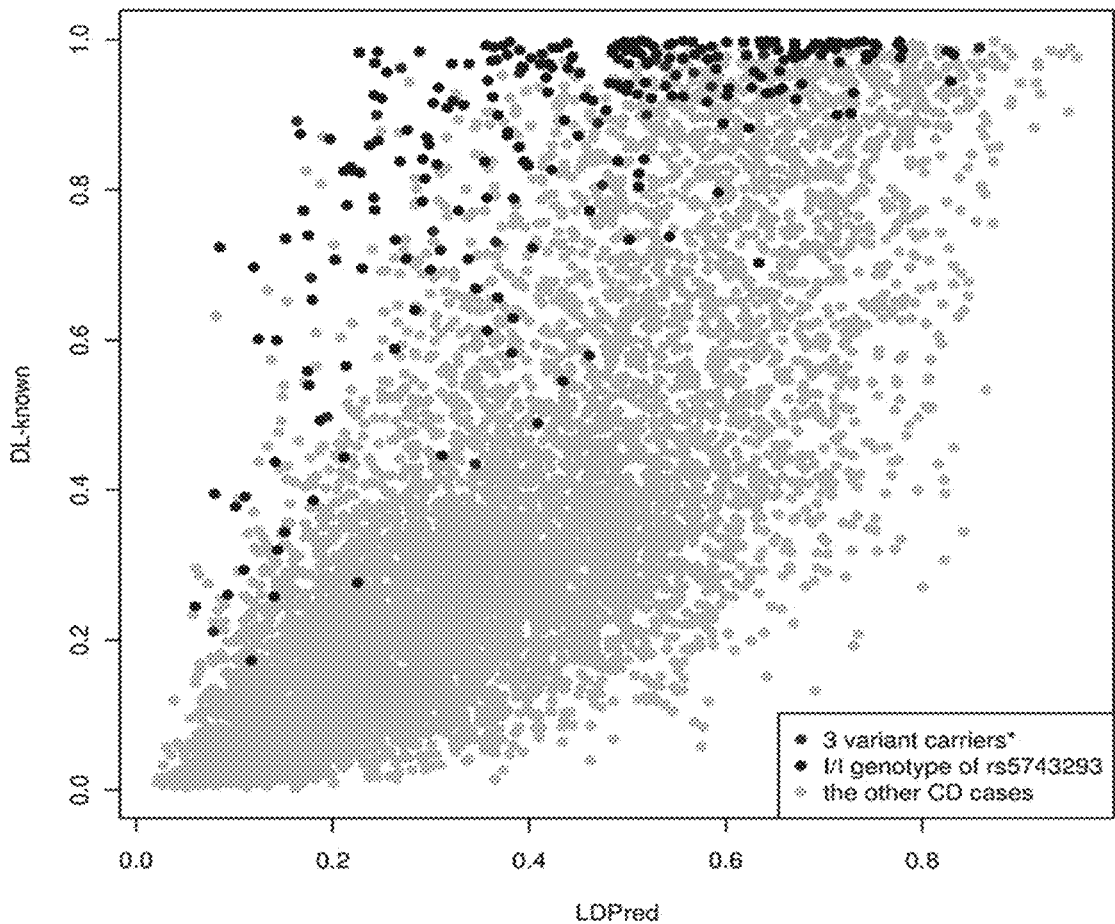
FIG. 20 shows a non-limiting example of a relationship of DL-known score and LDPred score in CD, using the methods and systems disclosed herein. The legend is as follows—
*: the three variants rs5743293 (Leu1007fsinsC in NOD2), rs2066845 (Gly908Arg in NOD2) and rs3116496 (CD28 eQTL variant); DL-known: Deep Learning prediction using known variants and variants in LD with known; LDpred: prediction results using LDPred.

Further, the DL-known score was plotted against the LDPred score in CD patients (FIG. 20). FIG. 20 shows a non-limiting example of a relationship of DL-known score and LDPred score in CD. The legend is as follows—*: the three variants rs5743293 (Leu1007fsinsC in NOD2), rs2066845 (Gly908Arg in NOD2) and rs3116496 (CD28 eQTL variant); DL-known: Deep Learning prediction using known variants and variants in LD with known; LDpred: prediction results using LDPred. As expected in both cases of non-linear effects, all carriers of the three SNP combination, as well as rs5743293 homozygous risk individuals, were in the top-left side of the diagonal with much higher estimated risk in DL-known compared to LDPred (P=2.33E-13 and 1.92E-5, respectively).

Conclusion: With this DL model, individuals with disease risk for an inflammatory disease, such as CD, may be identified using only genetic data, making it a powerful tool for disease early diagnosis and intervention. In some embodiments, the disease is monogenic-like. The utility of the DL model is not limited to predicting complex disease risk for CD. Without being bound by any particular theory, this DL model may be utilized with a wide range of genetic data input (e.g., genetic variants associated with other inflammatory diseases or disorders, such as ulcerative colitis or Rheumatoid arthritis) to predict complex disease risk.

Example 2: Performance of the DL Algorithm and LDpred Approach in the RISK Cohort Further, the trained model was applied in the RISK cohort. The RISK cohort was recruited according to the RISK study, which is an ongoing, prospective observational multi-center collaborative study of pediatric inflammatory bowel disease. Children and adolescents younger than 17 years newly diagnosed with inflammatory bowel disease (IBD) were eligible for enrollment in RISK between November 2008 and June 2012. For each of these subjects, a diagnosis of CD was made based on standard endoscopic, histologic, and radiographic features. A set of 801 CD patients 1633 non-IBD controls from the RISK cohort were included in this analysis. Written informed consent was provided by all parents or caregivers, and written assent was obtained from children as appropriate.

Genotyping of the RISK cohort was performed at laboratories at Emory University and The Feinstein Institute for Medical Research and Cincinnati Children's Hospital Medical Center using ImmunoChip. A similar QC procedure was performed, including assessment of individual and genotype missingness, allele frequencies, deviations from Hardy-Weinberg Equilibrium, gender check, and relatedness.

The performance of the DL algorithm and LDpred approach was examined in the RISK cohort, which is an independent cohort comprising 801 newly-diagnosed pediatric CD patients and 1,633 non-IBD controls genotyped using ImmunoChip. With 107,782 (93.3%) of the 115,519 variants in the training model successfully genotyped, AUC values of 0.753 in DL-known, 0.743 in DL-others, and 0.769 in DL-comb were observed, all of which were significantly higher than that of LDpred (AUC=0.662, p=1.33×10⁻¹⁰, $5.29 \times 10^{-20}$ and $2.48 \times 10^{-28}$ compared to DL-others, DL-known and DL-comb, respectively). Although the DL model was trained in a mostly adult cohort, results in the RISK cohort confirmed its robustness in an independent and heterogenous test cohort.

Part of the reason underlying the superior performance of deep learning algorithm in genomic prediction may be that it may incorporate complex non-linear relationships in the model, which is largely ignored in most main-stream genomic prediction approaches. This is particularly clear in DL-known algorithm in which only known variants (and variants in LD with known variants) were included. A linear prediction model in the training set was built with those variants using step-wise logistic regression, and an AUC of 0.765 was observed in the test cohort, which is much lower than that of DL-known (p=$4.33 \times 10^{-41}$). This result indicates that non-linear genetics effects may contribute significantly to phenotypic variance, which is consistent with observations that high-order interactions contribute significantly to complex traits in model organisms. Although with the nature of DL algorithms it may be challenging to detangle details of the non-linear relationships, as a preliminary step, the potential high-order combination effects were explored within known variants using LAMPlink, and a number of multiple SNP combinations (e.g., 405 3-SNP combinations) were identified that are significantly associated with disease in both the IIBDGC and CSMC cohorts. Further, interesting cases of strong non-linear effects were observed.

Figure 4:
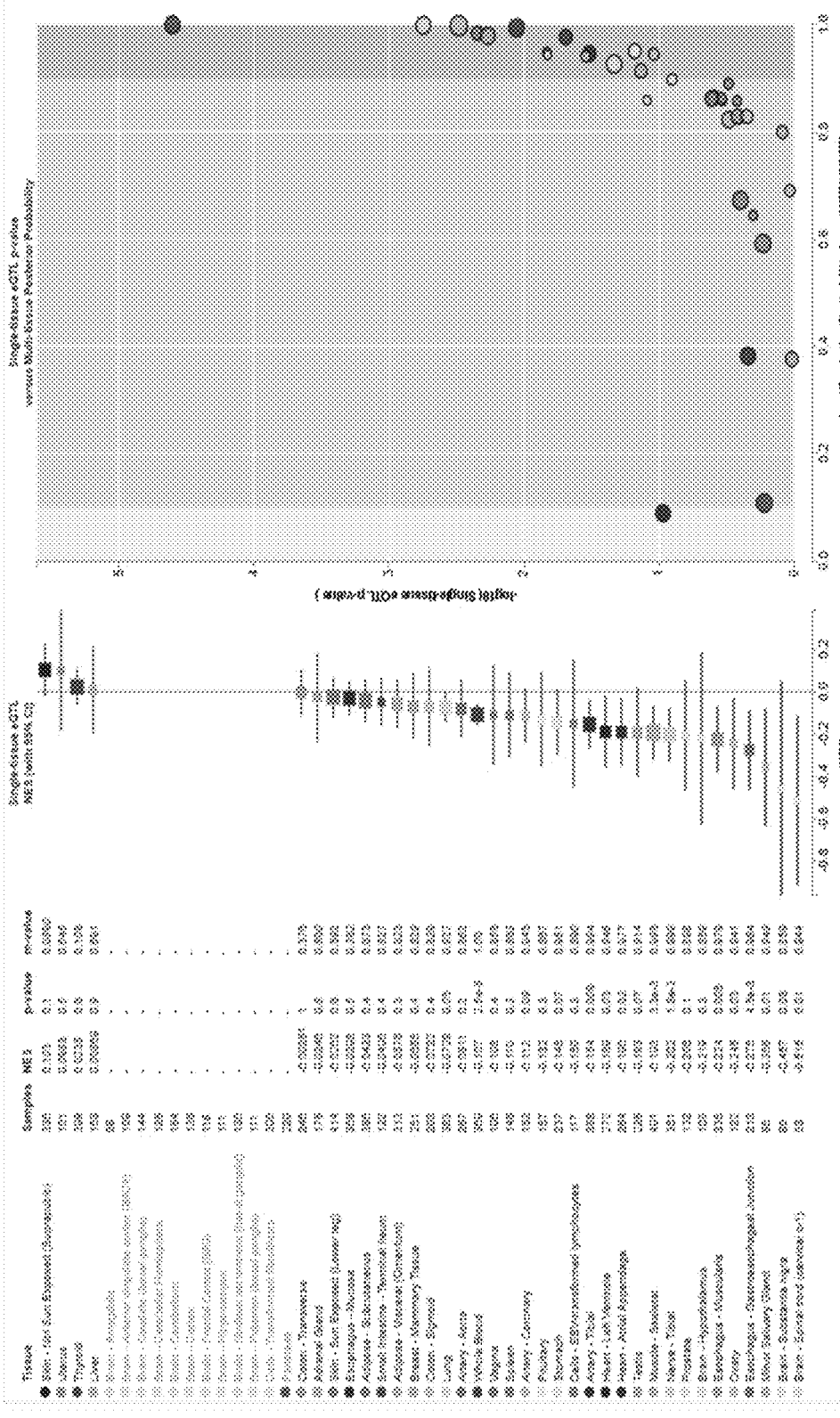
FIG. 4 shows a non-limiting example of observing that carriers of two missense mutations at the nucleotide binding oligomerization domain containing 2 (NOD2) gene (rs5743293 and rs2066845) and rs3116496, an eQTL of cluster of Differentiation 28 (CD28), according to Genotype-Tissue Expression (GTeX), were identified as strongly associated with CD (OR=33.03, p=$1.88 \times 10^{-27}$ in IIBDGC, OR=56.94, p=$3.30 \times 10^{13}$ in CSMC cohort), using the methods and systems disclosed herein.
Figure 5:
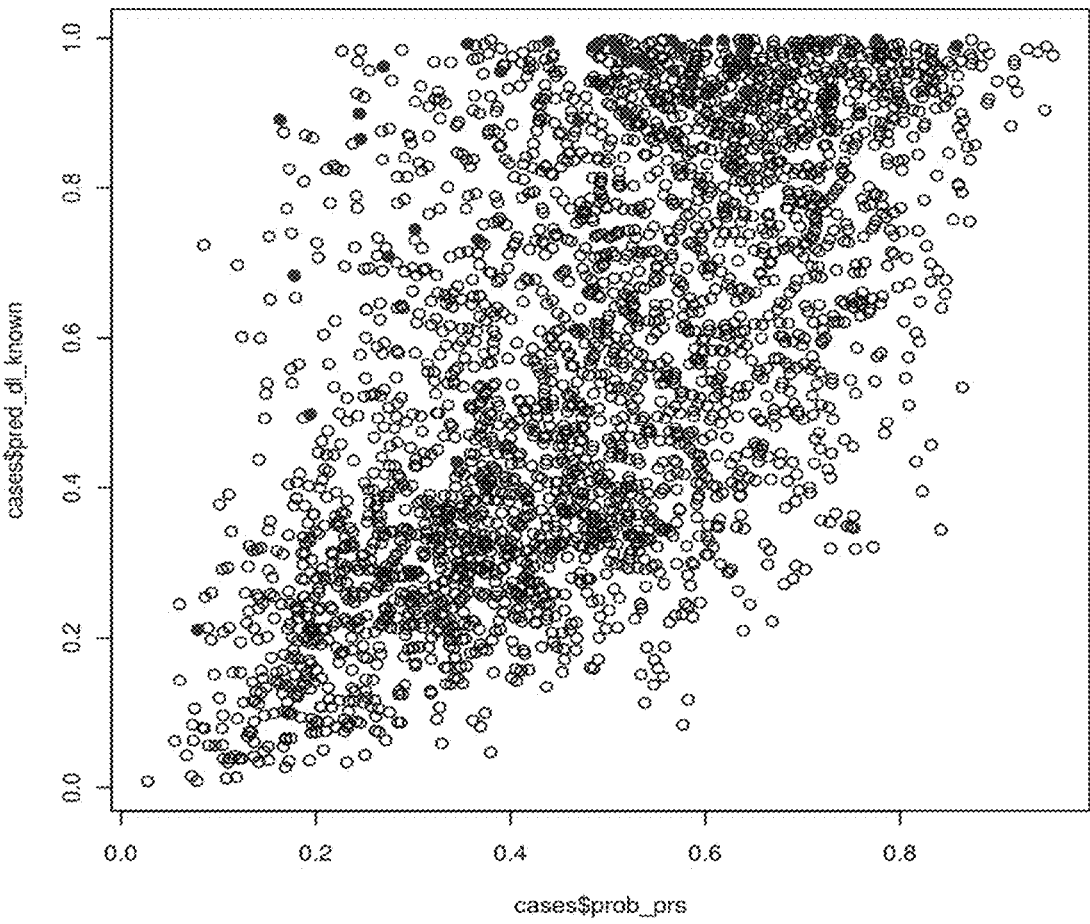
FIG. 5 shows a non-limiting example of observing that in CD cases, carriers of the three mutations had much higher estimated risk in DL-known compared to LDPred and traditional PRS (p=$2.33 \times 10^{13}$ and $1.92 \times 10^{-5}$, respectively), using the methods and systems disclosed herein.

Interestingly, individuals carrying two NOD2 missense mutation (rs5743293 and rs2066845) and rs3116496, an eQTL of CD28, according to GTeX (FIG. 4), were identified as strongly associated with CD (OR=33.03, p=$1.88 \times 10^{-27}$ in IIBDGC, OR=56.94, p=$3.30 \times 10^{-13}$ in CSMC cohort), with more details in Table 2. In CD cases, carriers of the three mutations had much higher estimated risk in DL-known compared to LDPred and traditional PRS (p=$2.33 \times 10^{-13}$ and $1.92 \times 10^{-5}$, respectively) (FIG. 5). As used herein, "eQTL" refers to expression quantitative trait loci, which shows an association of genetic variants with expression levels of mRNA.

As another example, individuals carrying two NOD2 missense mutations (rs5743293/Leu1007fsinsC and rs2066845/Gly908Arg) as well as rs3116496, an eQTL for CD28 (eQTL results from GTeX (gtexportal.org)), had a high risk of CD compared to non-carriers (IIBDGC: OR=30.76, P=8.10E-13; CSMC: OR=37.28, P=4.51E-4; Table 3). LAMPlink analysis also indicated strong deviation from linear additive model for the NOD2 frameshift mutation rs5743293 (Table 4). 271 of the 288 (94.1%) rs5743293 homozygous risk (I/I) individuals in IIBDGC were CD cases, corresponding to an OR of 30.76 (P=2.56E-42) compared to wild type. Consistently, 229 of 234 (97.9%) rs5743293 homozygous risk individuals were CD cases in the CSMC cohort (OR=76.68, P=2.66E-21).

As used herein, "OR" refers to an odds ratio, which quantifies the strength of an association between two events. When OR is greater than 1, the two events are positively correlated; when the OR that is less than 1, the two events are negatively correlated. "P" as used herein refers to p value, which is the statistical significance of an association. A lower p value indicates a stronger statistical significance of the association than a p value that is higher. Carrier status refers to the number of risk variants (0, 1, 2, or 3) carried by subjects of each cohort. "95% CI" refers to a 95% confidence interval.

TABLE 2

Carrier status of Combination 216 (rs3116496, rs2066845, rs5743293) in IIBDGC and Cedars cohorts

| Cedars Cohort 3 vs. 0: OR = 56.95, P = 3.30 × 10⁻¹³ | | | IIBDGC Cohort 3 vs. 0: OR = 33.03, P = 1.88 × 10⁻²⁷ | | |
|---|---|---|---|---|---|
| # of carrier status | CD+ | CD− | # of carrier status | CD+ | CD− |
| 0 | 1312 | 2850 | 0 | 7427 | 14441 |
| 1 | 1183 | 1589 | 1 | 5672 | 8575 |
| 2 | 312 | 128 | 2 | 1029 | 613 |
| 3 | 35 | 1 | 3 | 79 | 4 |

TABLE 3

Association of CD status with a 3-SNP combination (rs5743293, rs2066845, and rs3116496) in IIBDGC and CSMC cohorts

| Carrier status | n. case | n. ctrl | OR | 95% CI | P |
|---|---|---|---|---|---|
| | | | In CSMC Cohort | | |
| 0 | 1312 | 2850 | — | — | — |
| 1 | 1183 | 1589 | 1.43 | 1.27-1.6 | 8.46E−10 |
| 2 | 312 | 128 | 3.53 | 2.77-4.51 | 2.60E−24 |
| 3 | 35 | 1 | 37.28 | 4.94-281.44 | 4.51E−04 |
| | | | In IIBDGC | | |
| 0 | 7427 | 14441 | — | — | — |
| 1 | 5672 | 8575 | 1.26 | 1.2-1.31 | 6.58E−24 |
| 2 | 1029 | 613 | 3.23 | 2.91-3.59 | 2.42E−105 |
| 3 | 79 | 4 | 39.68 | 14.49-108.69 | 8.10E−13 |

TABLE 4

Deviation from linear additive model for NOD2 mutation rs5743293 in IIBDGC and CSMC cohort

| NOD2 genotype | n. case | n. ctrl | OR | 95% CI | P |
|---|---|---|---|---|---|
| | | | in CSMC Cohort | | |
| D/D | 2307 | 4377 | — | — | — |
| I/D | 307 | 186 | 2.90 | 2.36-3.58 | 1.39E−23 |
| I/I | 229 | 5 | 76.68 | 31.25-188.17 | 2.66E−21 |
| | | | in IIBDGC | | |
| D/D | 13116 | 22771 | — | — | — |
| I/D | 1888 | 1149 | 3.00 | 2.78-3.25 | 7.85E−169 |
| I/I | 271 | 17 | 30.76 | 18.8-50.35 | 2.56E−42 |

Example 3: Association of Predicted Risk Scores with Clinical Characteristics of CD Further, the association of predicted risk scores with clinical characteristics of CD was examined (Table 3). Overall, the risk score calculated using DL-comb has the strongest association with disease severity, disease location, and need for surgery. For example, in disease location analysis of L1(Ileal-only location) versus L2 (Colon-only location), OR values of 6.41 (95% confidence interval (CI) of [3.53-11.64], p=1.04×10$^{-9}$) for DL-comb score, 4.86 (95% CI of [2.92-8.08], p=1.18×10$^{-9}$) for DL-known, 2.07 (95% CI of [1.39-3.07], p=3.12×10$^{-4}$) for DL-others, and 3.75 (95% CI of [1.88-7.45], p=1.69×10$^{-4}$) for LDpred.

TABLE 5

Association of predicted disease risk with clinical characteristics of CD

| Outcome | Algorithm | N | OR | 95% CI | P |
|---|---|---|---|---|---|
| B2 vs. B1 | DL-comb | 1755 | 3.98 | 2.26-7.01 | $1.68 \times 10^{-6}$ |
| | DL-known | 1755 | 1.78 | 1.20-2.64 | $4.23 \times 10^{-3}$ |
| | DL-others | 1755 | 1.99 | 1.44-2.74 | $2.58 \times 10^{-5}$ |
| | LDpred | 1755 | 2.90 | 1.79-4.70 | $1.47 \times 10^{-5}$ |
| B3 vs. B1 | DL-comb | 1720 | 3.43 | 2.10-5.60 | $8.29 \times 10^{-7}$ |
| | DL-known | 1720 | 2.48 | 1.66-3.69 | $8.28 \times 10^{-6}$ |
| | DL-others | 1720 | 2.14 | 1.54-2.99 | $6.64 \times 10^{-6}$ |
| | LDpred | 1720 | 2.27 | 1.3-3.97 | $3.86 \times 10^{-3}$ |
| B2B3 vs. B1 | DL-comb | 2343 | 3.15 | 2.13-4.76 | $1.18 \times 10^{-8}$ |
| | DL-known | 2343 | 2.10 | 1.52-2.94 | $8.21 \times 10^{-6}$ |
| | DL-others | 2343 | 2.07 | 1.58-2.70 | $9.31 \times 10^{-8}$ |
| | LDpred | 2343 | 3.03 | 1.92-4.76 | $2.24 \times 10^{-6}$ |
| L1 vs. L2 | DL-comb | 1028 | 6.41 | 3.53-11.64 | $1.04 \times 10^{-9}$ |
| | DL-known | 1028 | 4.86 | 2.92-8.08 | $1.18 \times 10^{-9}$ |
| | DL-others | 1028 | 2.07 | 1.39-3.07 | $3.12 \times 10^{-4}$ |
| | Dpred | 1028 | 3.75 | 1.88-7.45 | $1.69 \times 10^{-4}$ |
| L3 vs. L2 | DL-comb | 1770 | 4.74 | 2.88-7.81 | $9.48 \times 10^{-10}$ |
| | DL-known | 1770 | 3.32 | 2.15-5.13 | $5.72 \times 10^{-8}$ |
| | DL-others | 1770 | 2.26 | 1.60-3.19 | $3.45 \times 10^{-6}$ |
| | LDpred | 1770 | 2.28 | 1.26-4.12 | $6.48 \times 10^{-3}$ |
| L1L3 vs. L2 | DL-comb | 2332 | 5.10 | 3.23-8.33 | $1.55 \times 10^{-11}$ |
| | DL-known | 2332 | 3.71 | 2.44-5.56 | $7.08 \times 10^{-10}$ |
| | DL-others | 2332 | 2.18 | 1.56-3.03 | $2.88 \times 10^{-6}$ |
| | LDpred | 2332 | 2.65 | 1.52-4.76 | $6.88 \times 10^{-4}$ |
| Surgery | DL-comb | 2461 | 2.72 | 1.74-4.25 | $1.12 \times 10^{-5}$ |
| | DL-known | 2461 | 1.84 | 1.34-2.54 | $1.81 \times 10^{-4}$ |
| | DL-others | 2461 | 1.60 | 1.24-2.08 | $3.64 \times 10^{-4}$ |
| | LDpred | 2461 | 2.26 | 1.54-3.31 | $3.38 \times 10^{-5}$ |

A classification of CD phenotypes is used in Table 5. A "B" refers to a behavior, wherein "B1" refers to non-stricturing, non-penetrating; "B2" refers to stricturing; "B3" refers to penetrating. An "L" refers to a location, wherein "L1" refers to ileal; "L2" refers to colonic; "L3" refers to ileocolonic.

A strong association of the DL score with clinical phenotypes of CD was observed. Interestingly, although the prediction performance of DL-others was worse than DL-known, the association of risk score from DL-others with disease severity may be comparable or sometimes, stronger. For example, when comparing B2 (stricturing disease) and B3 (internal penetrating disease) to B1 (non-stricturing non-penetrating disease), the OR of DL-known score was 2.10 (95% CI of [1.52-2.94], p=8.21×10$^{-6}$) and that of DL-others score was 2.07 (95% CI of [1.58-2.70], p=3.12× 10$^{-4}$). This result suggests that although the unknown genetic variants contribute weakly to CD pathogenesis, they may have a relatively stronger effect on disease severity. This indicates shared but different underlying genetic mechanisms of disease pathogenesis and progression.

Also contemplated herein, are DL models that account for demographic, behavioral, as well as other clinical relevant factors (e.g., duration of disease and treatment information) to further tailor prediction for clinical behavior and prognosis of CD. Predictions for clinical behavior and prognosis of CD may be leveraged to develop highly personalized treatment strategy and intervention, transforming CD clinical practice.

Current analysis was based on ImmunoChip, a platform enriched with immune-disease related variants. Further studies exploring performance of the deep learning algorithm in genome-wide data may be performed. Environmental factors may be incorporated into the prediction models to further improve the prediction performance, such as smoking information for the cases and controls in the training and test sets. Further, further development of the proposed approach toward improved differential diagnosis of CD may improve the prediction model, in particular with inflammatory diseases with similar clinical presentations such as ulcerative colitis, irritable bowel syndromes, and intestinal tuberculosis.

In this study, a prediction model of CD risk was constructed using Deep Learning algorithms using genetic data from the IIBDGC cohort. A deep learning (DL)-based algorithm was applied to predict disease status of Crohn's Disease (CD), and its performance was compared to the popular LDPred approach. A training model was built using a convolutional neural network (CNN) with 47,425 individuals in the IIBDGC ImmunoChip cohort. The performance of this model was validated in independent cohorts from CSMC and in a pediatric inception cohort. In an independent test cohort of 7,411 individuals, a non-trivial improvement in prediction performance of DL was observed, with an Area Under the Curve (AUC) value of 0.841, in comparison to 0.699 using the LDPred approach. This is among the best performance of risk prediction of complex human diseases using genetic data, and a significant improvement on the popular LDPred approach. The improvement in prediction accuracy from the DL approach led to greatly enriched CD cases in the extreme of the DL score, with an OR of 19.25 in the top 10%, and an OR of 26.32 for DL compared to 6.29 for LDPred approach in top 5%. This finding indicates that ostensibly "healthy" individuals in the top extremes of DL score may benefit from screening for evidence of CD, and may provide an opportunity to study high-risk patients with preventive strategies, as may be shown in a number of immune-mediated diseases. By producing such a high Odds Ratio (OR), DL-based approaches may enable cost-effective genetic screening (e.g., to a general population or a high-risk population such as individuals with family history and/or symptoms of CD) in the extremes of DL prediction. The DL-based prediction approaches disclosed herein may be expanded to other complex diseases, and may promote early detection and prevention of complex human diseases, such as inflammatory disease (e.g., IBD) conditions.

Using only the known variants, the DL based algorithm (DL-known) achieved an AUC of 0.826. Further analyses indicate that in the known variants, the improved performance of the DL score is likely due to its ability to incorporate complex non-linear relationships of associated disease variants with disease phenotype. Moreover, after excluding known variants (and variants in LD with known), an AUC of 0.743 was observed for DL algorithm (DL-other). Variance importance metrics of the DL-other algorithm identified 32 novel CD variants that reached genome-wide significance in a meta-analysis incorporating 137,216 individuals. DL predicted risk score is also strongly associated with disease clinical phenotypes of CD including disease location, severity and need for surgery. The corresponding prediction algorithm is available as a free package (GeneticDL) in R.

The superior performance of Deep Learning algorithm in genomic prediction is partly due to the fact that it may incorporate complex non-linear causal effects, which are largely ignored in most mainstream genomic prediction approaches. This is particularly clear with the dominant performance of the DL-known algorithm in which only known variants (and variants in LD with known variants) were included. Although it is challenging to detangle details of the non-linear relationships given the nature of DL algorithms, the potential high-order combination effects within known variants were examined using LAMPlink. Interesting deviations from linear additive model were identified, including the combination effects of NOD2 and CD28 mutations, as well as the recessive model with the NOD2 frameshift mutation alone. Functional work may demonstrate that NOD2 and CD28 may act synergistically to induce profound T-cell proliferation, indicating a potential biological mechanism for the observed non-linear effects. All the individuals that were affected by the potential deviation from linear effects have much higher predicted risk in DL in comparison to LDPred, which strongly indicates that the performance of DL prediction may be partially explained by its ability to capture non-linear causal effects. This further demonstrates that non-linear genetics effects may contribute significantly to phenotypic variance of complex diseases such as CD, consistent with findings that higher-order interactions contribute significantly to complex traits in model organisms.

A Dense Neural Network analysis using the IIBDGC CD ImmunoChip dataset may be performed. One factor that may affect the performance of the Machine Learning approaches is the data QC procedures. In this study, stringent QC procedures were applied to the training dataset, resulting in a relatively smaller number of SNPs considered (115,519 in the model). In spite of that, better overall performance was achieved using the Deep Learning Model. This difference may be attributed to the following details in the design and algorithms which enabled significant technical improvements to the Deep Learning models. First, although studies may generally use Neural Network-based algorithms in prediction, the use of the CNN algorithm was particularly advantageous, because the CNN automatically includes two data pre-processing layers (Convolutional Layer and Pooling Layer) that perform much of the computational heavy lifting before the fully-connected layers. As a comparison, a manual SNP preselection step based on single-SNP level statistics may be performed in typical Neural Network-based algorithms to reduce the dimension of data, which may potentially lead to loss of information. Second, intensive tuning of the hyperparameters was performed in the Deep Learning Model, rather than using arbitrarily selected numbers of neurons and/or layers. Tuning of the parameters in Deep Learning Models may have important impact on performance of the models. Third, Deep Learning models were constructed separately on known SNPs (as well as SNPs in LD, DL-known) and the rest of ImmunoChip (DL-others), rather than fitting all the pre-selected SNPs into the machine learning models; as a result, a superlearner (DL-comb) was constructed by combining the two resulting models.

The analysis results demonstrated consistently observed patterns of deviation from simple additive models in both training and the independent test cohort, which strongly indicates the advantages of incorporating non-linear effects in Deep Learning models for prediction of complex diseases such as CD.

Deep Learning-based algorithms were effectively utilized to predict CD risk using genetic data. Results demonstrated that this algorithm significantly increased the prediction accuracy, and that the predicted disease risk is associated with disease clinical characteristics. With decreasing costs and likely increased availability of next-generation sequencing data that are coupled to electronic health records, results such as these highlight opportunities for the clinical utility of large-scale genomic data for common inflammatory diseases. Further, ethical frameworks and mechanisms to incorporate advances in genomic medicine for complex diseases into clinical practice may be developed.

Example 4: Using DeepLearning and Genetic BigData to Predict CD

Figure 6:
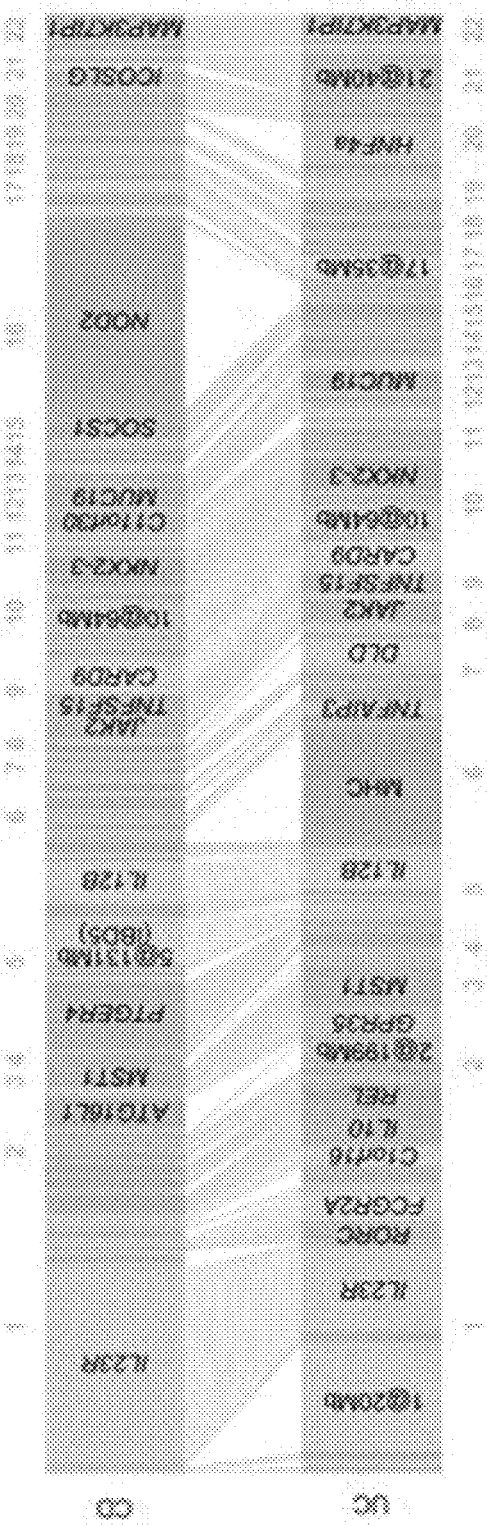
FIG. 6 shows a non-limiting example of more than 200 known genetic loci identified in IBD.
Figure 7:
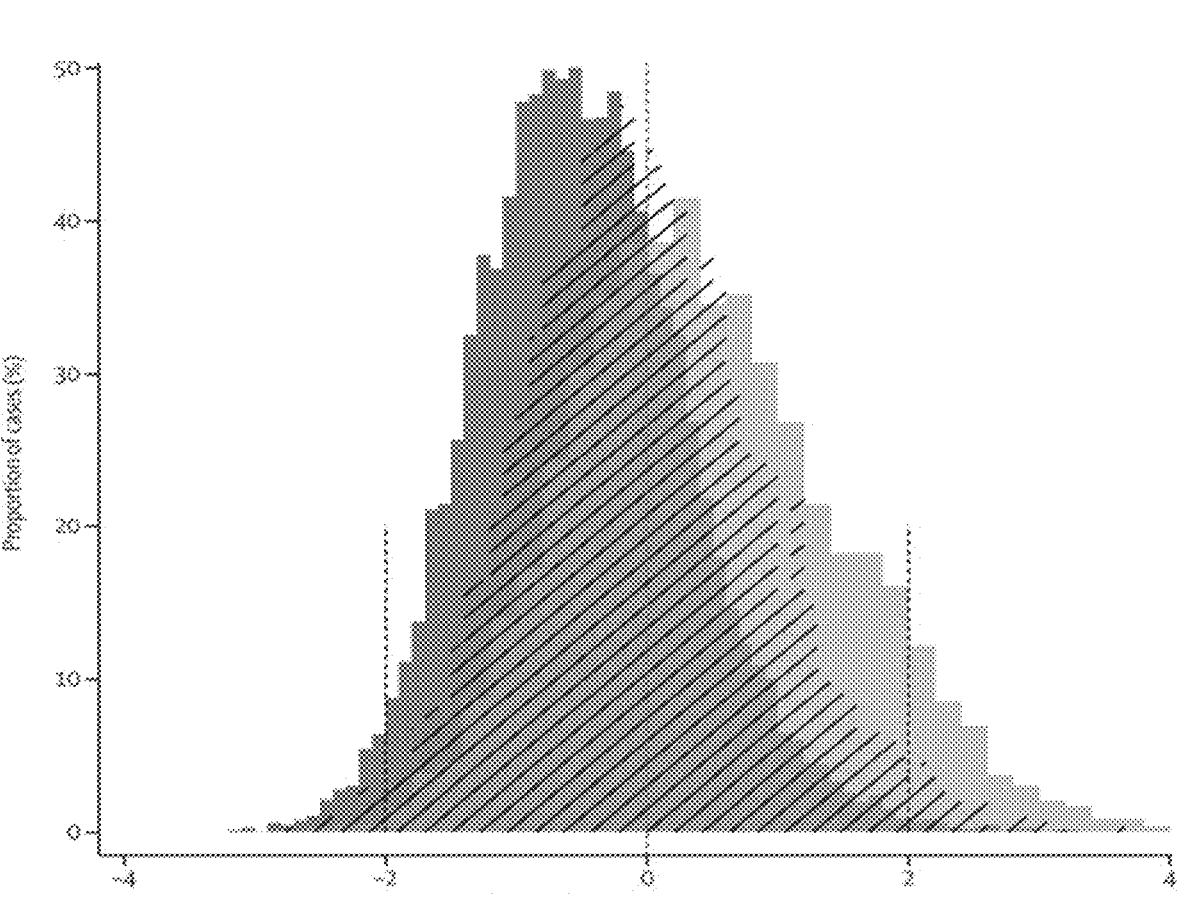
FIG. 7 shows a non-limiting example of polygenetic risk score (PRS) based on known variants from the known genetic loci identified in IBD, for subjects with CD disease (left) and subjects with UC (right).

FIG. 6 shows a non-limiting example of more than 200 known genetic loci identified in IBD. FIG. 7 shows a non-limiting example of polygenetic risk score (PRS) based on those known variants, for subjects with CD disease (left) and subjects with UC (right), which may provide insightful information. For example, IBD PRS may separate ileal CD, colonic CD, and UC.

FIG. 8 shows a non-limiting example of PRS (e.g., constructed using LDPred) being used to identify risk comparable to monogenic mutations. PRS may be constructed based on a linear combination of genetic effects $\overline{Y}=\Sigma\beta x_i$, which is a traditional way of risk prediction.

However, improved ways of predicting and calculating prediction values may be obtained using, for example, deep learning approaches. These deep learning approaches may beat linear model-based prediction in many realistic problems, may handle BigData (large data sets), and may deal with non-linear causal effects. Generally, deep learning refers to part of the machine learning field of learning representations of data, which may be exceptionally effective at learning patterns.

Figure 9:
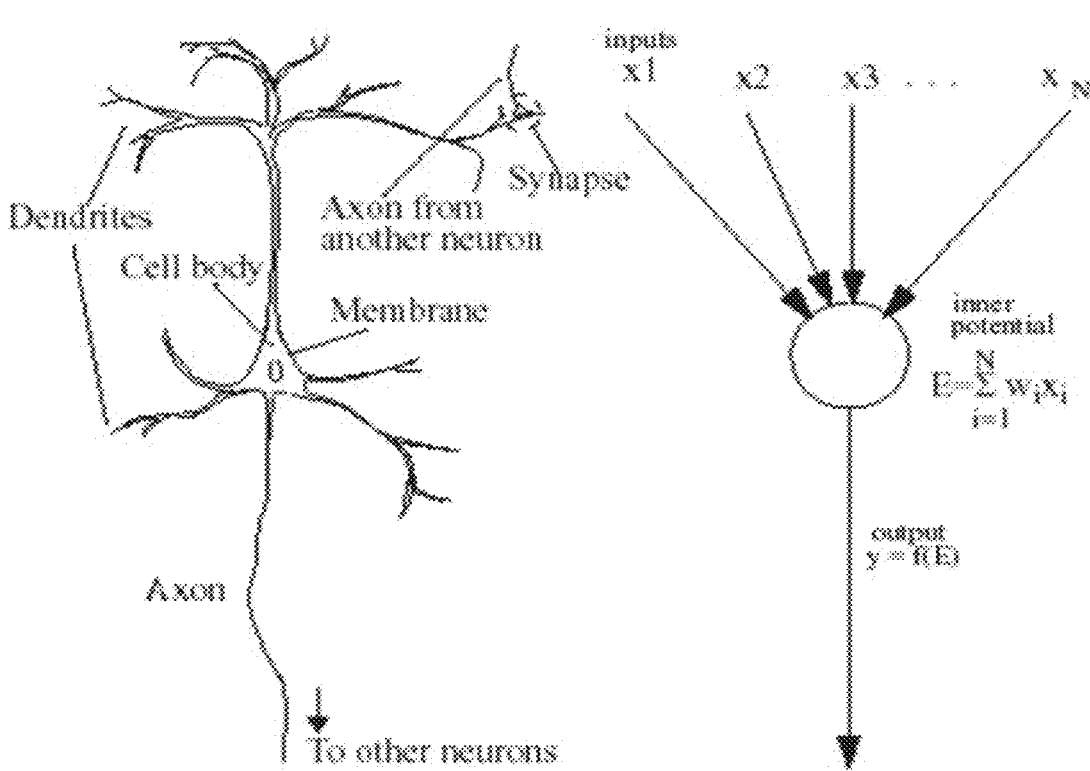
FIG. 9 shows a non-limiting example of a DeepLearning algorithm based on neural networking (similar to a brain's neurons), using the methods and systems disclosed herein.
Figure 10:
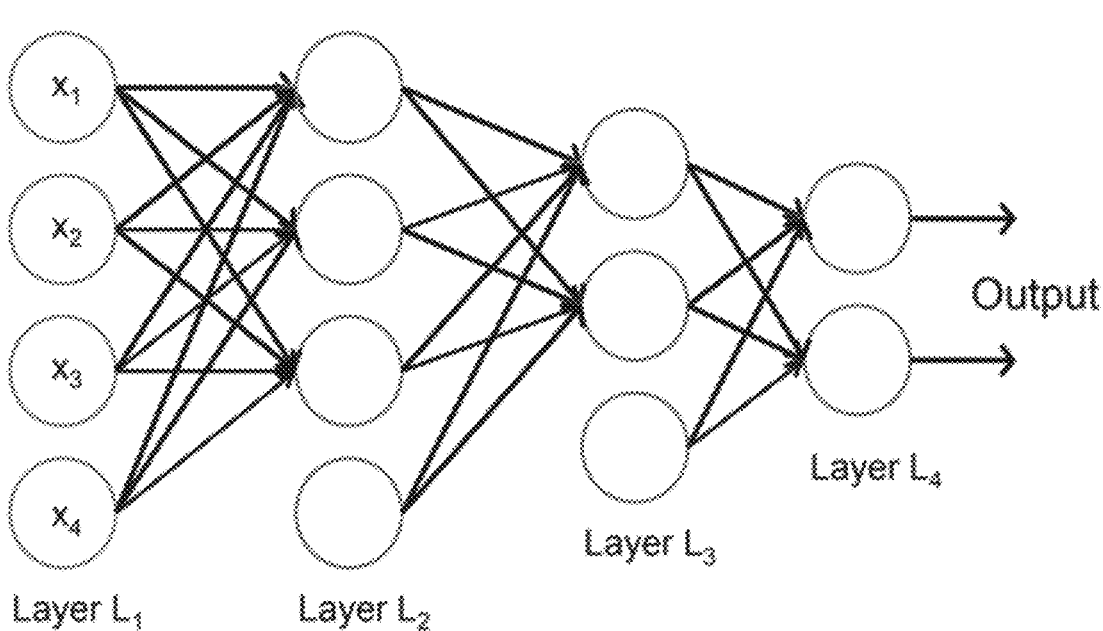
FIG. 10 shows a non-limiting example of DeepLearning algorithms using deep layers of neurons having an input layer, an output layer, and multiple intermediate layers between the input and output layers, using the methods and systems disclosed herein.
Figure 12A:
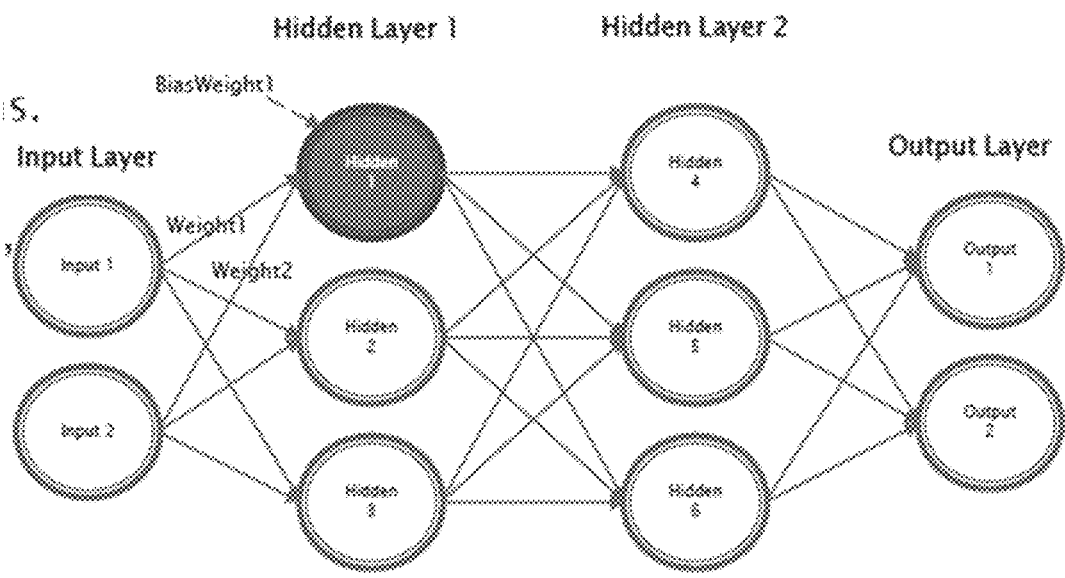
FIG. 12A-12B show non-limiting examples of forward propagation (FIG. 12A) and backpropagation (FIG. 12B) of a DeepLearning algorithm, using the methods and systems disclosed herein.
Figure 12B:
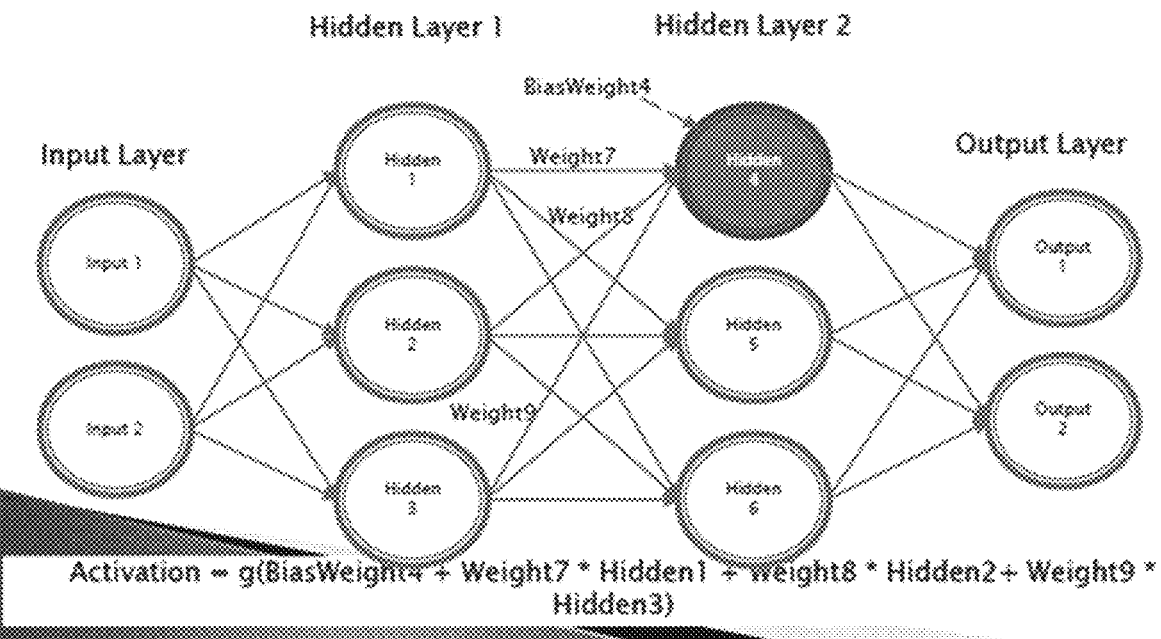

FIG. 9 shows a non-limiting example of a DeepLearning algorithm based on neural networking (similar to a brain's neurons), using the methods and systems disclosed herein. FIG. 10 shows a non-limiting example of DeepLearning algorithms using deep layers of neurons having an input layer, an output layer, and multiple intermediate layers between the input and output layers, using the methods and systems disclosed herein. FIG. 11 shows a non-limiting example of activation functions (e.g., fixed mathematical operations) that may be used in DeepLearning algorithms, such as sigmoid, tanh, ReLU, leaky ReLU, maxout, and ELU, using the methods and systems disclosed herein. FIGS. 12A-12B shows a non-limiting example of forward propagation and backpropagation of a DeepLearning algorithm, using the methods and systems disclosed herein. During the forward propagation stage (FIG. 12A), features are input into the network and fed through the subsequent layers to produce the output activations. However, the error of the network can be calculated only at output units but not in the middle/hidden layers. In order to update the weights to optimal, the network errors are propagated backwards through its layers (FIG. 12B).

DL scores were used to predict CD status, using the methods and systems disclosed herein. Cohorts of patients from the International IBD Genetic Consortium (IIBDGC) were used, including 13,523 CD cases, and 33,902 population based non-IBD controls. All subjects from Cedars cohort were excluded, and used as a training dataset. Also, cohorts of patients from the Cedars IBD cohort were used, including 2,843 CD and 4,568 non-IBD controls. These were Independent European ancestry individuals only, and used as an external validation dataset. Both cohorts were genotyped using ImmunoChip, with 115,519 variants available in both cohorts, and 1,403 variants that are known or in LD with known loci (r2>0.2). Features used in the analysis included known loci/variants in LD with known (DL_known) and the other variants (DL_others). A convolutional neural network was used in prediction, with prediction separately for each group of features, a 5-fold cross-validation for training set, and grid search used to tune parameters in the CNN models. Predictions from different features were combined with stacking (DL_comb), with 5-fold validation. Performance was compared to the LDPred based PRS, which is a popular approach for genetic risk prediction. As shown in FIG. 2, performance of the prediction models (DL known, DL_others, and DL_comb) were all superior to LDPred, as measured by AUC values. Further, Table 1 shows a monogenic level of risk in extreme of the DL score (e.g., as indicated by a level of risk in the top 0.01%, top 0.02%, or top 0.05%) as well as a monogenic level of risk even when the DL score is not so extreme (e.g., as indicated by a level of risk in the top 0.1%, top 0.2%, or top 0.5%). Table 4 shows DL score and association with clinical phenotypes. FIG. 13 shows DL score and association with serologies (within cases). As used herein, "ANCA" refers to antineutrophil cytoplasmic antibodies; "Cbir1" refers to anti-flagellin (CBir1) antibodies; "I2" refers to anti-I2 antibody; "ASCA" refers to anti-*Saccharomyces cerevisiae* antibodies; and "OmpC" refers to anti-outer membrane porin C (anti-OmpC). Immunoglobulin classes referred to in FIG. 13 include immunoglobulin A (IgA) and immunoglobulin G (IgG).

Figure 14:
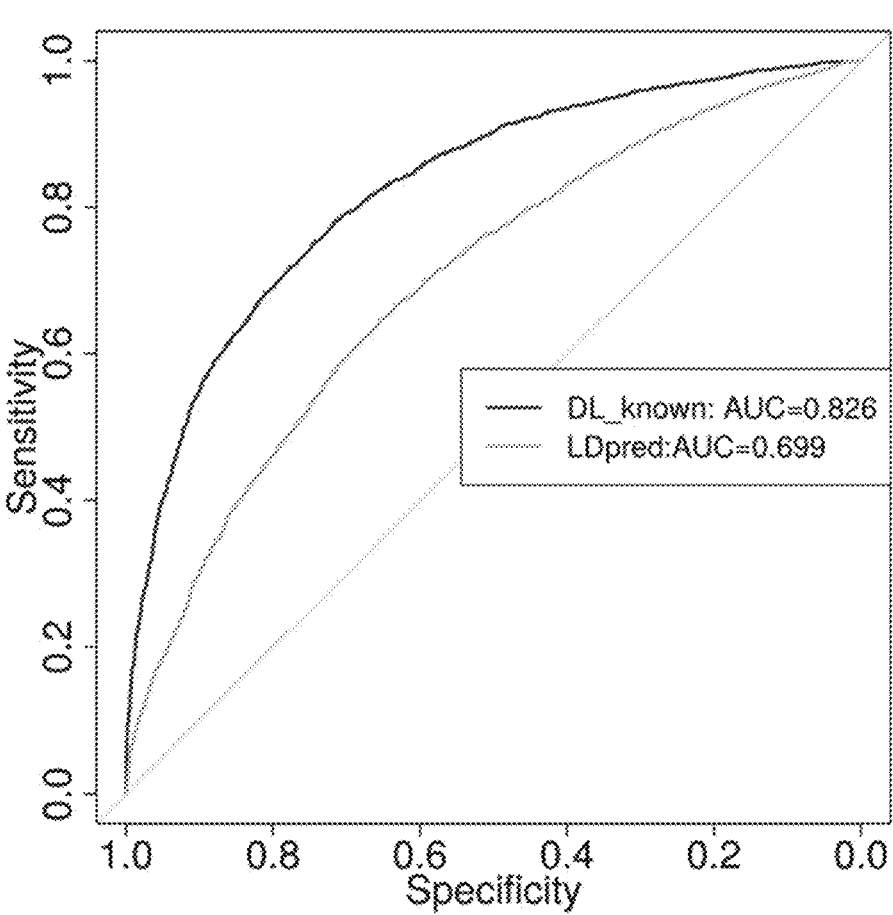
FIG. 14 shows a non-limiting example of DL algorithms having superior performance (e.g., as measured by AUC) compared to LDpred, using the methods and systems disclosed herein.

FIG. 14 shows a non-limiting example of DL algorithms having superior performance (e.g., as measured by AUC) compared to LDpred, using the methods and systems disclosed herein. This may be due to non-linear effects among known variants, which may be accounted for by the DL algorithms.

In some embodiments, LAMPlink was applied to compare disease risk in carriers of combinations of variants vs. the rest of the population. More than 400 3-variant combinations were identified using LAMPlink.

Figure 16:
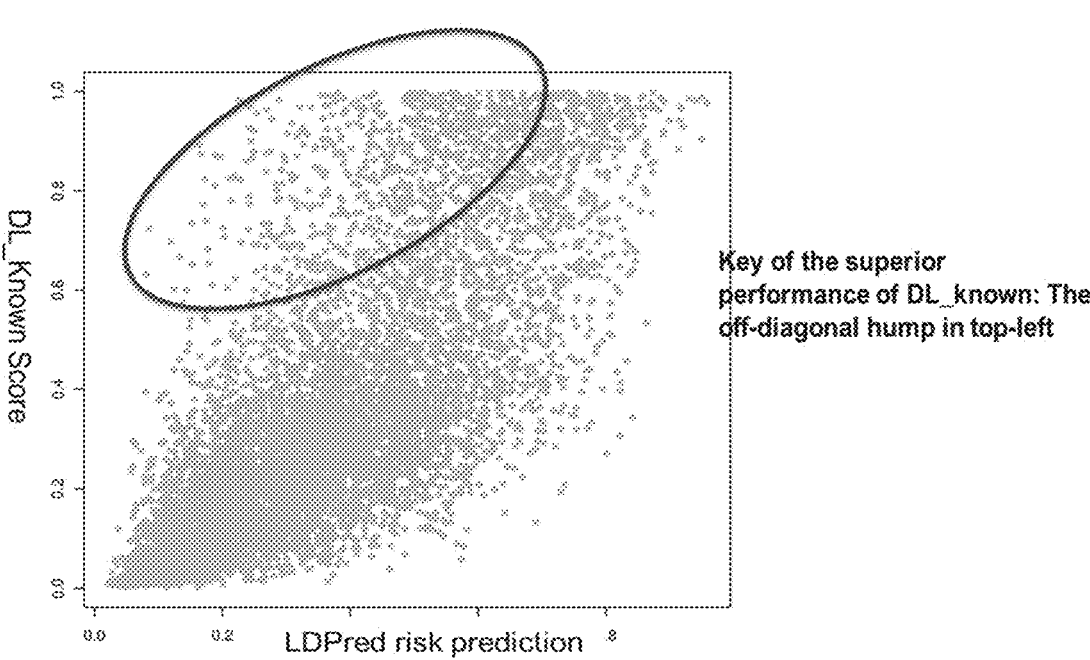
FIG. 16 shows a non-limiting example of superior performance of the DL_known score vs. LDpred PRS, using the methods and systems disclosed herein.

Some combinations indicate non-linear effects, as indicated by Table 2. This was observed in combination 2237 (imm_2_204302757 (an eQTL of CD28), imm_16_49314041 (the NOD2 frameshift mutation), and rs5743293 (NOD2 SNP12; LoF mutation)). FIG. 16 shows a non-limiting example of data results that indicate deviations from a linear additive model, using the methods and systems disclosed herein.

FIG. 16 shows a non-limiting example of superior performance of the DL_known score vs. LDpred PRS, using the methods and systems disclosed herein. The key of the superior performance of DL known is indicated by the off-diagonal hump in the top-left of the plot.

Figure 17:
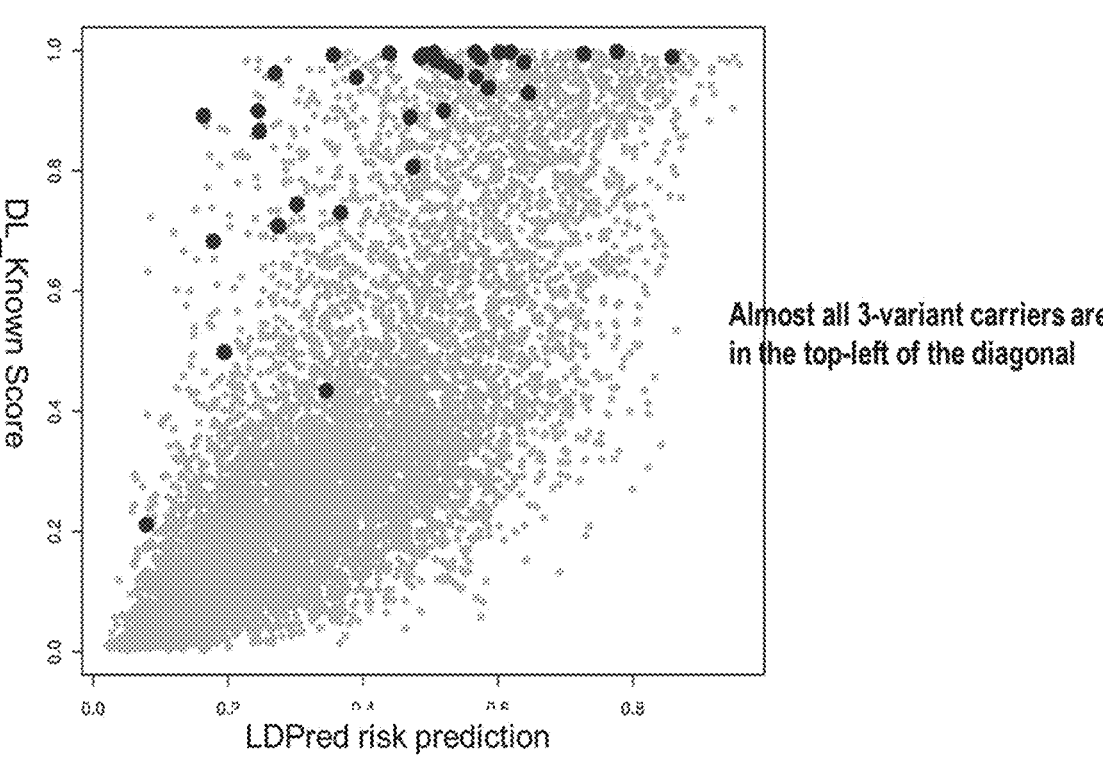
FIG. 17 shows a non-limiting example of superior performance of the DL_known score vs. LDpred PRS in 3-variant carriers (NOD2/CD28 combo), using the methods and systems disclosed herein.

FIG. 17 shows a non-limiting example of superior performance of the DL_known score vs. LDpred PRS in 3-variant carriers (NOD2/CD28 combo), using the methods and systems disclosed herein. Almost all 3-variant carriers are in the top-left of the diagonal of the plot.

Figure 18:
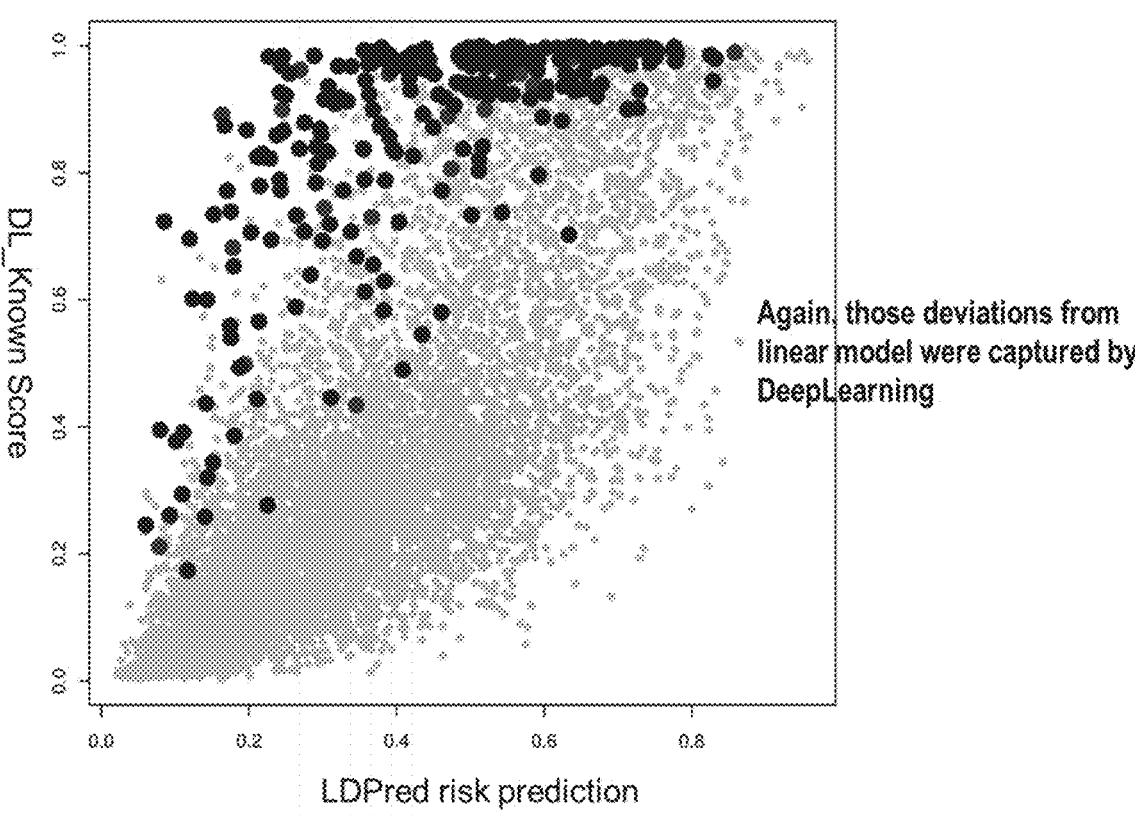
FIG. 18 shows a non-limiting example of superior performance of the DL_known score vs. LDpred PRS in cases of homo of NOD2 frameshift, using the methods and systems disclosed herein.

FIG. 18 shows a non-limiting example of superior performance of the DL_known score vs. LDpred PRS in cases of homo of NOD2 frameshift, using the methods and systems disclosed herein. Again, those deviations from the linear model were captured by the DeepLearning algorithm.

In summary, an improved prediction model of CD status may be developed based on genetic data, using DeepLearning approaches. There is a monogenic level of risk in extreme of DL score. Also, DL score has a strong association with clinical characteristics. DeepLearning approaches demonstrate superior performance to LDpred, probably due to capturing the complex non-linear effects of causal variants, indicating there may be much more than linear additive effects in complex diseases.

Example 5: Convolutional Neural Network Models

Using systems and methods of the present disclosure, convolutional neural network (CNN) prediction models were constructed. The CNN models comprise alternate layers of convolution and pooling followed by a fully connected layers (output) at the end. Batch normalization and dropout are also incorporated to optimize the performance of the CNN.

The convolutional layer may comprise a set of convolutional kernels where each neuron acts as a kernel. The convolutional kernel works by dividing the data into small slices which helps in extracting feature motifs. The kernel convolves using a specific set of weights by multiplying its elements with the corresponding elements of the receptive field. The convolution operation may be expressed by the following expression:

$$f_l^k(p, q) = \sum_c \sum_{x,y} i_c(x, y) e_l^k(u, v)$$

Here, $i_c(x,y)$ is an element of the input data $i_c$, which is element wise multiplied by $$e_l^k(u, v)$$

index of the kth convolutional kernel $k^l$ of the lth layer. The output feature-map of the kth convolutional operation may be expressed by the following expression:

$$F_l^k = [f_l^k(1, 1), \dots, f_l^k(p, q), \dots, f_l^k(P, Q)]$$

The CNN may comprise a pooling layer to perform pooling or down-sampling. Feature motifs, which result as an output of convolution operation, may occur at different locations in the data. Once features are extracted, its exact location becomes less important as long as its approximate position relative to others is preserved. Pooling or down-sampling is a local operation that sums up similar information in the neighborhood or proximity of the receptive field and outputs the dominant response within this local region. This operation may be expressed by the following expression:

$$Z_l^k = \varphi_p(F_l^k)$$

Here $$Z_l^k$$

represents the pooled feature-map of the lth layer for the kth input feature-map $$F_l^k,$$

whereas $\varphi_p$ defines the type of pooling operation. The use of the pooling operation helps to extract a combination of features, which are invariant to translational shifts and small distortions. A reduction in the size of feature-map to invariant feature set not only regulates the complexity of the network, but also helps in increasing the generalization by reducing overfitting. Max, Average, and/or Overlapping may be used as the pooling formulation in model optimization.

The CNN may comprise an activation function, which serves as a decision function and helps in learning of intricate patterns. The selection of an appropriate activation function may accelerate the learning process. The activation function may be defined using the following expression:

$$T_l^k = \varphi_a\left(F_l^k\right)$$

Here, $$F_l^k$$

is an output of a convolution, which is assigned to activation function $\varphi_a$ that adds non-linearity and returns a transformed output $$T_l^k$$

for the lth layer. Activation functions including sigmoid, tanh, maxout, and ReLU may be evaluated for selection when tuning or optimizing the neural network.

Batch normalization may be performed on the CNN to address the issues related to the internal covariance shift within feature-maps. The internal covariance shift is a change in the distribution of hidden units' values, which slows down the convergence (by forcing learning rate to small value) and requires careful initialization of parameters. Batch normalization for a transformed feature-map $$F_l^k$$

may be calculated using the following expression:

$$N_l^k = \frac{F_l^k - \mu_B}{\sqrt{\sigma_B^2 + \varepsilon}}$$

Here, $$N_l^k$$

represents normalized feature-map, $$F_l^k$$

is the input feature-map, and $\mu_B$ and $$\sigma_B^2$$

represent mean and variance of a feature-map for a mini batch, respectively. In order to avoid division by zero, $\varepsilon$ is added for numerical stability. Batch normalization unifies the distribution of feature-map values by setting them to zero mean and unit variance. Further, it smoothens the flow of gradient and acts as a regulating factor, which helps in improving the generalization of the neural network.

Dropout may be performed on the CNN to introduce regularization within the neural network, which improves generalization by randomly skipping some units or connections with a certain probability. This random dropping of some connections or units produces several thinned neural network architectures, and finally, one representative neural network is selected with small weights. This selected neural network architecture is then considered as an approximation of all of the proposed neural networks. In the CNN model, the dropout ratio was optimized using grid search as a hyperparameter.

The CNN may comprise fully connected layers (e.g., output layers), which are used at the end of the neural network for classification and/or prediction. Unlike pooling and convolution, it is a global operation. It takes input from feature extraction stages and globally analyses the output of all the preceding layers.

Example 6: R Software Program Configured to Perform the DeepLearning Algorithm Using systems and methods of the present disclosure, an R software program was configured to perform the Deep-Learning algorithm. The R software program, which may be stored on a non-transitory computer-readable medium, may comprise machine-executable code that, upon execution by one or more computer processors, implements numerous operations of an example of a DeepLearning algorithm, including constructing a DeepLearning model, calculating the performance of the DeepLearning algorithm, performing phenotype analysis using a set of predictor SNPs (e.g., known SNPs that are associated with an inflammatory disease), training the DeepLearning model by performing prediction of the inflammatory disease using a training dataset, performing prediction of the inflammatory disease using a test dataset, performing cross-validation, and constructing a combined DeepLearning model out of a plurality of separate DeepLearning models.

An example of code for an R software program configured to perform the DeepLearning algorithm is provided below.

```
### Begin R code software program
rm(list=ls(all=T))
work.dir<- getwd()
setwd(work.dir)
Interm.dir = paste(work.dir,"Interm/",sep="")
```

```
dir.create(Interm.dir)
res.dir = paste(work.dir,"results/",sep="")
dir.create(res.dir)
dir.create(paste(res.dir,"/fibdgc cedars 09132018/best/",sep=""))
library(h2o)
library(e1071)
Re-calculate the performance of the DL algorithm in family ctrls
h2o.shutdown( )
#### Analysis starts
First, prediction using known SNPs
h2o.init(nthreads=-1,max_mem_size="1000G")
name.known.tr2.g=paste(Interm.dir,"g_known_tr2_08292018.csv",
sep="")
name.known.va.g=paste(Interm.dir,"g_known_va_08292018.csv",sep="")
name.known.tr.g=paste(Interm.dir,"g_known_tr_08292018.csv",sep="")
name.known.te.g=paste(Interm.dir,"g_known_te_08292018.csv",sep="")
dat.known.tr=h2o.importFile(name.known.tr.g,"dat.known.tr")
dat.known.tr2=h2o.importFile(name.known.tr2.g,"dat.known.tr2")
dat.known.te=h2o.importFile(name.known.te.g,"dat.known.te")
dat.known.va=h2o.importFile(name.known.va.g,"dat.known.va")
dat.known.tr$PHENOTYPE=as.factor(dat.known.tr$PHENOTYPE)
dat.known.tr2$PHENOTYPE=as.factor(dat.known.tr2$PHENOTYPE)
dat.known.va$PHENOTYPE=as.factor(dat.known.va$PHENOTYPE)
dat.known.te$PHENOTYPE=as.factor(dat.known.te$PHENOTYPE)
snps.known=read.table(paste(Interm.dir,"known_snps_list_08292018.txt",
sep=""))
Analysis using DeepLearning
response="PHENOTYPE"
predictors=snps.known[,1]
dat.known.split=h2o.splitFrame(dat.known.tr)
dat.known.tr2=dat.known.split[[1]]
dat.known.va=dat.known.split[[2]]
#### Run the DeepLearning model (takes several days' runtime)
m_165_2_cv_known=h2o.deeplearning(model_id=
"m_165_2_cv_known",
    training_frame=dat.known.tr,
        #validation_frame=dat.known.te,
        x=predictors,y=response,
        hidden=c(165,165),
        activation="MaxoutWithDropout",
        #activation="Rectifier",
        #activation="Maxout",
        input_dropout_ratio=0.1,
        epochs=10,
        overwrite_with_best_model=T,
        nfold=10,
        fold_assignment="AUTO",
        l1=1.1E-4,
        l2=6.0E-5,
        #loss = "CrossEntropy",
        keep_cross_validation_predictions = TRUE,
        #missing_values_handling = "MeanImputation",
        score_validation_samples=10000,
        stopping_round=2,
        stopping_metric="AUC",
        stopping_tolerance=0.0001,
        seed=1
    )
summary(m_165_2_cv_known)
name.known.te.info=paste(Interm.dir,"info_known_te_08292018.csv",
sep="")
info.known.te=read.table(name.known.te.info,sep=",")
name.known.tr.info=paste(Interm.dir,"info_known_tr_08292018.csv",
sep="")
info.known.tr=read.table(name.known.tr.info,sep=",")
#### Perform prediction in training dataset
cros.pred=h2o.cross_validation_predictions(m_165_2_cv_known)
pred={ }
for(i in 1:5){
    pred.i=as.vector(((cros.pred[[i]])$p1)$p1)
    pred=cbind(pred,pred.i)
}
pred.dl.known=rowMeans(pred)*5
#pred.dl.known=as.vector((pred.dl.known$p1)$p1)
info.known.tr2=cb in d(info.known.tr, pred.dl.known)
colnames(info.known.tr2)[7]="pred_dl_known"
#### Perform prediction in test dataset
pred.v.known.dl=h2o.predict(m_165_2_cv_known,
newdata=dat.known.te)
name.known.te.info=paste(Interm.dir,"info_known_te_08292018.csv",
```

```
sep="")
info.known.te=read.table(name.known.te.info,sep=",")
pred.dl.known=as.vector((pred.v.known.dl$p1)$p1)
info.known.te=cbind(info.known.te,pred.dl.known)
colnames(info.known.te)[7]="pred_dl_known"
Save the constructed DeepLearning model
h2o.saveModel(m_165_2_cv_known,path=paste(res.dir,
"/iibdgc_cedars_09132018/best/",sep=""),force=T)
#m_165_2_cv_known=h2o.loadModel(path=paste(res.dir,
"/iibdgc_cedars_09132018/best/m_165_2_cv_known",sep=""))
#### Obtain the best performing DeepLearning model
#auc.i=h2o.auc(m_160_2_cv_known)
##############################################
#### Perform prediction using the rest of iChip
##############################################
name.other.tr.g=paste(Interm.dir,"g_others_tr_08292018.csv",sep="")
name.other.te.g=paste(Interm.dir,"g_others_te_08292018.csv",sep="")
dat.other.tr=h2o.importFile(name.other.tr.g,"dat.other.tr")
dat.other.te=h2o.importFile(name.other.te.g,"dat.other.te")
dat.other.tr$PHENOTYPE=as.factor(dat.other.tr$PHENOTYPE)
snps.other=read.table(paste(Interm.dir,"others_snps_list_08292018.txt",
sep=""))
#### Perform analysis using DeepLearning
response="PHENOTYPE"
predictors=snps.other[,1]
dat.other.split=h2o.splitFrame(dat.other.tr)
dat.other.tr2=dat.other.split[[1]]
dat.other.va=dat.other.split[[2]]
Note: this takes weeks of runtime, even on a powerful
workstation
m_32_3_cv_others=h2o.deeplearning(model_id="m_325_3_cv_other",
        training_frame=dat.other.tr,
        #validation_frame=dat.te,
        x=predictors,y=response,
        hidden=c(325,325,325),
        #activation="Tanh",
        activation="RectifierWithDropout",
        input_dropout_ratio=.1,
        epochs=10,
        overwrite_with_best_model=T,
        nfold=5,
        fold_assignment="AUTO",
        l1=6.0E-5,
        l2=1.0E-4,
        keep_cross_validation_predictions = TRUE,
        score_validation_samples=10000,
        stopping_round=2,
        stopping_metric="AUC",
        stopping_tolerance=0.001
    )
Obtain the predictions
name.others.te.info=paste(Interm.dir,"info_others_te_08292018.csv",
sep="")
info.others.te=read.table(name.others.te.info,sep=",")
name.others.tr.info=paste(Interm.dir,"info_others_tr_09292018.csv",
sep="")
info.others.tr=read.table(name.others.tr.info,sep=",")
In training set
cros.pred=h2o.cross_validation_predictions(m_325_3_cv_others)
pred={ }
for(i in 1:5){
    pred.i=as.vector(((cros.pred[[i]])$p1)$p1)
    pred=cbind(pred,pred.i)
}
pred.dl.others=rowMeans(pred)*5
#pred.dl.others=as.vector((pred.dl.others$p1)$p1)
info.others.tr2=cbind(info.others.tr,pred.dl.others)
colnames(info.others.tr2)[7]="pred_dl_others"
In test set
pred.v.others.dl=h2o.predict(m_325_3_cv_others,newdata=dat.other.te)
pred.dl.others=as.vector((pred.v.others.dl$p1)$p1)
info.others.te2=cbind(info.others.te,pred.dl.others)
colnames(info.others.te2)[7]="pred_dl_others"
#### DeepLearning combined
info_comb_tr =
merge(info.known.tr[,c("FID","PHENOTYPE","pred_dl_known")],
info.others.tr[,c("FID","pred_dl_others")])
info_comb_tr$PHENOTYPE = as.factor(info_comb_tr$PHENOTYPE)
model_comb = svm(PHENOTYPE~pred_dl_others+pred_dl_known,
```

-continued

```
data = info_comb_tr,kernal = "radial",epsilon = 0.05, tolerance = 5E−4)
    info_comb_te =
merge(info.known.te[,c("FID","PHENOTYPE","pred_dl_known")],
info.others.te[,c("FID","pred_dl_others")])
    #info_comb_te$PHENOTYPE = as.factor(info_comb_te$PHENOTYPE)
    predict(model_comb,newdata = info_comb_te)
```

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for determining a risk of developing Crohn's disease in a subject, comprising:

(a) obtaining a biological sample from the subject;

(b) selectively amplifying and tagging a plurality of target DNA molecules from the biological sample;

(c) sequencing or genotyping the plurality of amplified and tagged target DNA molecules from the biological sample from the subject to generate a dataset comprising genetic data;

(d) generating, based at least on the dataset comprising the genetic data, a Crohn's disease profile of the biological sample of the subject;

wherein the Crohn's disease profile is generated to include a difference between a plurality of feature sets from different timepoints;

wherein the generating the Crohn's disease profile includes processing, using one or more data processor, the dataset to determine, for inclusion in each feature set of the plurality of feature sets, one or more quantitative measures indicative of a presence, an absence, and/or a relative quantity of a plurality of known susceptibility variants at the timepoint of the biological sample; and wherein the plurality of known susceptibility variants include rs5743293, rs2066845, and rs3116496;

(e) applying, using the one or more data processors, a deep learning prediction model trained to account for one or more non-linear, higher order combinatorial effects of the plurality of known susceptibility variants within a single timepoint and across the plurality of timepoints;

wherein the deep learning prediction model is applied to the Crohn's disease profile to determine a change in a risk of developing Crohn's disease in the subject;

wherein the deep learning prediction model includes a plurality of data pre-processing layers followed by one or more fully-connected layers; and wherein the plurality of pre-processing layers down-sample each feature set to reduce a dimension of each feature set; and (f) administering, based at least on the change in the risk of developing Crohn's disease in the subject, a therapeutic intervention including one or more immuno-modulators, wherein a different immunomodulator than a current immunomodulator of the subject is administered in response to the change in risk of developing the Crohn's disease comprising an elevated risk.

2. The method of claim 1, wherein the deep learning prediction model comprises a deep learning algorithm comprises one or more of a neural network, a random forest model, and a gradient-boosted model.

3. The method of claim 1, wherein the Crohn's disease profile is further generated by at least applying the deep learning prediction model to a set of clinical health data of the subject, and wherein the clinical health data of the subject comprises having or not having a familial history of an inflammatory disease or disorder, having or not having hypertension or pre-hypertension, having or not having diabetes or pre-diabetes, being or not being overweight or obese, smoking or not smoking, drinking or not drinking alcohol, using or not using drugs, or any combination of one or more thereof.

4. The method of claim 1, wherein the Crohn's disease profile further comprises one or more serological markers.

5. The method of claim 1, wherein the change in the risk of developing Crohn's disease is determined at a sensitivity of at least about 70%.

6. The method of claim 1, wherein the change in the risk of developing Crohn's disease is determined at a specificity of at least about 70%.

7. The method of claim 1, wherein the change in the risk of developing Crohn's disease is determined at a positive predictive value of at least about 70%.

8. The method of claim 1, wherein the change in the risk of developing Crohn's disease is determined at a negative predictive value of at least about 70%.

9. The method of claim 1, wherein the change in the risk of developing Crohn's disease is determined with an Area Under Curve (AUC) of at least about 0.70.

10. The method of claim 1, further comprising:

training the deep learning prediction model using a first set of independent training samples associated with a presence of the Crohn's disease and a second set of independent training samples associated with an absence of the Crohn's disease.

11. The method of claim 1, further comprising optimizing a set of hyperparameters of the deep learning prediction model.

12. The method of claim 11, wherein the set of hyperparameters is optimized by at least performing a grid search.

13. The method of claim 11, wherein the optimizing the set of hyperparameters includes optimizing a number of layers and/or a number of neurons of a neural network comprising the deep learning prediction model.

14. The method of claim 1, wherein the deep learning prediction model comprises an ensemble of a plurality of neural networks, random forest models, and/or gradient boosted models.

15. The method of claim 4, wherein the one or more serological markers comprise ANCA, CBir1, IgA-ASCA, or IgG-ASCA, or a combination of two or more thereof.

16. The method of claim 1, wherein the therapeutic intervention further includes one or more of (i) terminating the current therapeutic intervention of the subject and (ii) a secondary clinical test where the change in risk of developing the Crohn's disease comprises an elevated risk.

17. The method of claim 1, wherein the therapeutic intervention comprises one or more of (i) continuing the current therapeutic intervention of the subject and (ii) a secondary clinical test where the change in the risk of developing Crohn's disease comprises a decreased risk of Crohn's disease.

18. The method of claim 1, further comprising:

applying, using the one or more data processors, the deep learning prediction model to the Crohn's disease profile to determine, based at least on the difference between the plurality of feature sets, an efficacy or a non-efficacy of a current therapeutic intervention of the subject; and administering, based at least on the non-efficacy of the current therapeutic intervention of the subject, the different therapeutic intervention instead of the current therapeutic intervention.

19. The method of claim 1, wherein the one or more immunomodulators include an anti-tumor necrosis factor alpha (TNFa) therapy, a glucocorticosteriod, an anti-TNF therapy, an anti-a4-b7 therapy, an anti-IL12p40 therapy, Thalidomide, and/or Cytoxin.

\* \* \* \* \*